US012779045B2

(12) United States Patent
Andrews et al.

(10) Patent No.: US 12,779,045 B2
(45) Date of Patent: Nov. 3, 2026

(54) HUMAN CD33 ANTIBODIES AND GLUCOCORTICOID CONJUGATES

(71) Applicant: Eli Lilly and Company, Indianapolis, IN (US)

(72) Inventors: Forest Hoyt Andrews, Carmel, IN (US); Joshua Ryan Clayton, Fishers, IN (US); Ross Edward Fellows, Westfield, IN (US); Bo Ma, San Diego, CA (US); Ying Tang, San Diego, CA (US); Jacqueline Mary Wurst, Zionsville, IN (US); Pia Pauliina Yachi, San Diego, CA (US); Chiao-Wen Yang, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 565 days.

(21) Appl. No.: 18/338,468

(22) Filed: Jun. 21, 2023

(65) Prior Publication Data

US 2024/0173425 A1 May 30, 2024

Related U.S. Application Data

(60) Provisional application No. 63/354,445, filed on Jun. 22, 2022.

(51) Int. Cl.

| | |
|---|---|
| ***A61K 47/68*** | (2017.01) |
| ***A61K 39/00*** | (2006.01) |
| ***A61P 37/06*** | (2006.01) |
| ***C07K 1/107*** | (2006.01) |
| ***C07K 16/28*** | (2006.01) |

(52) U.S. Cl.

CPC ...... *A61K 47/6849* (2017.08); *A61K 47/6803* (2017.08); *A61K 47/6889* (2017.08); *A61P 37/06* (2018.01); *C07K 1/1077* (2013.01); *C07K 16/2803* (2013.01); *A61K 2039/505* (2013.01); *C07K 2317/92* (2013.01)

(58) Field of Classification Search

CPC ............ A61K 47/6849; A61K 47/6803; C07K 16/2803; C07K 2317/21

See application file for complete search history.

(56) References Cited

FOREIGN PATENT DOCUMENTS

| | | | |
|---|---|---|---|
| JP | 2017-505604 | A | 2/2017 |
| JP | 2018-518491 | A | 7/2018 |
| JP | 2020-532947 | A | 11/2020 |
| WO | 2012/074097 | A1 | 6/2012 |
| WO | 2017/062271 | A2 | 4/2017 |
| WO | 2017/210471 | A1 | 12/2017 |
| WO | 2018/089373 | A2 | 5/2018 |
| WO | 2018/232088 | A1 | 12/2018 |
| WO | 2019/006280 | A1 | 1/2019 |
| WO | 2021/202770 | A2 | 10/2021 |

OTHER PUBLICATIONS

Abedin, S., Blood., 136(Supplement 1): 9-10, 2020.
Alector, Inc., GlobeNewswire, Nov. 10, 2021.
Bothell, Wash. (Business Wire)., Jun. 19, 2017.
Kovlun, Y., et al., Mol. Cancer Ther., 17(6):1271-1279, 2018.
Perl, A., Hematology Am Soc Hematol Educ Program., (1):54-65, 2017.
Vasu, S., et al., Haematologica., 107(3):770-773, 2022.
PCT International Search Report and the Written Opinion of the International Searching Authority pertaining to international Application No. PCT/US2023/068763; Date of Mailing: Dec. 20, 2023; 20 pages.

*Primary Examiner* — Jeffrey Stucker
*Assistant Examiner* — Brittney E Donoghue
(74) *Attorney, Agent, or Firm* — Quarles & Brady, LLP

(57) ABSTRACT

The present disclosure provides human CD33 antibodies and antibody glucocorticoid receptor agonist conjugates and methods of using the conjugates for the treatment of myeloid cell associated diseases.

19 Claims, 8 Drawing Sheets

Specification includes a Sequence Listing.

*p = 0.05-0.01
**p = 0.01-0.001
***p = 0.001-0.0001
****p < 0.0001;
ANOVA Tukey

*p = 0.05-0.01
**p = 0.01-0.001
***p = 0.001-0.0001
****p < 0.0001;
ANOVA Tukey

*p = 0.05-0.01
**p = 0.01-0.001
***p = 0.001-0.0001
****p < 0.0001;
ANOVA Tukey

SEQUENCE LISTING

```
Sequence total quantity: 29
SEQ ID NO: 1            moltype = AA  length = 13
FEATURE                 Location/Qualifiers
source                  1..13
                        mol_type = protein
                        organism = synthetic construct
SEQUENCE: 1
AASGFTFSSY AMS                                                    13

SEQ ID NO: 2            moltype = AA  length = 10
FEATURE                 Location/Qualifiers
source                  1..10
                        mol_type = protein
                        organism = synthetic construct
SEQUENCE: 2
AISGSGGSTY                                                        10

SEQ ID NO: 3            moltype = AA  length = 9
FEATURE                 Location/Qualifiers
source                  1..9
                        mol_type = protein
                        organism = synthetic construct
SEQUENCE: 3
ARTYSNYDY                                                         9

SEQ ID NO: 4            moltype = AA  length = 11
FEATURE                 Location/Qualifiers
source                  1..11
                        mol_type = protein
                        organism = synthetic construct
SEQUENCE: 4
QASQPTFNYL N                                                      11

SEQ ID NO: 5            moltype = AA  length = 8
FEATURE                 Location/Qualifiers
source                  1..8
                        mol_type = protein
                        organism = synthetic construct
SEQUENCE: 5
YDASNLQT                                                          8

SEQ ID NO: 6            moltype = AA  length = 8
FEATURE                 Location/Qualifiers
```

```
source                  1..8
                        mol_type = protein
                        organism = synthetic construct
SEQUENCE: 6
QQYEDLPT                                                     8

SEQ ID NO: 7            moltype = AA  length = 116
FEATURE                 Location/Qualifiers
source                  1..116
                        mol_type = protein
                        organism = synthetic construct
SEQUENCE: 7
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARTY SNYDYWGQGT LVTVSS      116

SEQ ID NO: 8            moltype = AA  length = 106
FEATURE                 Location/Qualifiers
source                  1..106
                        mol_type = protein
                        organism = synthetic construct
SEQUENCE: 8
DIQMTQSPSS LSASVGDRVT ITCQASQPTF NYLNWYQQKP GKAPKLLIYD ASNLQTGVPS  60
RFSGSGSGTD FTFTISSLQP EDIATYYCQQ YEDLPTFGPG TKVDIK                106

SEQ ID NO: 9            moltype = AA  length = 446
FEATURE                 Location/Qualifiers
source                  1..446
                        mol_type = protein
                        organism = synthetic construct
SEQUENCE: 9
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARTY SNYDYWGQGT LVTVSSASTK  120
GPCVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALAAP IEKTISKAKG QPREPQVYTL PPSREEMTKN  360
QVSLTCLVKG FYPSDICVEW ESNGQPENNY KTTPPVLDSD GSFFLYSKLT VDKSRWQQGN  420
VFSCSVMHEA LHNHYTQKSL SLSPGK                                      446

SEQ ID NO: 10           moltype = AA  length = 213
FEATURE                 Location/Qualifiers
source                  1..213
                        mol_type = protein
                        organism = synthetic construct
SEQUENCE: 10
DIQMTQSPSS LSASVGDRVT ITCQASQPTF NYLNWYQQKP GKAPKLLIYD ASNLQTGVPS  60
RFSGSGSGTD FTFTISSLQP EDIATYYCQQ YEDLPTFGPG TKVDIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 11           moltype = DNA  length = 1338
FEATURE                 Location/Qualifiers
source                  1..1338
                        mol_type = other DNA
                        organism = synthetic construct
SEQUENCE: 11
gaggtgcagc tgttggagtc tgggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtat attactgtgc gaggacttat  300
agtaattatg actactgggg tcagggaacc ctggtcaccg tctcctcagc tagcaccaag  360
ggcccatgcg tcttccccct ggcaccctcc tccaagagca cctctggggg cacagcggcc  420
ctgggctgcc tggtcaagga ctacttcccc gaaccggtga cggtgtcgtg gaactcaggc  480
gcactgacca gcggcgtgca caccttcccg gctgtcctac agtcctcagg actctactcc  540
ctcagcagcg tggtgaccgt gccctccagc agcttgggca cccagaccta catctgcaac  600
gtgaatcaca agcccagcaa caccaaggtg gacaagagag ttgagcccaa atcttgtgac  660
aaaactcaca catgcccacc gtgcccagca cctgaagccg ccgggggacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta tgtggacggc  840
gtggaggtgc ataatgccaa gacaaagccg cgggaggagc agtacaacag cacgtaccgt  900
gtggtcagcg tcctcaccgt cctgcaccaa gactggctga atggcaagga gtacaagtgc  960
aaggtctcca acaaagccct cgccgccccc atcgagaaaa ccatctccaa agccaaaggg  1020
cagccccgag aaccacaggt gtacaccctg cccccatccc gggaggagat gaccaagaac  1080
caagtcagcc tgacctgcct ggtcaaaggc ttctatccca gcgacatctg cgtggagtgg  1140
gagagcaatg ggcagccgga gaacaactac aagaccacgc ctcccgtgct ggactccgac  1200
ggctccttct tcctctattc caagctcacc gtggacaaga gcaggtggca gcaggggaac  1260
gtcttctcat gctccgtgat gcatgaggct ctgcacaacc actacacgca gaagagcctc  1320
tccctgtctc cgggcaaa                                                1338
```

```
SEQ ID NO: 12          moltype = DNA  length = 639
FEATURE                Location/Qualifiers
source                 1..639
                       mol_type = other DNA
                       organism = synthetic construct
SEQUENCE: 12
gacatccaga tgacccagtc tccatcctcc ctgtctgcat ctgtaggaga cagagtcacc  60
atcacttgcc aggcgagtca gccgacgttc aattatttaa attggtatca gcagaaacca  120
gggaaagccc ctaagctcct gatctacgat gcatccaatt tgcaaacagg ggtcccatca  180
aggttcagtg gaagtggatc tgggacagat tttactttca ccatcagcag cctgcagcct  240
gaagatattg caacatatta ctgtcaacag tatgaggatc tccctacttt cggccctggg  300
accaaagtgg atatcaaacg aaccgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgc                         639

SEQ ID NO: 13          moltype = AA  length = 11
FEATURE                Location/Qualifiers
source                 1..11
                       mol_type = protein
                       organism = synthetic construct
SEQUENCE: 13
QASQPTYIYL N                                                       11

SEQ ID NO: 14          moltype = AA  length = 106
FEATURE                Location/Qualifiers
source                 1..106
                       mol_type = protein
                       organism = synthetic construct
SEQUENCE: 14
DIQMTQSPSS LSASVGDRVT ITCQASQPTY IYLNWYQQKP GKAPKLLIYD ASNLQTGVPS  60
RFSGSGSGTD FTFTISSLQP EDIATYYCQQ YEDLPTFGPG TKVDIK                 106

SEQ ID NO: 15          moltype = AA  length = 213
FEATURE                Location/Qualifiers
source                 1..213
                       mol_type = protein
                       organism = synthetic construct
SEQUENCE: 15
DIQMTQSPSS LSASVGDRVT ITCQASQPTY IYLNWYQQKP GKAPKLLIYD ASNLQTGVPS  60
RFSGSGSGTD FTFTISSLQP EDIATYYCQQ YEDLPTFGPG TKVDIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 16          moltype = DNA  length = 639
FEATURE                Location/Qualifiers
source                 1..639
                       mol_type = other DNA
                       organism = synthetic construct
SEQUENCE: 16
gacatccaga tgacccagtc tccatcctcc ctgtctgcat ctgtaggaga cagagtcacc  60
atcacttgcc aggcgagtca gcctacgtat atctatttaa attggtatca gcagaaacca  120
gggaaagccc ctaagctcct gatctacgat gcatccaatt tgcaaacagg ggtcccatca  180
aggttcagtg gaagtggatc tgggacagat tttactttca ccatcagcag cctgcagcct  240
gaagatattg caacatatta ctgtcaacag tatgaggatc tccctacttt cggccctggg  300
accaaagtgg atatcaaacg aaccgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgc                         639

SEQ ID NO: 17          moltype = AA  length = 9
FEATURE                Location/Qualifiers
source                 1..9
                       mol_type = protein
                       organism = synthetic construct
SEQUENCE: 17
AREYSNYDY                                                          9

SEQ ID NO: 18          moltype = AA  length = 11
FEATURE                Location/Qualifiers
source                 1..11
                       mol_type = protein
                       organism = synthetic construct
```

```
SEQUENCE: 18
QASQDVFRYL N                                                  11

SEQ ID NO: 19          moltype = AA  length = 116
FEATURE                Location/Qualifiers
source                 1..116
                       mol_type = protein
                       organism = synthetic construct
SEQUENCE: 19
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAREY SNYDYWGQGT LVTVSS      116

SEQ ID NO: 20          moltype = AA  length = 106
FEATURE                Location/Qualifiers
source                 1..106
                       mol_type = protein
                       organism = synthetic construct
SEQUENCE: 20
DIQMTQSPSS LSASVGDRVT ITCQASQDVF RYLNWYQQKP GKAPKLLIYD ASNLQTGVPS  60
RFSGSGSGTD FTFTISSLQP EDIATYYCQQ YEDLPTFGPG TKVDIK                106

SEQ ID NO: 21          moltype = AA  length = 446
FEATURE                Location/Qualifiers
source                 1..446
                       mol_type = protein
                       organism = synthetic construct
SEQUENCE: 21
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAREY SNYDYWGQGT LVTVSSASTK  120
GPCVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALAAP IEKTISKAKG QPREPQVYTL PPSREEMTKN  360
QVSLTCLVKG FYPSDICVEW ESNGQPENNY KTTPPVLDSD GSFFLYSKLT VDKSRWQQGN  420
VFSCSVMHEA LHNHYTQKSL SLSPGK                                      446

SEQ ID NO: 22          moltype = AA  length = 213
FEATURE                Location/Qualifiers
source                 1..213
                       mol_type = protein
                       organism = synthetic construct
SEQUENCE: 22
DIQMTQSPSS LSASVGDRVT ITCQASQDVF RYLNWYQQKP GKAPKLLIYD ASNLQTGVPS  60
RFSGSGSGTD FTFTISSLQP EDIATYYCQQ YEDLPTFGPG TKVDIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 23          moltype = DNA  length = 1338
FEATURE                Location/Qualifiers
source                 1..1338
                       mol_type = other DNA
                       organism = synthetic construct
SEQUENCE: 23
gaggtgcagc tgttggagtc tgggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtat attactgtgc gagggaatat  300
agtaattatg actactgggg tcagggaacc ctggtcaccg tctcctcagc tagcaccaag  360
ggcccatgcg tcttccccct ggcaccctcc tccaagagca cctctggggg cacagcggcc  420
ctgggctgcc tggtcaagga ctacttcccc gaaccggtga cggtgtcgtg gaactcaggc  480
gcactgacca gcggcgtgca caccttcccg gctgtcctac agtcctcagg actctactcc  540
ctcagcagcg tggtgaccgt gccctccagc agcttgggca cccagaccta catctgcaac  600
gtgaatcaca agcccagcaa caccaaggtg gacaagagag ttgagcccaa atcttgtgac  660
aaaactcaca catgcccacc gtgcccagca cctgaagccg ccgggggacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta tgtggacggc  840
gtggaggtgc ataatgccaa gacaaagccg cgggaggagc agtacaacag cacgtaccgt  900
gtggtcagcg tcctcaccgt cctgcaccaa gactggctga atggcaagga gtacaagtgc  960
aaggtctcca acaaagccct cgccgccccc atcgagaaaa ccatctccaa agccaaaggg  1020
cagccccgag aaccacaggt gtacaccctg cccccatccc gggaggagat gaccaagaac  1080
caagtcagcc tgacctgcct ggtcaaaggc ttctatccca gcgacatctg cgtggagtgg  1140
gagagcaatg ggcagccgga gaacaactac aagaccacgc ctcccgtgct ggactccgac  1200
ggctccttct tcctctattc caagctcacc gtggacaaga gcaggtggca gcaggggaac  1260
gtcttctcat gctccgtgat gcatgaggct ctgcacaacc actacacgca gaagagcctc  1320
tccctgtctc cgggcaaa                                                1338

SEQ ID NO: 24          moltype = DNA  length = 639
FEATURE                Location/Qualifiers
```

-continued

```
source                1..639
                      mol_type = other DNA
                      organism = synthetic construct
SEQUENCE: 24
gacatccaga tgacccagtc tccatcctcc ctgtctgcat ctgtaggaga cagagtcacc  60
atcacttgcc aggcgagtca ggacgttttc aggtatttaa attggtatca gcagaaacca  120
gggaaagccc ctaagctcct gatctacgat gcatccaatt tgcaaacagg ggtcccatca  180
aggttcagtg gaagtggatc tgggacagat tttactttca ccatcagcag cctgcagcct  240
gaagatattg caacatatta ctgtcaacag tatgaggatc tccctacttt cggccctggg  300
accaaagtgg atatcaaacg aaccgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgc                          639

SEQ ID NO: 25         moltype = AA  length = 364
FEATURE               Location/Qualifiers
source                1..364
                      mol_type = protein
                      organism = Homo sapiens
SEQUENCE: 25
MPLLLLLPLL WAGALAMDPN FWLQVQESVT VQEGLCVLVP CTFFHPIPYY DKNSPVHGYW  60
FREGAIISRD SPVATNKLDQ EVQEETQGRF RLLGDPSRNN CSLSIVDARR RDNGSYFFRM  120
ERGSTKYSYK SPQLSVHVTD LTHRPKILIP GTLEPGHSKN LTCSVSWACE QGTPPIFSWL  180
SAAPTSLGPR TTHSSVLIIT PRPQDHGTNL TCQVKFAGAG VTTERTIQLN VTYVPQNPTT  240
GIFPGDGSGK QETRAGVVHG AIGGAGVTAL LALCLCLIFF IVKTHRRKAA RTAVGRNDTH  300
PTTGSASPKH QKKSKLHGPT ETSSCSGAAP TVEMDEELHY ASLNFHGMNP SKDTSTEYSE  360
VRTQ                                                                 364

SEQ ID NO: 26         moltype = AA  length = 12
FEATURE               Location/Qualifiers
source                1..12
                      mol_type = protein
                      organism = synthetic construct
VAR_SEQ               7
                      note = X at position 7 is Phenylalanine or Tyrosine
VAR_SEQ               8
                      note = X at position 8 is Asparagine or Isoleucine
SEQUENCE: 26
QASQPTXXIY LN                                                        12

SEQ ID NO: 27         moltype = AA  length = 363
FEATURE               Location/Qualifiers
source                1..363
                      mol_type = protein
                      organism = Macaca fascicularis
SEQUENCE: 27
MPLLLLPLLW AGALAMDPRV RLEVQESVTV QEGLCVLVPC TFFHPVPYHT RNSPVHGYWF  60
REGAIVSLDS PVATNKLDQE VQEETQGRFR LLGDPSRNNC SLSIVDARRR DNGSYFFRME  120
KGSTKYSYKS TQLSVHVTDL THRPQILIPG ALDPDHSKNL TCSVPWACEQ GTPPIFSWMS  180
AAPTSLGLRT THSSVLIITP RPQDHGTNLT CQVKFPGAGV TTERTIQLNV SYASQNPRTD  240
IFLGEGSGRK ARKQGVVQGA IGGAGVTVLL ALCLCLIFFT VKTHRRKAAR TAVGRIDTHP  300
ATGPTSSKHQ KKSKLHGATE TSGCSGTTLT VEMDEELHYA SLNFHGMNPS EDTSTEYSEV  360
RTQ                                                                  363

SEQ ID NO: 28         moltype = AA  length = 215
FEATURE               Location/Qualifiers
source                1..215
                      mol_type = protein
                      organism = Homo sapiens
SEQUENCE: 28
DPNFWLQVQE SVTVQEGLCV LVPCTFFHPI PYYDKNSPVH GYWFREGAII SRDSPVATNK  60
LDQEVQEETQ GRFRLLGDPS RNNCSLSIVD ARRRDNGSYF FRMERGSTKY SYKSPQLSVH  120
VTDLTHRPKI LIPGTLEPGH SKNLTCSVSW ACEQGTPPIF SWLSAAPTSL GPRTTHSSVL  180
IITPRPQDHG TNLTCQVKFA GAGVTTERTI QLNVT                               215

SEQ ID NO: 29         moltype = AA  length = 215
FEATURE               Location/Qualifiers
source                1..215
                      mol_type = protein
                      organism = Macaca fascicularis
SEQUENCE: 29
DPRVRLEVQE SVTVQEGLCV LVPCTFFHPV PYHTRNSPVH GYWFREGAIV SLDSPVATNK  60
LDQEVQEETQ GRFRLLGDPS RNNCSLSIVD ARRRDNGSYF FRMEKGSTKY SYKSTQLSVH  120
VTDLTHRPQI LIPGALDPDH SKNLTCSVPW ACEQGTPPIF SWMSAAPTSL GLRTTHSSVL  180
IITPRPQDHG TNLTCQVKFP GAGVTTERTI QLNVS                               215
```

HUMAN CD33 ANTIBODIES AND GLUCOCORTICOID CONJUGATES

SEQUENCE LISTING FILE

The present application is being filed along with a Sequence Listing in ST.26 XML format. The Sequence Listing is provided as a file titled "22712_US sequence listing" created Jun. 1, 2023, and is 33.8 kilobytes in size. The Sequence Listing information in the ST.26 XML format is incorporated herein by reference in its entirety.

FIELD OF THE INVENTION

The present disclosure provides human CD33 antibodies and antibody glucocorticoid receptor agonist conjugates, methods of using the conjugates for the treatment of myeloid cell associated diseases, processes for preparing the conjugates, and pharmaceutical compositions comprising the human CD33 antibody glucocorticoid conjugates.

BACKGROUND OF THE INVENTION

Anti-human CD33 antibodies and conjugates have been previously described. Many of the antibodies are myeloid cell depleting antibodies that modulate CD33 mediated responses. For example, lintuzumab, a humanized antibody reported to deplete myeloid cells via ADCC and CDC activity and modulate CD33 mediated cytokine responses was terminated as a monotherapy in AML due to lack of efficacy; vadastuximab talirine a lintuzumab conjugate was terminated due to safety concerns, and lintuzumab Ac225 is currently in Phase I/II in AML. (Perl, A., Hematology Am Soc Hematol Educ Program., (1):54-65, 2017; Bothell, Wash. (BUSINESS WIRE)., Jun. 19, 2017; Abedin, S., Blood., 136(Supplement 1): 9-10, 2020). Other such anti-human CD33 antibody therapeutics include, BI 836858, which failed to show clinical activity in a Phase I AML study but is being evaluated in combination with other compounds in AML, IMGN779 currently in Phase I trial in AML, and gemtuzumab ozogamicin the only approved anti-human CD33 antibody conjugate for treatment of AML. (Vasu S, et al., Haematologica., 107(3):770-773, 2022; Mol. Cancer Ther., 17(6):1271-1279, 2018). AL003, a humanized CD33 antibody reported to modulate CD33 mediated responses is in Phase II trial for the treatment of Alzheimer's Disease. (Alector, Inc., GlobeNewswire, Nov. 10, 2021).

WO2017/210471 discloses certain glucocorticoid receptor agonists (GC) and immunoconjugates thereof useful for treating inflammatory diseases. WO2018/089373 discloses novel steroids, protein conjugates thereof, and methods for treating diseases, disorders, and conditions comprising administering the steroids and conjugates. To date, there are no approved human CD33 GC conjugates for the treatment of diseases, including myeloid cell associated diseases.

SUMMARY OF THE INVENTION

The present disclosure provides certain novel fully human CD33 antibodies that bind human CD33, do not deplete myeloid cells ("non-depleting anti-human CD33 antibody"), internalize into the myeloid cells, do not modulate CD33 mediated responses (e.g., cytokine expression, inflammatory responses), and do not significantly degrade CD33 ("non-degrading anti-human CD33 antibody"). The present disclosure further provides compositions comprising such anti-human CD33 antibodies and methods of using such anti-human CD33 antibodies and compositions. Such anti-human CD33 antibodies can be conjugated to a therapeutic agent (e.g., inflammatory agent, glucocorticoid, cytotoxic agent, siRNA, saRNA, peptide, small molecule, antibody and binding fragments thereof) for use in the targeted delivery of the therapeutic agent into human CD33 expressing myeloid cells for the treatment of myeloid cell associated diseases. Furthermore, certain anti-human CD33 antibodies of the present disclosure do not significantly impact availability of the CD33 receptor on the cell surface and thus may provide for repeated CD33-targeted delivery of a therapeutic agent into the myeloid cells. The present disclosure further provides certain novel fully human CD33 antibody glucocorticoid (GC) conjugates, wherein the antibody binds to human CD33. The present disclosure further provides compositions comprising novel anti-human CD33 antibody GC conjugates and methods of using such anti-human CD33 antibody GC conjugates and compositions thereof. The present disclosure further provides certain novel anti-human CD33 GC conjugates useful in the treatment of rheumatoid arthritis, systemic lupus erythematosus, lupus nephritis, cutaneous lupus, atopic dermatitis, psoriasis, inflammatory bowel diseases, multiple sclerosis, Sjogren's syndrome, fibrotic diseases such as scleroderma and macrophage activation syndrome. As such, certain anti-human CD33 antibodies and/or anti-human CD33 antibody GC conjugates provided herein have one or more of the following properties: 1) bind human CD33 and cynomolgus monkey CD33 with desirable binding affinities and/or association and dissociation rates, 2) internalize into the myeloid cells upon binding to CD33, 3) do not deplete myeloid cells, 4) do not elicit effector function activity (e.g., ADCC), 5) do not degrade cell surface or intracellular CD33, 6) do not significantly impact availability of CD33 cell surface receptor on myeloid cells, 7) modulate glucocorticoid receptor agonist mediated cytokine responses (e.g., inhibit IL-6 and TNFα) in vitro, 8) modulate target specific glucocorticoid receptor agonist mediated responses (e.g., inhibit target site specific tissue inflammation and gene expression e.g., FKBP5) in vivo, 9) low immunogenicity risk, 10) inhibit plasmacytoid dendritic cell differentiation and IFNα production in vitro, and/or 11) good developability profile e.g., acceptable stability, solubility, viscosity, low aggregation, hydrophobicity, and/or good pharmacokinetic profile to facilitate development, manufacturing, and/or formulation.

Accordingly, in some embodiments, provided herein is an antibody that binds human CD33 ("anti-human CD33 antibody"), wherein the antibody comprises a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 4, the LCDR2 comprises SEQ ID NO: 5, and the LCDR3 comprises SEQ ID NO: 6. In some embodiments, the anti-human CD33 antibody comprises a VH comprising SEQ ID NO: 7 and a VL comprising SEQ ID NO: 8. In some embodiments, the anti-human CD33 antibody comprises a heavy chain (HC) comprising SEQ ID NO: 9 and a light chain (LC) comprising SEQ ID NO: 10.

In some embodiments, provided herein is an antibody that binds human CD33, wherein the antibody comprises a VH and a VL, wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 13, the LCDR2 comprises SEQ ID NO: 5, and the LCDR3 comprises SEQ ID NO: 6. In some embodiments, the anti-human CD33 antibody comprises a VH comprising SEQ ID NO: 7 and a VL comprising SEQ ID NO: 14. In some embodiments, the anti-human CD33 antibody comprises a HC comprising SEQ ID NO: 9 and a light LC comprising SEQ ID NO: 15.

In some embodiments, provided herein is an antibody that binds human CD33 wherein the antibody comprises a VH and a VL, wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 26, the LCDR2 comprises SEQ ID NO: 5, and the LCDR3 comprises SEQ ID NO: 6. In such embodiments, the anti-human CD33 antibody comprises a VH comprising SEQ ID NO: 7 and a VL comprising SEQ ID NO: 8 or 14. In further embodiments, the anti-human CD33 antibody comprises a HC comprising SEQ ID NO: 9 and a LC comprising SEQ ID NO: 10 or 15.

In some embodiments, provided herein is an antibody that binds human CD33, wherein the antibody comprises a VH and a VL, wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 17, the LCDR1 comprises SEQ ID NO: 18, the LCDR2 comprises SEQ ID NO: 5, and the LCDR3 comprises SEQ ID NO: 6. In some embodiments, the anti-human CD33 antibody comprises a VH comprising SEQ ID NO: 19 and a VL comprising SEQ ID NO: 20. In some embodiments, the anti-human CD33 antibody comprises a HC comprising SEQ ID NO: 21 and a LC comprising SEQ ID NO: 22.

In some embodiments, the anti-human CD33 antibody is a fully human antibody. In some embodiments, the anti-human CD33 antibody is an internalizing antibody. In further embodiments, the anti-human CD33 antibody has a human IgG1 or a human IgG4 isotype.

In further embodiments, the anti-human CD33 antibody has a modified human IgG1 Fc region comprising a L234A, L235A and a P329A (EU numbering) also referred to as IgG1AAA, which has reduced or eliminated binding to the Fcγ and C1q receptors. In such embodiments, the anti-human CD33 antibody having the IgG1AAA modified Fc region has reduced or eliminated Fc effector function activity, such as antibody-dependent cell cytotoxicity (ADCC) and complement-dependent cytotoxicity (CDC) (all residues numbered according to EU numbering). Such an antibody is termed an "IgG1-effector null" antibody. In such embodiments, the anti-human CD33 antibody having the IgG1AAA modified Fc region does not deplete CD33 expressing cells (e.g., myeloid cells). In such embodiments, the anti-human CD33 antibody is a non-depleting antibody. In further embodiments the anti-human CD33 antibody having the IgG1AAA backbone has significantly reduced and/or eliminated degradation of the CD33 receptor when compared to IgG1. In such embodiments, the anti-human CD33 antibody is a non-degrading antibody.

In some embodiments, provided herein are antibody fragments (e.g., Fab or scFv) that bind human CD33, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 4, the LCDR2 comprises SEQ ID NO: 5, and the LCDR3 comprises SEQ ID NO: 6. In some embodiments, the anti-human CD33 antibody comprise a VH comprising SEQ ID NO: 7 and a VL comprising SEQ ID NO: 8.

In some embodiments, provided herein are antibody fragments (e.g., Fab or scFv) that bind human CD33, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 13, the LCDR2 comprises SEQ ID NO: 5, and the LCDR3 comprises SEQ ID NO: 6. In some embodiments, the anti-human CD33 antibody comprise a VH comprising SEQ ID NO: 7 and a VL comprising SEQ ID NO: 14.

In some embodiments, provided herein are antibody fragments (e.g., Fab or scFv) that bind human CD33, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 1, the HCDR2 comprises SEQ ID NO: 2, the HCDR3 comprises SEQ ID NO: 17, the LCDR1 comprises SEQ ID NO: 18, the LCDR2 comprises SEQ ID NO: 5, and the LCDR3 comprises SEQ ID NO: 6. In some embodiments, the anti-human CD33 antibody comprises a VH comprising SEQ ID NO: 19 and a VL comprising SEQ ID NO: 20.

In some embodiments, the anti-human CD33 antibody has a modified human IgG1 or human IgG4 constant domain comprising engineered cysteine residues for use in the generation of antibody conjugate compounds (also referred to as bioconjugates) (see WO 2018/232088 A1). More particularly in such embodiments, the anti-human CD33 antibody comprises a cysteine at amino acid residue 124 (EU numbering), or a cysteine at amino acid residue 378 (EU numbering); or a cysteine at amino acid residue 124 (EU numbering) and cysteine at amino acid residue 378 (EU numbering).

In some embodiments, the present disclosure provides nucleic acids encoding a HC or LC, or a VH or VL, of the novel antibodies that bind anti-human CD33, or vectors comprising such nucleic acids.

In some embodiments, the present disclosure provides a nucleic acid comprising a sequence of SEQ ID NO: 11, 12, 16, 23, or 24.

In some embodiments, nucleic acids encoding a heavy chain or light chain of the antibodies that bind anti-human CD33 are provided. In some embodiments nucleic acids comprising a sequence encoding SEQ ID NO: 9, 10, 15, 21 or 22 are provided. In some embodiments, nucleic acids comprising a sequence encoding an antibody heavy chain that comprises SEQ ID NO: 9 or 21 is provided. For example, the nucleic acid can comprise a sequence of SEQ ID NO: 11 or 23. In some embodiments, nucleic acids comprising a sequence encoding an antibody light chain that comprises SEQ ID NO: 10, 15, or 22 is provided. For example, the nucleic acid can comprise a sequence of SEQ ID NO: 12, 16, or 24.

In some embodiments of the present disclosure, nucleic acids encoding a VH or VL of the anti-human CD33 antibodies are provided. In some embodiments, nucleic acids comprising a sequence encoding SEQ ID NO: 7, 8, 14, 19, or 20 are provided. In some embodiments, nucleic acids comprising a sequence encoding an antibody VH that comprises SEQ ID NO: 7 or 19 is provided. In some embodiments, nucleic acids comprising a sequence encoding an antibody VL that comprises SEQ ID NO: 8, 14, or 20 is provided.

Some embodiments of the present disclosure provide vectors comprising a nucleic acid sequence encoding an antibody heavy chain or light chain. For example, such vectors can comprise a nucleic acid sequence encoding SEQ ID NO: 9 or 21. In some embodiments, the vector comprises a nucleic acid sequence encoding SEQ ID NO: 10, 15 or 22.

Provided herein are also vectors comprising a nucleic acid sequence encoding an antibody VH or VL. For example, such vectors can comprise a nucleic acid sequence encoding SEQ ID NO: 7 or 19. In some embodiments, the vector comprises a nucleic acid sequence encoding SEQ ID NO: 8, 14, or 20.

Provided herein are also vectors comprising a first nucleic acid sequence encoding an antibody heavy chain and a second nucleic acid sequence encoding an antibody light chain. In some embodiments, the vector comprises a first nucleic acid sequence encoding SEQ ID NO: 9 or 21 and a second nucleic acid sequence encoding SEQ ID NO: 10, 15, or 22. In some embodiments, the vector comprises a first nucleic acid sequence encoding SEQ ID NO: 9 and a second nucleic acid sequence encoding SEQ ID NO: 10. In some embodiments, the vector comprises a first nucleic acid sequence encoding SEQ ID NO: 9 and a second nucleic acid sequence encoding SEQ ID NO: 15. In some embodiments, the vector comprises a first nucleic acid sequence encoding SEQ ID NO: 21 and a second nucleic acid sequence encoding SEQ ID NO: 22.

Also provided herein are compositions comprising a first vector comprising a nucleic acid sequence encoding an antibody heavy chain, and a second vector comprising a nucleic acid sequence encoding an antibody light chain. In some embodiments, the composition comprises a first vector comprising a nucleic acid sequence encoding SEQ ID NO: 9 or 21 and a second nucleic acid sequence encoding SEQ ID NO: 10, 15, or 22.

In some embodiments, the composition comprises a first vector comprising a nucleic acid sequence encoding SEQ ID NO: 9 and a second vector comprising a nucleic acid sequence encoding SEQ ID NO: 10. In some embodiments, the composition comprises a first vector comprising a nucleic acid sequence encoding SEQ ID NO: 9 and a second vector comprising a nucleic acid sequence encoding SEQ ID NO: 15. In some embodiments, the composition comprises a first vector comprising a nucleic acid sequence encoding SEQ ID NO: 21 and a second vector comprising a nucleic acid sequence encoding SEQ ID NO: 22.

Also provided herein are compositions comprising a vector comprising a nucleic acid sequence encoding an antibody heavy chain, and a nucleic acid sequence encoding an antibody light chain. In some embodiments, the composition comprises a vector comprising a nucleic acid sequence encoding SEQ ID NO: 9 or 21 and a second nucleic acid sequence encoding SEQ ID NO: 10, 15, or 22.

Nucleic acids of the present disclosure may be expressed in a host cell, for example, after the nucleic acids have been operably linked to an expression control sequence. Expression control sequences capable of expression of nucleic acids to which they are operably linked are well known in the art. An expression vector may include a sequence that encodes one or more signal peptides that facilitate secretion of the polypeptide(s) from a host cell. Expression vectors containing a nucleic acid of interest (e.g., a nucleic acid encoding a heavy chain or light chain of an antibody) may be transferred into a host cell by well-known methods, e.g., stable or transient transfection, transformation, transduction or infection. Additionally, expression vectors may contain one or more selection markers, e.g., tetracycline, neomycin, and dihydrofolate reductase, to aide in detection of host cells transformed with the desired nucleic acid sequences.

In another aspect, provided herein are cells, e.g., host cells, comprising the nucleic acids, vectors, or nucleic acid compositions described herein. A host cell may be a cell stably or transiently transfected, transformed, transduced or infected with one or more expression vectors expressing all or a portion of an antibody described herein. In some embodiments, a host cell may be stably or transiently transfected, transformed, transduced or infected with an expression vector expressing HC and LC polypeptides of an antibody of the present disclosure. In some embodiments, a host cell may be stably or transiently transfected, transformed, transduced, or infected with a first vector expressing HC polypeptides and a second vector expressing LC polypeptides of an antibody described herein. Such host cells, e.g., mammalian host cells, can express the antibodies that bind anti-human CD33 as described herein. Mammalian host cells known to be capable of expressing antibodies include CHO cells, HEK293 cells, COS cells, and NS0 cells.

In some embodiments, the cell, e.g., host cell, comprises a vector comprising a first nucleic acid sequence encoding SEQ ID NO: 9 or 21 and a second nucleic acid sequence encoding SEQ ID NO: 10, 15, or 22.

In some embodiments, the cell, e.g., host cell, comprises a first vector comprising a nucleic acid sequence encoding SEQ ID NO: 9 or 21 and a second vector comprising a nucleic acid sequence encoding SEQ ID NO: 10, 15, or 22.

In some embodiments, the cell, e.g., host cell, comprises a vector comprising a first nucleic acid sequence encoding SEQ ID NO: 9 or 21, and a second nucleic acid sequence encoding SEQ ID NO: 10, 15, or 22. In some embodiments, the cell, e.g., host cell, comprises a vector comprising a first nucleic acid sequence encoding SEQ ID NO: 9, and a second nucleic acid sequence encoding SEQ ID NO: 10. In some embodiments, the cell, e.g., host cell, comprises a vector comprising a first nucleic acid sequence encoding SEQ ID NO: 9, and a second nucleic acid sequence encoding SEQ ID NO: 15. In some embodiments, the cell, e.g., host cell, comprises a vector comprising a first nucleic acid sequence encoding SEQ ID NO: 21, and a second nucleic acid sequence encoding SEQ ID NO: 22.

The present disclosure further provides a process for producing an antibody that binds human CD33 as described herein by culturing the host cell described above, e.g., a mammalian host cell, under conditions such that the antibody is expressed and recovering the expressed antibody from the culture medium. The culture medium, into which an antibody has been secreted, may be purified by conventional techniques. Various methods of protein purification may be employed, and such methods are known in the art and described, for example, in Deutscher, Methods in Enzymology 182: 83-89 (1990) and Scopes, Protein Purification: Principles and Practice, 3rd Edition, Springer, NY (1994).

The present disclosure further provides antibodies or antigen binding fragments thereof produced by any of the processes described herein.

In another aspect, provided herein are pharmaceutical compositions comprising an antibody, nucleic acid, or vector described herein. Such pharmaceutical compositions can also comprise one or more pharmaceutically acceptable excipient, diluent or carrier. Pharmaceutical compositions can be prepared by methods well known in the art (e.g., *Remington: The Science and Practice of Pharmacy,* 22nd ed. (2012), A. Loyd et al., Pharmaceutical Press).

Given the anti-human CD33 antibodies described herein do not deplete myeloid cells, they offer advantages over myeloid cell depleting antibodies for treating myeloid cell associated immune diseases, e.g., avoid problematic concurrent immunocompromise, long-term immune suppression, other complications resulting from myeloid cell depletion and enhance/induce immunoregulatory functions of CD33 expressing myeloid cells. Further, as shown below, the anti-human CD33 antibodies described herein are internalized into the myeloid cells. Thus, the anti-human CD33 antibodies described herein can be conjugated to a therapeutic agent for targeted delivery of the therapeutic agent into human myeloid cells to elicit immunomodulatory or other therapeutic effects by the therapeutic agent for treatment of myeloid cell associated diseases. Furthermore, the anti-human CD33 antibodies described herein do not significantly degrade cell surface or intracellular CD33 nor do they significantly impact availability of the CD33 receptor on the cell surface, and thus, the anti-human CD33 antibodies described herein may allow for repeated CD33 targeted delivery of the therapeutic agents to the myeloid cell for treatment of myeloid cell associated diseases.

In some embodiments, provided herein are methods of treating a myeloid cell associated disease (e.g., immune diseases, neurodegenerative diseases, or myeloid cell associated cancer) in a subject (e.g., a human patient) in need thereof, by administering to the subject an effective amount of an anti-human CD33 antibody conjugated to a therapeutic agent, or a pharmaceutically acceptable salt thereof. In an embodiment, the present disclosure provides an anti-human CD33 antibody conjugated to a therapeutic agent as disclosed herein, or a pharmaceutically acceptable salt thereof for use in therapy. In an embodiment, the present disclosure provides an anti-human CD33 antibody conjugated to a therapeutic agent as disclosed herein, or a pharmaceutically acceptable salt thereof for use in the treatment of a myeloid cell associated disease. In an embodiment, the present disclosure provides use of an anti-human CD33 antibody conjugated to a therapeutic agent as disclosed herein, or a pharmaceutically acceptable salt thereof, for the manufacture of a medicament for the treatment of a myeloid cell associated disease. The conjugates, nucleic acids, vectors, or pharmaceutical compositions described herein may be administered by parenteral routes (e.g., subcutaneous and intravenous). In some embodiments, the present disclosure provides a method of delivering a therapeutic agent to CD33 expressing myeloid cells for the treatment of a myeloid cell associated disease, wherein the therapeutic agent is conjugated to an anti-human CD33 antibody of the present disclosure, wherein the therapeutic agent elicits an immunomodulatory or other therapeutic effect.

Accordingly, in one embodiment, the invention provides a conjugate of Formula I:

Formula I $$[GC—L—S]_n—Ab$$

wherein Ab is an antibody that binds human CD33 ("anti-human CD33 antibody"), wherein

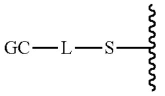

is:

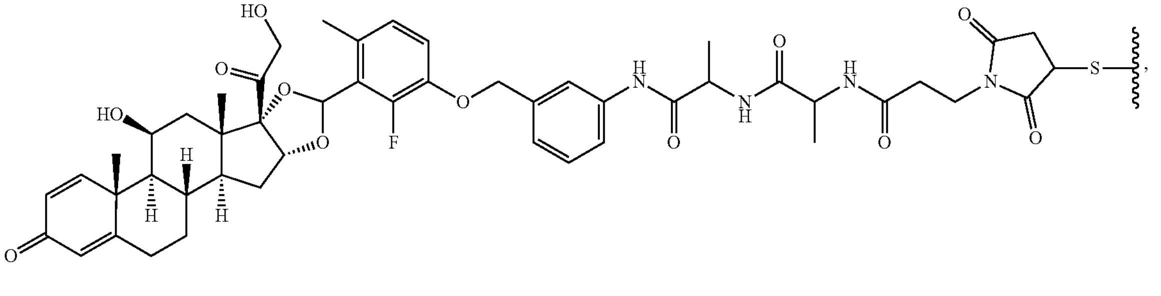

or

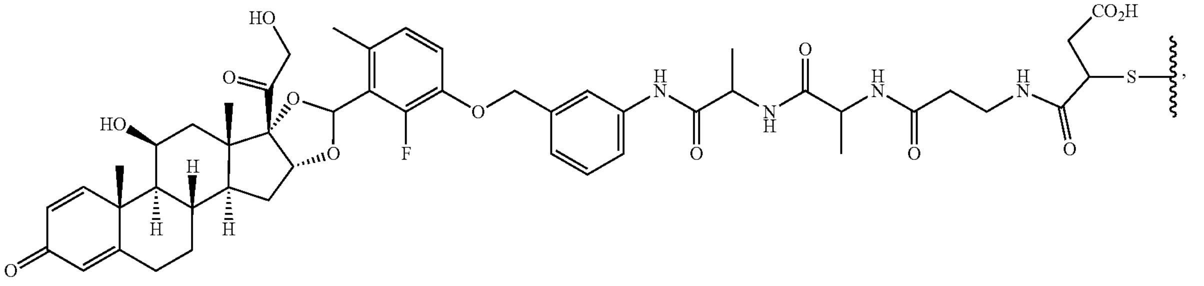

and n is 1-5.

In a further embodiment, the invention provides a conjugate of Formula I:

Formula I $[GC—L—S]_n—Ab$ wherein Ab is an anti-human human CD33, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;

the HCDR2 comprises SEQ ID NO: 2;

the HCDR3 comprises SEQ ID NO: 3 or 17;

the LCDR1 comprises SEQ ID NO: 4, 13, 18, or 26;

the LCDR2 comprises SEQ ID NO: 5; and the LCDR3 comprises SEQ ID NO: 6;

wherein

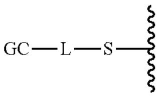

is:

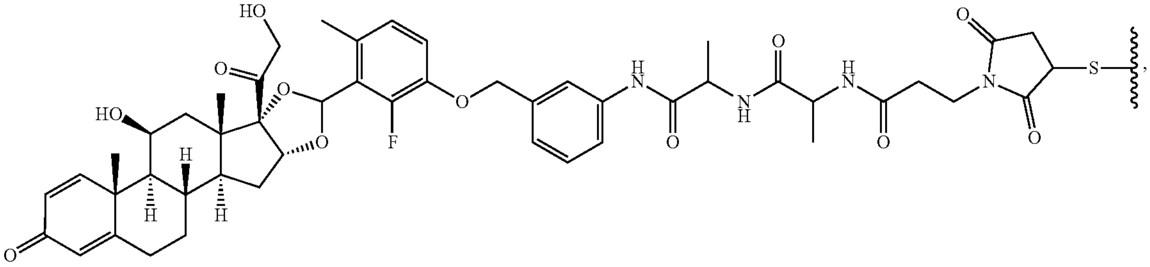

or

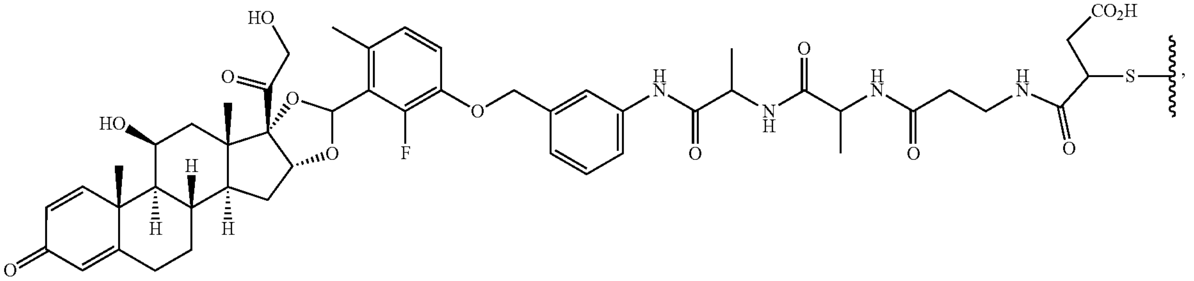

and n is 1-5.

In a further embodiment, the invention provides a conjugate of Formula I:

Formula I $[GC—L—S]_n—Ab$ wherein Ab is an anti-human CD33 antibody, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;

the HCDR2 comprises SEQ ID NO: 2;

the HCDR3 comprises SEQ ID NO: 3 or 17;

the LCDR1 comprises SEQ ID NO: 4, 13, 18, or 26;

the LCDR2 comprises SEQ ID NO: 5; and the LCDR3 comprises SEQ ID NO: 6;

wherein

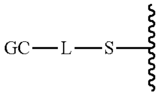

is:

-continued

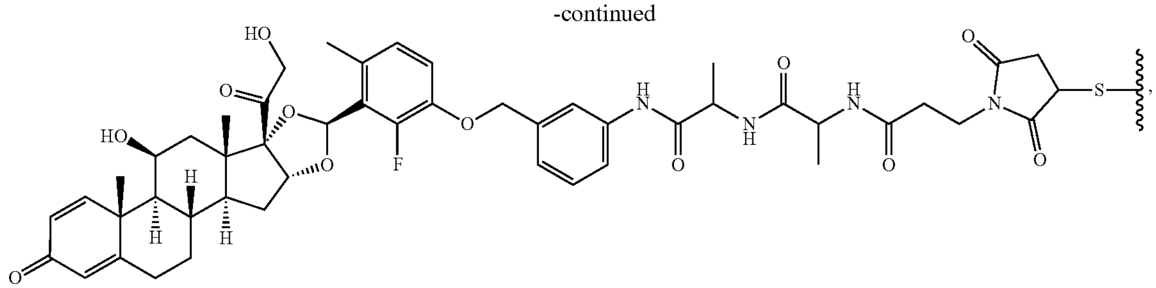

, or

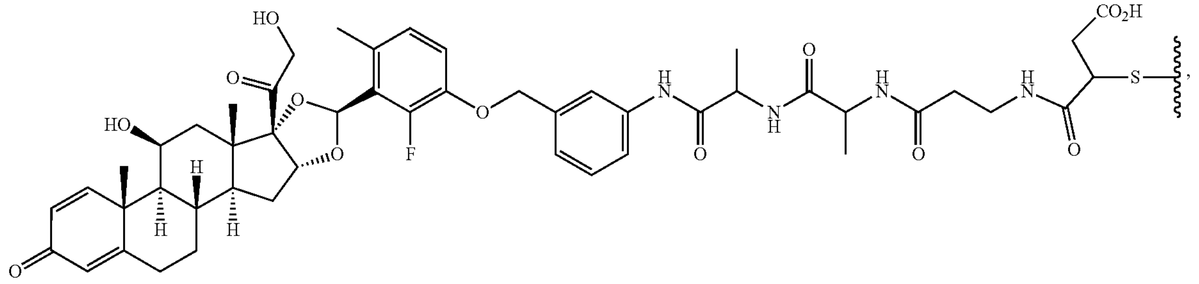

, and n is 1-5.

In a further embodiment, the invention provides a conjugate of Formula I:

Formula I $$[GC—L—S]_n—Ab$$

wherein Ab is an anti-human CD33 antibody, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;
the HCDR2 comprises SEQ ID NO: 2;
the HCDR3 comprises SEQ ID NO: 3 or 17;
the LCDR1 comprises SEQ ID NO: 4, 13, 18, or 26;
the LCDR2 comprises SEQ ID NO: 5; and
the LCDR3 comprises SEQ ID NO: 6;

wherein

GC—L—S— is:

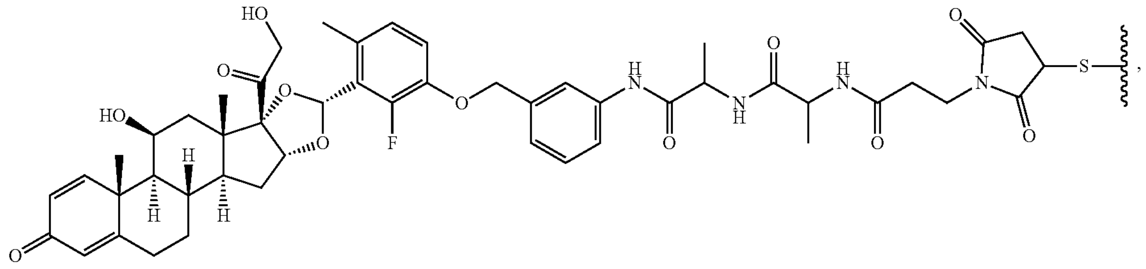

, or

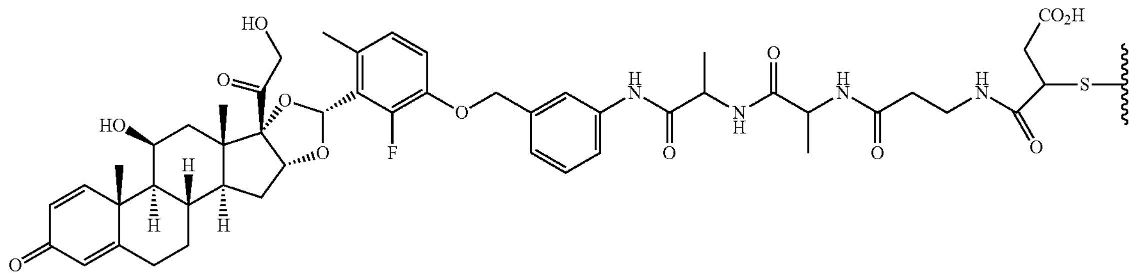

, and n is 1-5.

In a further embodiment, the invention provides a conjugate of Formula I:

Formula I $$[GC—L—S]_n—Ab$$

wherein Ab is an anti-human CD33 antibody, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;
the HCDR2 comprises SEQ ID NO: 2;
the HCDR3 comprises SEQ ID NO: 3 or 17;
the LCDR1 comprises SEQ ID NO: 4, 13, 18, or 26;
the LCDR2 comprises SEQ ID NO: 5; and
the LCDR3 comprises SEQ ID NO: 6;

wherein

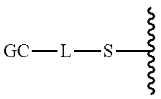 is:

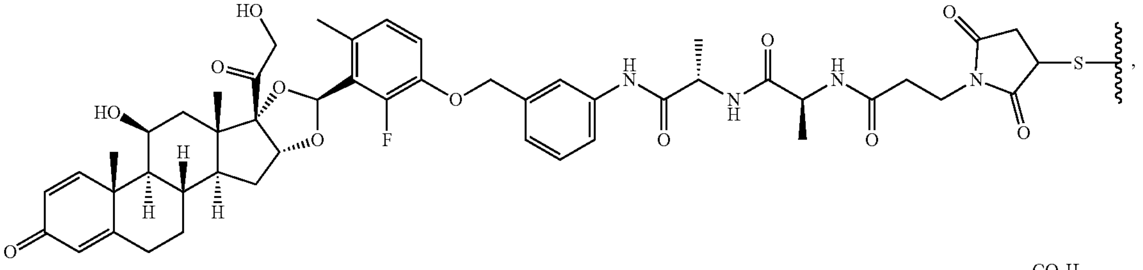

or

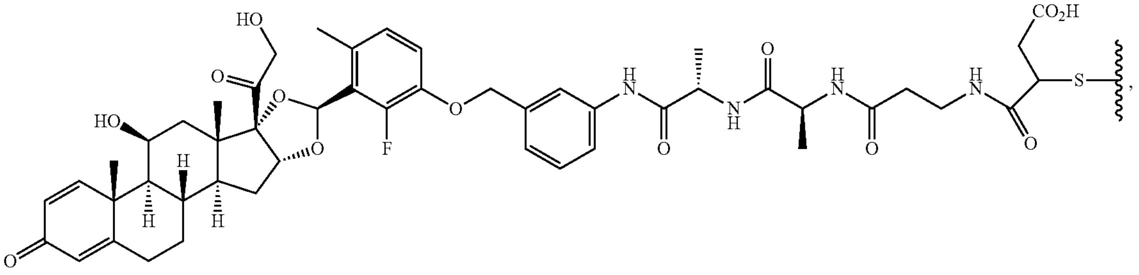

and n is 1-5.

In a further embodiment, the invention provides a conjugate of Formula I:

Formula I $$[GC—L—S]_n—Ab$$

wherein Ab is an anti-human CD33 antibody, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;
the HCDR2 comprises SEQ ID NO: 2;
the HCDR3 comprises SEQ ID NO: 3 or 17;
the LCDR1 comprises SEQ ID NO: 4, 13, 18, or 26;
the LCDR2 comprises SEQ ID NO: 5; and
the LCDR3 comprises SEQ ID NO: 6;

wherein

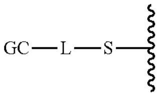 is:

-continued

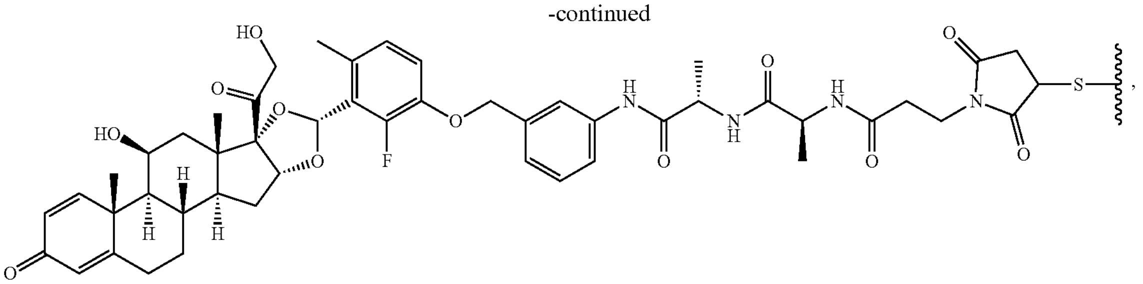

or

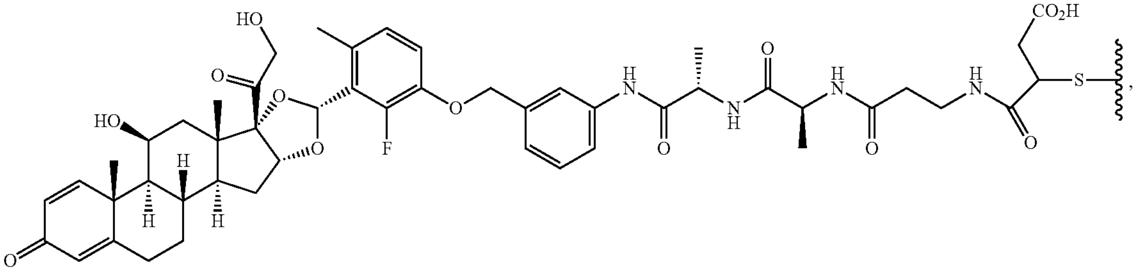

and n is 1-5.

In a further embodiment, the disclosure provides a conjugate of Formula I:

$$[GC—L—S]_n—Ab$$ Formula I wherein Ab is an anti-human CD33 antibody, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;
the HCDR2 comprises SEQ ID NO: 2;
the HCDR3 comprises SEQ ID NO: 3 or 17;
the LCDR1 comprises SEQ ID NO: 4, 13, 18, or 26;
the LCDR2 comprises SEQ ID NO: 5; and
the LCDR3 comprises SEQ ID NO: 6;

wherein

GC—L—S— is:

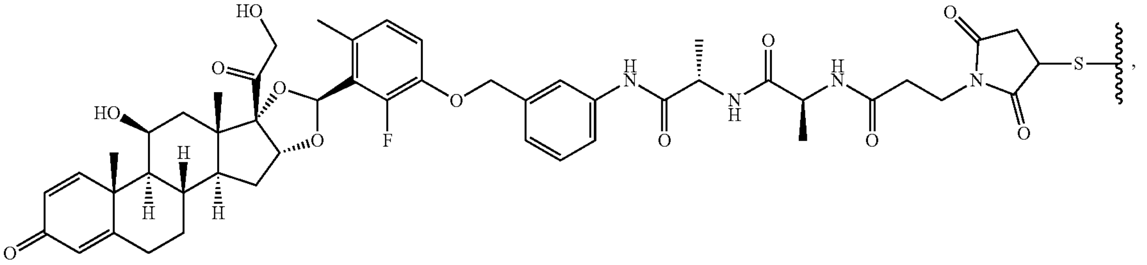

and n is 1-5.

In a further embodiment, the disclosure provides a conjugate of Formula I:

Formula I

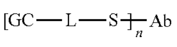

wherein Ab is an anti-human CD33 antibody, wherein Ab comprises a VH and a VL, wherein the VH comprises heavy chain complementarity determining regions HCDR1, HCDR2, and HCDR3, and the VL comprises light chain complementarity determining regions LCDR1, LCDR2, and LCDR3, wherein:

the HCDR1 comprises SEQ ID NO: 1;
the HCDR2 comprises SEQ ID NO: 2;
the HCDR3 comprises SEQ ID NO: 3 or 17;
the LCDR1 comprises SEQ ID NO: 4, 13, 18, or 26;
the LCDR2 comprises SEQ ID NO: 5; and
the LCDR3 comprises SEQ ID NO: 6;

wherein

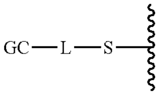

is:

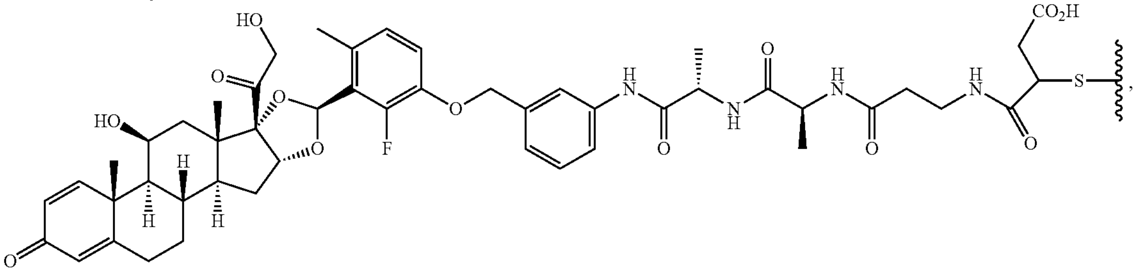

and n is 1-5.

In an embodiment, n is 2-5.

In an embodiment, n is 3-5.

In an embodiment, n is 3-4.

In an embodiment, n is 4.

In an embodiment, n is 3.

In an embodiment, n is 2.

In some embodiments, the Ab in the conjugate of Formula 1 comprises a VH and a VL, wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 4, the LCDR2 comprises SEQ ID NO: 5, and the LCDR3 comprises SEQ ID NO: 6. In some embodiments, the Ab comprises a VH comprising SEQ ID NO: 7 and a VL comprising SEQ ID NO: 8. In some embodiments, the Ab is Ab2, wherein Ab2 comprises a HC comprising SEQ ID NO: 9 and a LC comprising SEQ ID NO: 10.

In some embodiments, the Ab in the conjugate of Formula 1 comprises a VH and a VL, wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 13, the LCDR2 comprises SEQ ID NO: 5, and the LCDR3 comprises SEQ ID NO: 6. In some embodiments, the Ab comprises a VH comprising SEQ ID NO: 7 and a VL comprising SEQ ID NO: 14. In some embodiments, the Ab is Ab3, wherein Ab3 comprises a HC comprising SEQ ID NO: 9 and a LC comprising SEQ ID NO: 15.

In some embodiments, the Ab in the conjugate of Formula 1 comprises a VH and a VL, wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 1, the HCDR2 comprises SEQ ID NO: 2, the HCDR3 comprises SEQ ID NO: 17, the LCDR1 comprises SEQ ID NO: 18, the LCDR2 comprises SEQ ID NO: 5, and the LCDR3 comprises SEQ ID NO: 6. In some embodiments, the Ab comprises a VH comprising SEQ ID NO: 19 and a VL comprising SEQ ID NO: 20. In some embodiments, the Ab is Ab1, wherein Ab1 comprises a HC comprising SEQ ID NO: 21 and a LC comprising SEQ ID NO: 22.

As used herein, "GC" in the Formula:

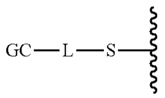

refers to a suitable glucocorticoid receptor agonist payload, wherein GC is one of the following Formulas IIa, IIb, or IIc:

Formula IIa

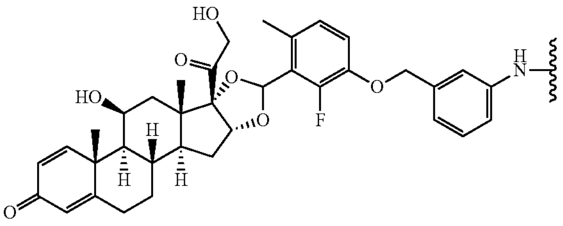

,

-continued

Formula IIb

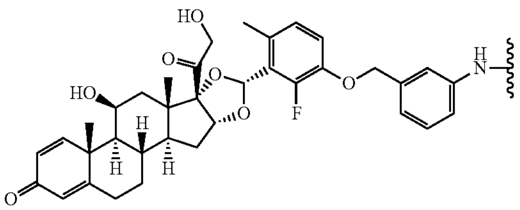

, and

Formula IIc

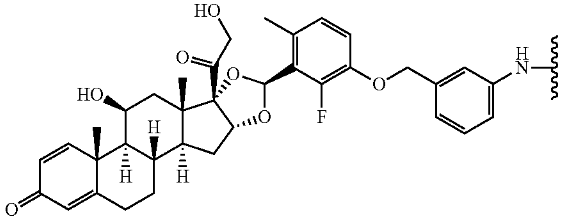

.

As used herein, "L" in the Formula

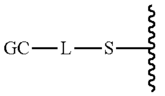

refers to a suitable linker group which connects Ab to the GC. Suitable linkers known to those of ordinary skill in the art include, for example, cleavable and noncleavable linkers. More specifically, suitable linkers "L" is one of the following of Formulas IIIa through Formula IIIa

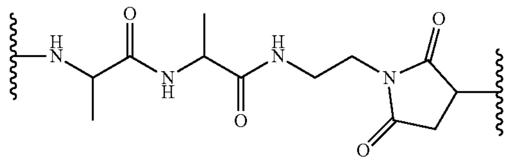

,

-continued

Formula IIIb

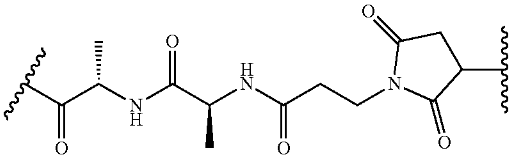

,

Formula IIIc

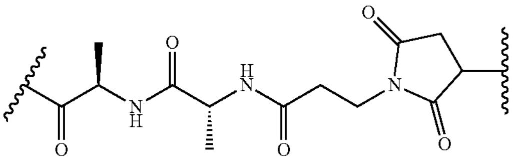

,

Formula IIId

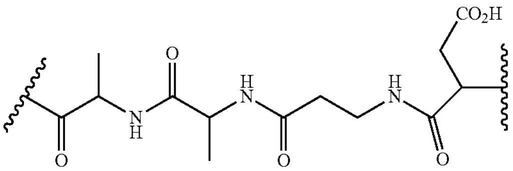

,

Formula IIIe

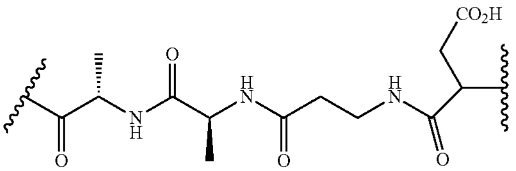

, and

Formula IIIf

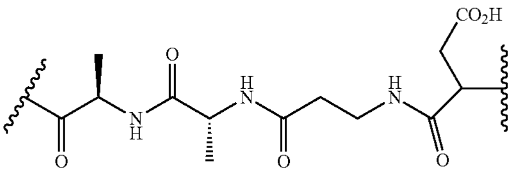

.

In an embodiment, the disclosure provides a glucocorticoid receptor agonist payload-linker of Formula IV:

Formula IV

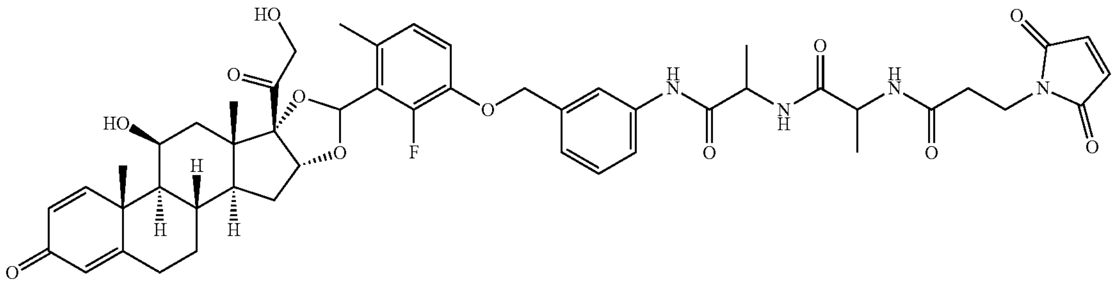

.

In an embodiment, the disclosure provides a glucocorticoid receptor agonist payload-linker of Formula IVa:

Formula IVa

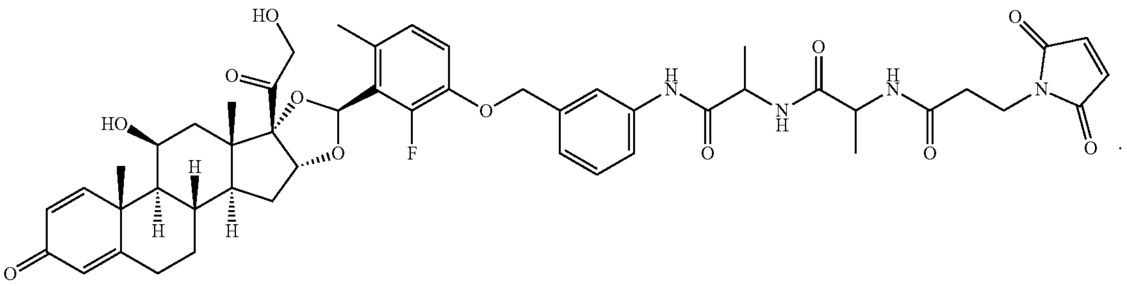

In an embodiment, the disclosure provides a glucocorticoid receptor agonist payload-linker of Formula IVb:

Formula IVb

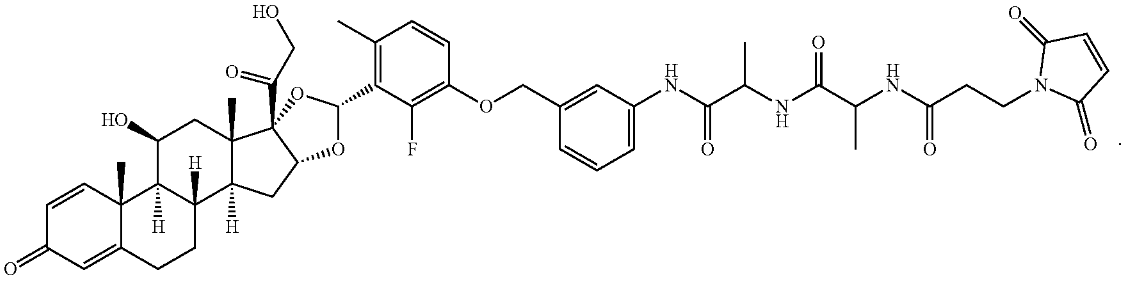

In an embodiment, the disclosure provides a glucocorticoid receptor agonist payload-linker of Formula IVc:

Formula IVc

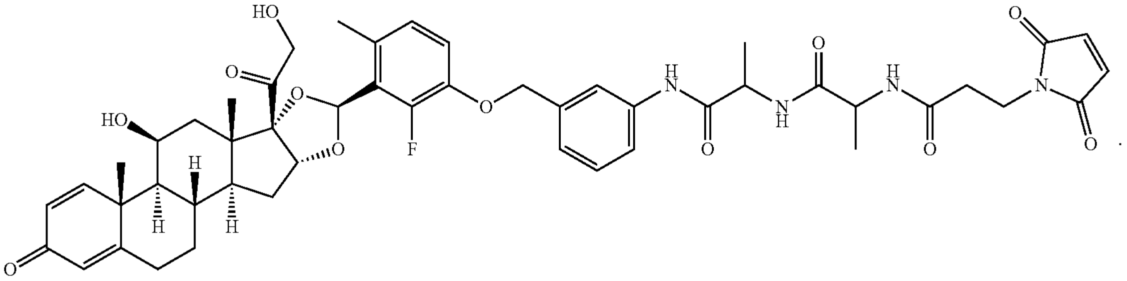

In an embodiment, the disclosure provides a glucocorticoid receptor agonist payload-linker of Formula IVd:

Formula IVd

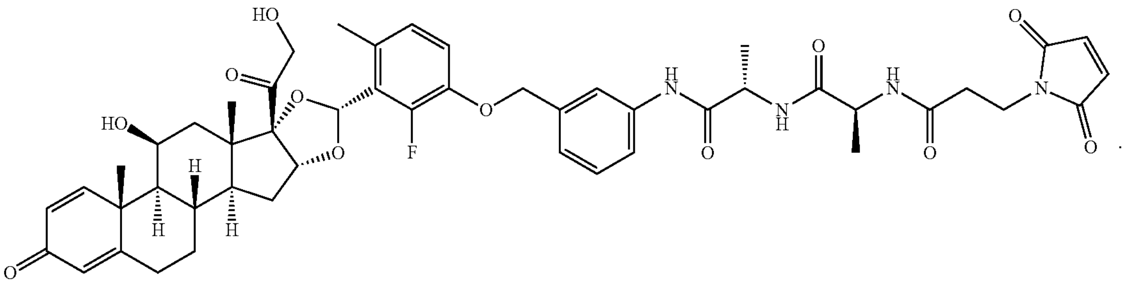

In an embodiment, the disclosure provides a conjugate of Formula V:

Formula V

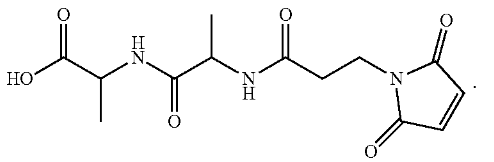

In a further embodiment, the disclosure provides a conjugate of Formula Va:

Formula Va

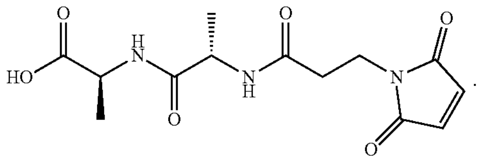

In some embodiments, the Conjugate of Formula I modulates CD33 target specific glucocorticoid receptor agonist mediated responses. In such embodiments the Conjugate of Formula I modulates CD33 target specific glucocorticoid receptor agonist mediated response such as inflammatory responses, cytokine expression, and/or glucocorticoid receptor agonist mediated gene expression.

Because of their critical role in regulating immune responses, dysregulation of myeloid cells is associated with a variety of myeloid cell associated immune diseases including autoimmune/inflammatory diseases, which are caused by abnormal activation (increased pro-inflammatory cytokines) of myeloid and lymphoid cells. Examples of myeloid cell associated immune diseases include rheumatoid arthritis, systemic lupus erythematosus, lupus nephritis, cutaneous lupus, giant cell arteritis, polymyalgia rheumatica, psoriatic arthritis, atopic dermatitis, psoriasis, ulcerative colitis, Crohn's disease, dermatomyositis, Juvenile idiopathic arthritis, multiple sclerosis, Sjogren's syndrome, macrophage activation syndrome, and fibrotic diseases such as scleroderma.

In an embodiment, the present disclosure provides a method of treating a myeloid cell associated disease in a subject in need thereof, comprising administering to the subject (e.g., a human patient) an effective amount of a conjugate comprising an anti-human CD33 antibody conjugated to a therapeutic agent as disclosed herein e.g., a conjugate of Formula I, or a pharmaceutically acceptable or salt thereof. In certain embodiments, the myeloid cell associated disease is an immune disease, neurodegenerative disease, or cancer. In certain embodiments, the myeloid cell associated disease is an immune disease, for example, rheumatoid arthritis, systemic lupus erythematosus, lupus nephritis, cutaneous lupus, giant cell arteritis, polymyalgia rheumatica, psoriatic arthritis, atopic dermatitis, psoriasis, ulcerative colitis, Crohn's disease, dermatomyositis, Juvenile idiopathic arthritis, multiple sclerosis, Sjogren's syndrome, macrophage activation syndrome, or fibrotic diseases such as scleroderma. In an embodiment, the present disclosure further provides a method of treating rheumatoid arthritis in a subject in need thereof, comprising administering to the subject an effective amount of a conjugate of Formula I, or a pharmaceutically acceptable salt thereof. In an embodiment, the present disclosure further provides a method of treating systemic lupus erythematosus in a subject in need thereof, comprising administering to the subject an effective amount of a conjugate of Formula I, or a pharmaceutically acceptable salt thereof. In an embodiment, the present disclosure further provides a method of treating lupus nephritis in a subject in need thereof, comprising administering to the subject an effective amount of a conjugate of Formula I, or a pharmaceutically acceptable salt thereof. In an embodiment, the present disclosure further provides a method of treating cutaneous lupus in a subject in need thereof, comprising administering to the subject an effective amount of a conjugate of Formula I, or a pharmaceutically acceptable salt thereof. In an embodiment, the present disclosure further provides a method of treating giant cell arteritis in a subject in need thereof, comprising administering to the subject an effective amount of a conjugate of Formula I, or a pharmaceutically acceptable salt thereof. In an embodiment, the present disclosure further provides a method of treating polymyalgia rheumatica in a subject in need thereof, comprising administering to the subject an effective amount of a conjugate of Formula I, or a pharmaceutically acceptable salt thereof. In an embodiment, the present disclosure further provides a method of treating psoriatic arthritis in a subject in need thereof, comprising administering to the subject an effective amount of a conjugate of Formula I, or a pharmaceutically acceptable salt thereof. In an embodiment, the present disclosure further provides a method of treating atopic dermatitis in a subject in need thereof, comprising administering to the subject an effective amount of a conjugate of Formula I, or a pharmaceutically acceptable salt thereof. In an embodiment, the present disclosure further provides a method of treating psoriasis in a subject in need thereof, comprising administering to the subject an effective amount of a conjugate of Formula I, or a pharmaceutically acceptable salt thereof. In an embodiment, the present disclosure further provides a method of treating ulcerative colitis in a subject in need thereof, comprising administering to the subject an effective amount of a conjugate of Formula I, or a pharmaceutically acceptable salt thereof. In an embodiment, the present disclosure further provides a method of treating Crohn's disease in a subject in need thereof, comprising administering to the subject an effective amount of a conjugate of Formula I, or a pharmaceutically acceptable salt thereof. In an embodiment, the present disclosure further provides a method of treating dermatomyositis in a subject in need thereof, comprising administering to the subject an effective amount of a conjugate of Formula I, or a pharmaceutically acceptable salt thereof. In an embodiment, the present disclosure further provides a method of treating Juvenile idiopathic arthritis in a subject in need thereof, comprising administering to the subject an effective amount of a conjugate of Formula I, or a pharmaceutically acceptable salt thereof. In an embodiment, the present disclosure further provides a method of treating multiple sclerosis in a subject in need thereof, comprising administering to the subject an effective amount of a conjugate of Formula I, or a pharmaceutically acceptable salt thereof. In an embodiment, the present disclosure further provides a method of treating Sjogren's syndrome in a subject in need thereof, comprising administering to the subject an effective amount of a conjugate of Formula I, or a pharmaceutically acceptable salt thereof. In an embodiment, the present disclosure further provides a method of treating macrophage activation syndrome in a subject in need thereof, comprising administering to the subject an effective amount of a conjugate of Formula I, or a pharmaceutically acceptable salt thereof. In an embodiment, the present disclosure further provides a method of treating fibrotic diseases such as scleroderma in a subject in need thereof, comprising administering to the subject an effective amount of a conjugate of Formula I, or a pharmaceutically acceptable salt thereof. In some embodiments, the myeloid cell associated disease is a neurodegenerative disease (e.g., Alzheimer's Disease). In an embodiment, the present disclosure further provides a method of treating Alzheimer's Disease in a subject in need thereof, comprising administering to the subject an effective amount of a conjugate of Formula I, or a pharmaceutically acceptable salt thereof. In some embodiments the myeloid cell associated disease is a myeloid cell associated cancer (e.g., AML). In an embodiment, the present disclosure further provides a method of treating AML in a subject in need thereof, comprising administering to the subject an effective amount of a conjugate of Formula I, or a pharmaceutically acceptable salt thereof.

In an embodiment, the present disclosure further provides a conjugate comprising an anti-human CD33 antibody conjugated to a therapeutic agent as disclosed herein, e.g., a conjugate of Formula I, or a pharmaceutically acceptable salt thereof for use in therapy. In an embodiment, the present disclosure provides a conjugate comprising an anti-human CD33 antibody conjugated to a therapeutic agent as disclosed herein, e.g., a conjugate of Formula I, or a pharmaceutically acceptable salt thereof for use in the treatment of a myeloid cell associated disease. In certain embodiments, the myeloid cell associated disease is an immune disease, neurodegenerative disease, or cancer. In certain embodiments, the myeloid cell associated disease is an immune disease for example, rheumatoid arthritis, systemic lupus erythematosus, lupus nephritis, cutaneous lupus, giant cell arteritis, polymyalgia rheumatica, psoriatic arthritis, atopic dermatitis, psoriasis, ulcerative colitis, Crohn's disease, dermatomyositis, Juvenile idiopathic arthritis, multiple sclerosis, Sjogren's syndrome, macrophage activation syndrome, and fibrotic diseases such as scleroderma. In an embodiment, the present disclosure provides a conjugate of Formula I, or a pharmaceutically acceptable salt thereof, for use in the treatment of rheumatoid arthritis. In an embodiment, the present disclosure provides a conjugate of Formula I, or a pharmaceutically acceptable salt thereof, for use in the treatment of systemic lupus erythematosus. In an embodiment, the present disclosure provides a conjugate of Formula I, or a pharmaceutically acceptable salt thereof, for use in the treatment of lupus nephritis. In an embodiment, the present disclosure provides a conjugate of Formula I, or a pharmaceutically acceptable salt thereof, for use in the treatment of cutaneous lupus. In an embodiment, the present disclosure provides a conjugate of Formula I, or a pharmaceutically acceptable salt thereof, for use in the treatment of giant cell arteritis. In an embodiment, the present disclosure provides a conjugate of Formula I, or a pharmaceutically acceptable salt thereof, for use in the treatment of polymyalgia rheumatica. In an embodiment, the present disclosure provides a conjugate of Formula I, or a pharmaceutically acceptable salt thereof, for use in the treatment of psoriatic arthritis. In an embodiment, the present disclosure provides a conjugate of Formula I, or a pharmaceutically acceptable salt thereof, for use in the treatment of atopic dermatitis. In an embodiment, the present disclosure provides a conjugate of Formula I, or a pharmaceutically acceptable salt thereof, for use in the treatment of psoriasis. In an embodiment, the present disclosure provides a conjugate of Formula I, or a pharmaceutically acceptable salt thereof, for use in the treatment of ulcerative colitis. In an embodiment, the present disclosure provides a conjugate of Formula I, or a pharmaceutically acceptable salt thereof, for use in the treatment of Crohn's disease. In an embodiment, the present disclosure provides a conjugate of Formula I, or a pharmaceutically acceptable salt thereof, for use in the treatment of dermatomyositis. In an embodiment, the present disclosure provides a conjugate of Formula I, or a pharmaceutically acceptable salt thereof, for use in the treatment of Juvenile idiopathic arthritis. In an embodiment, the present disclosure provides a conjugate of Formula I, or a pharmaceutically acceptable salt thereof, for use in the treatment of multiple sclerosis. In an embodiment, the present disclosure provides a conjugate of Formula I, or a pharmaceutically acceptable salt thereof, for use in the treatment of Sjogren's syndrome. In an embodiment, the present disclosure provides a conjugate of Formula I, or a pharmaceutically acceptable salt thereof, for use in the treatment of macrophage activation syndrome. In an embodiment, the present disclosure provides a conjugate of Formula I, or a pharmaceutically acceptable salt thereof, for use in the treatment of fibrotic diseases such as scleroderma. In some embodiments, the myeloid cell associated disease is a neurodegenerative disease (e.g., Alzheimer's Disease). In an embodiment, the present disclosure provides a conjugate of Formula I, or a pharmaceutically acceptable salt thereof, for use in the treatment of Alzheimer's Disease. In some embodiments the myeloid cell associated disease is a myeloid cell associated cancer (e.g., AML). In an embodiment, the present disclosure provides a conjugate of Formula I, or a pharmaceutically acceptable salt thereof, for use in the treatment of AML.

In an embodiment, the present disclosure also provides the use of a conjugate comprising an anti-human CD33 antibody conjugated to a therapeutic agent as disclosed herein, e.g., a conjugate of Formula I, or a pharmaceutically acceptable salt thereof, for the manufacture of a medicament for the treatment of a myeloid cell associated disease. In certain embodiments, the myeloid cell associated disease is an immune disease, neurodegenerative disease, or cancer. In certain embodiments, the myeloid cell associated disease is an immune disease for example, rheumatoid arthritis, systemic lupus erythematosus, lupus nephritis, cutaneous lupus, giant cell arteritis, polymyalgia rheumatica, psoriatic arthritis, atopic dermatitis, psoriasis, ulcerative colitis, Crohn's disease, dermatomyositis, Juvenile idiopathic arthritis, multiple sclerosis, Sjogren's syndrome, macrophage activation syndrome, and fibrotic diseases such as scleroderma. In an embodiment, the present disclosure provides the use of a conjugate of Formula I, or a pharmaceutically acceptable salt thereof, for the manufacture of a medicament for the treatment of rheumatoid arthritis. In an embodiment, the present disclosure provides the use of a conjugate of Formula I, or a pharmaceutically acceptable salt thereof, for the manufacture of a medicament for the treatment of systemic lupus erythematosus, In an embodiment, the present disclosure provides the use of a conjugate of Formula I, or a pharmaceutically acceptable salt thereof, for the manufacture of a medicament for the treatment of lupus nephritis, In an embodiment, the present disclosure provides the use of a conjugate of Formula I, or a pharmaceutically acceptable salt thereof, for the manufacture of a medicament for the treatment of cutaneous lupus. In an embodiment, the present disclosure provides the use of a conjugate of Formula I, or a pharmaceutically acceptable salt thereof, for the manufacture of a medicament for the treatment of giant cell arteritis. In an embodiment, the present disclosure provides the use of a conjugate of Formula I, or a pharmaceutically acceptable salt thereof, for the manufacture of a medicament for the treatment of polymyalgia rheumatica. In an embodiment, the present disclosure provides the use of a conjugate of Formula I, or a pharmaceutically acceptable salt thereof, for the manufacture of a medicament for the treatment of psoriatic arthritis. In an embodiment, the present disclosure provides the use of a conjugate of Formula I, or a pharmaceutically acceptable salt thereof, for the manufacture of a medicament for the treatment of atopic dermatitis. In an embodiment, the present disclosure provides the use of a conjugate of Formula I, or a pharmaceutically acceptable salt thereof, for the manufacture of a medicament for the treatment of psoriasis. In an embodiment, the present disclosure provides the use of a conjugate of Formula I, or a pharmaceutically acceptable salt thereof, for the manufacture of a medicament for the treatment of ulcerative colitis. In an embodiment, the present disclosure provides the use of a conjugate of Formula I, or a pharmaceutically acceptable salt thereof, for the manufacture of a medicament for the treatment of Crohn's disease. In an embodiment, the present disclosure provides the use of a conjugate of Formula I, or a pharmaceutically acceptable salt thereof, for the manufacture of a medicament for the treatment of dermatomyositis. In an embodiment, the present disclosure provides the use of a conjugate of Formula I, or a pharmaceutically acceptable salt thereof, for the manufacture of a medicament for the treatment of Juvenile idiopathic arthritis. In an embodiment, the present disclosure provides the use of a conjugate of Formula I, or a pharmaceutically acceptable salt thereof, for the manufacture of a medicament for the treatment of multiple sclerosis. In an embodiment, the present disclosure provides the use of a conjugate of Formula I, or a pharmaceutically acceptable salt thereof, for the manufacture of a medicament for the treatment of Sjogren's syndrome. In an embodiment, the present disclosure provides the use of a conjugate of Formula I, or a pharmaceutically acceptable salt thereof, for the manufacture of a medicament for the treatment of macrophage activation syndrome. In an embodiment, the present disclosure provides the use of a conjugate of Formula I, or a pharmaceutically acceptable salt thereof, for the manufacture of a medicament for the treatment of fibrotic diseases such as scleroderma. In some embodiments, the myeloid cell associated disease is a neurodegenerative disease (e.g., Alzheimer's Disease). In an embodiment, the present disclosure provides the use of a conjugate of Formula I, or a pharmaceutically acceptable salt thereof, for the manufacture of a medicament for the treatment of Alzheimer's Disease. In some embodiments the myeloid cell associated disease is a myeloid cell associated cancer (e.g., AML). In an embodiment, the present disclosure provides the use of a conjugate of Formula I, or a pharmaceutically acceptable salt thereof, for the manufacture of a medicament for the treatment of AML.

The present disclosure provides a method of producing a conjugate, the method comprising conjugating a compound of the present disclosure with an anti-human CD33 antibody. The present disclosure provides a method of producing a conjugate, the method comprising conjugating a compound of the present disclosure with an anti-human CD33 antibody or antigen binding fragment thereof.

The present disclosure provides a method of producing a conjugate, the method comprising conjugating the compound of Formula IV with an anti-human CD33 antibody. The present disclosure provides a method of producing a conjugate, the method comprising conjugating the compound of Formula IVa with an anti-human CD33 antibody. The present disclosure provides a method of producing a conjugate, the method comprising conjugating the compound Formula IVb with an anti-human CD33 antibody. The present disclosure provides a method of producing a conjugate, the method comprising conjugating the compound Formula IVc with an anti-human CD33 antibody. The present disclosure provides a method of producing a conjugate, the method comprising conjugating the compound Formula IVd with an anti-human CD33 antibody.

In some embodiments, the conjugate being produced is the conjugate of Formula I.

The present disclosure provides a method of producing a conjugate, the method comprising the steps of:

(a) reducing an anti-human CD33 antibody with a reducing agent to produce a reduced anti-human CD33 antibody, wherein the anti-human CD33 antibody comprises one or more engineered cysteine residues;

(b) oxidizing the reduced anti-human CD33 antibody with an oxidizing agent to produce an oxidized anti-human CD33 antibody; and (c) contacting the oxidized anti-human CD33 antibody with a compound of the present disclosure to produce the conjugate.

The present disclosure provides a method of producing a conjugate, the method comprising the steps of:

(a) reducing an anti-human CD33 antibody with a reducing agent to produce a reduced anti-human CD33 antibody, wherein the anti-human CD33 antibody comprises one or more engineered cysteine residue;

(b) oxidizing the reduced anti-human CD33 antibody with an oxidizing agent to produce an oxidized anti-human CD33 antibody; and (c) contacting the oxidized anti-human CD33 antibody with a compound of the formula

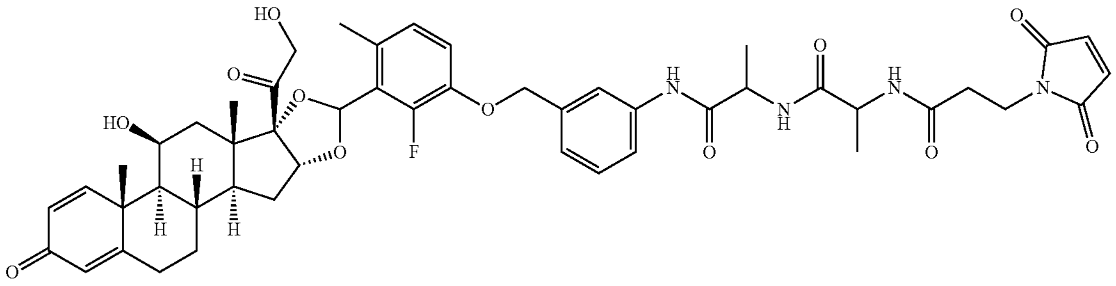

to produce the conjugate.

In some embodiments, the reducing agent is dithiothreitol. In some embodiments, the oxidizing agent is dehydroascorbic acid. In some embodiments, the reducing agent is dithiothreitol and the oxidizing agent is dehydroascorbic acid.

In an embodiment, the present disclosure further provides a pharmaceutical composition, comprising an anti-human CD33 antibody conjugated to a therapeutic agent as disclosed herein, or a pharmaceutically acceptable salt thereof, or an antibody, nucleic acid, or vector described herein with one or more pharmaceutically acceptable carriers, diluents, or excipients. In an embodiment, the present disclosure further provides a pharmaceutical composition, comprising a conjugate of Formula I, or a pharmaceutically acceptable salt thereof, with one or more pharmaceutically acceptable carriers, diluents, or excipients. In an embodiment, the present disclosure further provides a pharmaceutical composition, comprising a conjugate of Formula I with one or more pharmaceutically acceptable carriers, diluents, or excipients. In an embodiment, the present disclosure further provides a process for preparing a pharmaceutical composition, comprising admixing a conjugate of Formula I, or a pharmaceutically acceptable salt thereof, with one or more pharmaceutically acceptable carriers, diluents, or excipients. In an embodiment, the present disclosure also encompasses novel intermediates and processes for the synthesis of conjugates of Formula I.

DETAILED DESCRIPTION OF THE INVENTION

The term "CD33" or "CD33 receptor" as used herein, unless stated otherwise, refers to human myeloid cell surface antigen CD33 (also known as Sialic acid-binding Ig-like lectin 3, SIGLEC-3, SIGLEC3 FLJ00391, or p67) which belongs to the immunoglobulin superfamily sialic acid binding Ig-like lectin (SIGLEC) family. The term also includes naturally occurring variants of CD33, e.g., splice variants or allelic variants. The amino acid sequence of human CD33 is known in the art, e.g., NCBI Reference Sequence XP_011525833.1 (SEQ ID NO: 25). The amino acid sequence of cynomolgus monkey CD33 is known in the art, e.g., Sequence XP_045235686.1 (SEQ ID NO: 27). The term "CD33" is used herein to refer collectively to all known human CD33 isoforms and polymorphic forms.

The term "myeloid cell associated disease" as used herein refers to a disease associated with CD33 expressing myeloid cells. Such a myeloid cell associated disease may for example include immune diseases, neurodegenerative diseases, or myeloid cell associated cancer. The myeloid cell associated immune disease may be, for example, rheumatoid arthritis, systemic lupus erythematosus, lupus nephritis, cutaneous lupus, giant cell arteritis, polymyalgia rheumatica, psoriatic arthritis, atopic dermatitis, psoriasis, ulcerative colitis, Crohn's disease, dermatomyositis, Juvenile idiopathic arthritis, multiple sclerosis, Sjogren's syndrome, macrophage activation syndrome, or fibrotic diseases such as scleroderma. The myeloid cell associated neurodegenerative disease may be, for example, Alzheimer's Disease. The myeloid cell associated cancer may be, for example, acute myeloid leukemia (AML).

The term "antibody" as used herein, refers to an immunoglobulin molecule that binds an antigen. Embodiments of an antibody include a monoclonal antibody, polyclonal antibody, human antibody, humanized antibody, chimeric antibody, bispecific or multispecific antibody, or conjugated antibody. The antibodies can be of any class (e.g., IgG, IgE, IgM, IgD, IgA), and any subclass (e.g., IgG1, IgG2, IgG3, IgG4). Embodiments of the present disclosure also include antibody fragments or antigen binding fragments, the term "antibody fragments or antigen binding fragments" comprise at least a portion of an antibody retaining the ability to interact with an antigen such as for example, Fab, Fab', F(ab')2, Fv fragments, scFv, scFab, disulfide-linked Fvs (sdFv), a Fd fragment or linear antibodies, which may be for example, fused to an Fc region or an IgG heavy chain constant region.

An exemplary antibody is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. The heavy chain constant region refers to a region of an antibody, which comprises the Fc region and CH1 domain of the antibody heavy chain. Each light chain is comprised of a light chain variable region (VL) and a light chain constant region. The IgG isotype may be further divided into subclasses (e.g., IgG1, IgG2, IgG3, and IgG4). The numbering of the amino acid residues in the constant region is based on the EU index as in Kabat. Kabat et al, *Sequences of Proteins of Immunological Interest,* 5th edition, Bethesda, MD: U.S. Dept. of Health and Human Services, Public Health Service, National Institutes of Health (1991). The term EU Index numbering or EU numbering is used interchangeably herein.

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987)); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTies database available on at www.imgt.org; see Lefranc et al., Nucleic Acids Res. 1999; 27:209-212). The North CDR definitions are used for the exemplified anti-human CD33 antibodies as described herein.

Exemplary embodiments of antibodies of the present disclosure also include antibody fragments or antigen-binding fragments, which comprise at least a portion of an antibody retaining the ability to specifically interact with an antigen such as Fab, Fab', F(ab')2, Fv fragments, scFv, scFab, disulfide-linked Fvs (sdFv), a Fd fragment or linear antibodies, which may be for example, fused to an Fc region or an IgG heavy chain constant region.

The term "Fc region" as used herein, refers to a region of an antibody, which comprises the CH2 and CH3 domains of the antibody heavy chain. Optionally, the Fc region may include a portion of the hinge region or the entire hinge region of the antibody heavy chain. Biological activities such as effector function are attributable to the Fc region, which vary with the antibody isotype. Examples of antibody effector functions include, Fc receptor binding, antibody-dependent cell mediated cytotoxicity (ADCC), antibody-dependent cell mediated phagocytosis (ADCP), Clq binding, complement dependent cytotoxicity (CDC), phagocytosis, down regulation of cell surface receptors (e.g. B cell receptor), and B cell activation.

The term "Fc receptor" or "FcR" describes a receptor that binds to the Fc region of an antibody. In some embodiments, the FcR is a native sequence human FcR. An "Fc gamma receptor" or "FcγR" is an FcR that binds an IgG antibody and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have amino acid sequences that differ primarily in the cytoplasmic domains thereof. FcRs are reviewed in Ravetch and Kinet, *Ann. Rev. Immunol.,* 9:457-92 (1991); 25 Capel et al., Immunomethods, 4:25-34 (1994); and de Haas et al, *J. Lab. Clin. Med.,* 126:330-41 (1995).

The term "non-depleting antibody" as used herein refers to an antibody that does not significantly reduce CD33 expressing cell (e.g., myeloid cell) numbers in a subject after treatment, as compared to the myeloid cell numbers before the treatment. Myeloid cell number and viability can be measured using well-known assays such as trypan blue staining and Vi-cell counters. A non-depleting antibody typically does not induce antibody dependent cellular cytotoxicity (ADCC), antibody dependent cellular phagocytosis (ADCP), complement dependent cellular cytotoxicity (CDC), or apoptosis of the myeloid cells.

The term "receptor availability" as used herein, refers to the CD33 receptor expression on the cell surface. The CD33 cell surface receptor expression may refer to de novo expression of the CD33 receptor on the cell surface and/or CD33 receptor that is recycled to the cell surface after being internalized.

The term "non-degrading antibody" as used herein refers to an antibody that does not significantly reduce CD33 receptor expression on the cell surface and/or intracellular (internalized) CD33. A non-degrading CD33 antibody, for example as used herein does not significantly impact receptor availability.

The term, "modulates" and the like, as used herein, refers to altering or changing a measurable value and includes both altering or changing such a measurable value upwards (i.e., upmodulate or upmodulating) or downwards (i.e., downmodulate or downmodulating).

The terms "bind" and "binds" as used herein, are intended to mean, unless indicated otherwise, the ability of a protein or molecule to form a chemical bond or attractive interaction with another protein or molecule, which results in proximity of the two proteins or molecules as determined by common methods known in the art.

The term "therapeutic agent" as used herein, refers to therapeutic compositions, such as an anti-inflammatory agent, glucocorticoid, cytotoxic agent, siRNA, saRNA, peptide, oligonucleotide, small molecule, nanoparticle, lipid nanoparticle, exosome, antibody, or fragment thereof, or a combination thereof which can be conjugated to the anti-human CD33 antibodies as disclosed herein to form a conjugate (e.g., an antibody drug conjugate). In some embodiments, such conjugates elicit immunomodulatory or other therapeutic effects for the treatment of myeloid cell associated diseases by specific targeting of the CD33 receptor on the myeloid cells by the anti-human CD33 antibodies as disclosed herein and subsequent delivery of the therapeutic agent into the myeloid cell.

Furthermore, therapeutic agents may be conjugated to the anti-human CD33 antibodies as disclosed herein in a variety of ways and at various positions or portions of the antibody such that such linkage does not interfere with the binding of the antibody to the CD33 receptor, and does not interfere with the therapeutic properties of the therapeutic agent when conjugated. The terms "linked" and "conjugated", as used interchangeably herein, refers to a first molecule or compound, for example an antibody or fragment thereof, being associated, attached, connected, covalently linked or connected, or otherwise joined to a second molecule or compound, for example a therapeutic agent as described herein.

The terms "nucleic acid" as used herein, refer to polymers of nucleotides, including single-stranded and/or double-stranded nucleotide-containing molecules, such as DNA, cDNA, and RNA molecules, incorporating native, modified, and/or analogs of, nucleotides. Polynucleotides of the present disclosure may also include substrates incorporated therein, for example, by DNA or RNA polymerase or a synthetic reaction.

Embodiments of the present disclosure include conjugates where a polypeptide (e.g., anti-human CD33 antibody) is conjugated to one or more drug moieties, such as 2 drug moieties, 3 drug moieties, 4 drug moieties, 5 drug moieties, or more drug moieties. The drug moieties may be conjugated to the polypeptide at one or more sites in the polypeptide, as described herein. In certain embodiments, the conjugates have an average drug-to-antibody ratio (DAR) (molar ratio) in the range of from 2 to 5, or from 3 to 5, or from 3 to 4. In certain embodiments, the conjugates have an average DAR from 3 to 4. In certain embodiments, the conjugates have an average DAR of about 3. In certain embodiments, the conjugates have an average DAR of about 4.

As used herein, it is understood by one of skill in the art that the conjugate of Formula I can also be referred to as anti-human CD33 antibody glucocorticoid conjugates ("anti-human CD33 Ab GC conjugates").

The anti-human CD33 conjugates, e.g., the anti-human CD33 antibody GC conjugates of the present disclosure can be formulated as pharmaceutical compositions administered by any route which makes the conjugate bioavailable including, for example, intravenous or subcutaneous administration. Such pharmaceutical compositions can be prepared using techniques and methods known in the art (See, e.g., Remington: The Science and Practice of Pharmacy, A. Adejare, Editor, $23^{rd}$ Edition, published 2020, Elsevier Science).

As used herein, the terms "treating", "treatment", or "to treat" includes restraining, slowing, stopping, controlling, delaying, or reversing the progression or severity of an existing symptom or disorder, or ameliorating the existing symptom or disorder, but does not necessarily indicate a total elimination of the existing symptom or disorder. Treatment includes administration of a protein or nucleic acid or vector or composition for treatment of a symptom or disorder in a patient, particularly in a human.

The term "inhibits" or "inhibiting" as used herein, refers to for example, a reduction, lowering, slowing, decreasing, stopping, disrupting, abrogating, antagonizing, or blocking of a biological response or activity, but does not necessarily indicate a total elimination of a biological response.

As used herein, the term "subject" refers to a mammal, including, but are not limited to, a human, chimpanzee, ape, monkey, cattle, horse, sheep, goat, swine, rabbit, dog, cat, rat, mouse, guinea pig, and the like. Preferably the subject is a human.

As used herein, the term "effective amount" refers to the amount or dose of conjugate of the disclosure, or a pharmaceutically acceptable salt thereof which, upon single or multiple dose administration to the subject, provides the desired effect in the subject under diagnosis or treatment. The term "effective amount", as used herein, further refers to an amount or dose of conjugates of the disclosure, or a pharmaceutically acceptable salt thereof, that will elicit the desired biological or medical response of a subject, for example, reduction or inhibition of a protein activity, or ameliorate symptoms, alleviate conditions, slow or delay disease progression, or prevent a disease, etc. In a non-limiting embodiment, the term "effective amount" refers to the amount necessary (at dosages and for periods of time and for the means of administration) of or dose of conjugate of the disclosure, or a pharmaceutically acceptable salt thereof, when administered to a subject, is effective to at least partially alleviate, inhibit, prevent, and/or ameliorate a condition, or a disorder, or a disease, to achieve the desired therapeutic result. An effective amount is also one in which any toxic or detrimental effects of or dose of conjugate of the disclosure, or a pharmaceutically acceptable salt thereof of the present disclosure are outweighed by the beneficial effects.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular conjugate administered; the mode of administration; the bioavailability characteristics of the preparation administered; the dose regimen selected; the use of concomitant medication; and other relevant circumstances.

Included within the scope of the present invention is a pharmaceutically acceptable salt of the conjugate of Formula I. A pharmaceutically acceptable salt of a conjugate of the invention, such as a conjugate of Formula I can be formed under standard conditions known in the art. See, for example, Berge, S. M., et al., "Pharmaceutical Salts," *Journal of Pharmaceutical Sciences,* 66: 1-19, (1977).

TABLE 1

Abbreviations and definitions

| Term | Definition |
|---|---|
| ACN | acetonitrile |
| aq | aqueous |
| cP | centipoise |
| DCM | dichloromethane |
| DIPEA | N,N-diisopropylethylamine |
| DMF | N,N-dimethylformamide |
| DMSO | dimethyl sulfoxide |
| dppf | 1,1'-bis(diphenylphosphino)ferrocene |
| ES/MS | electrospray mass spectrometry |
| EtOAc | ethyl acetate |
| HATU | hexafluorophosphate azabenzotriazole tetramethyl uronium |
| HPLC | high performance liquid chromatography |
| LDA | lithium diisopropylamide |
| MeOH | methanol |
| MS | mass spectrometry |
| MTBE | methyl tert-butyl ether |
| m/z | mass-to-charge ratio |
| NMR | nuclear magnetic resonance |
| Pet ether | petroleum ether |
| rt | room temperature |
| satd | saturated |
| THF | tetrahydrofuran |

The conjugates of the present disclosure, or salts thereof, may be readily prepared by a variety of procedures known to one of ordinary skill in the art, some of which are illustrated in the preparations and examples below. One of ordinary skill in the art recognizes that the specific synthetic steps for each of the routes described may be combined in different ways, or in conjunction with steps from different schemes, to prepare conjugates of the disclosure, or salts thereof. The product of each step can be recovered by conventional methods well known in the art, including extraction, evaporation, precipitation, chromatography, filtration, trituration, and crystallization. All substituents unless otherwise indicated, are as previously defined. The reagents and starting materials are readily available to one of ordinary skill in the art. The following preparations, examples, and assays further illustrate the invention, but should not be construed to limit the scope of the invention in any way.

Preparation 1

6-Bromo-2-Fluoro-3-Methoxybenzaldehyde

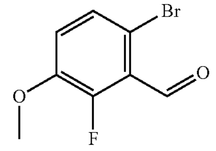

Figure 1A:
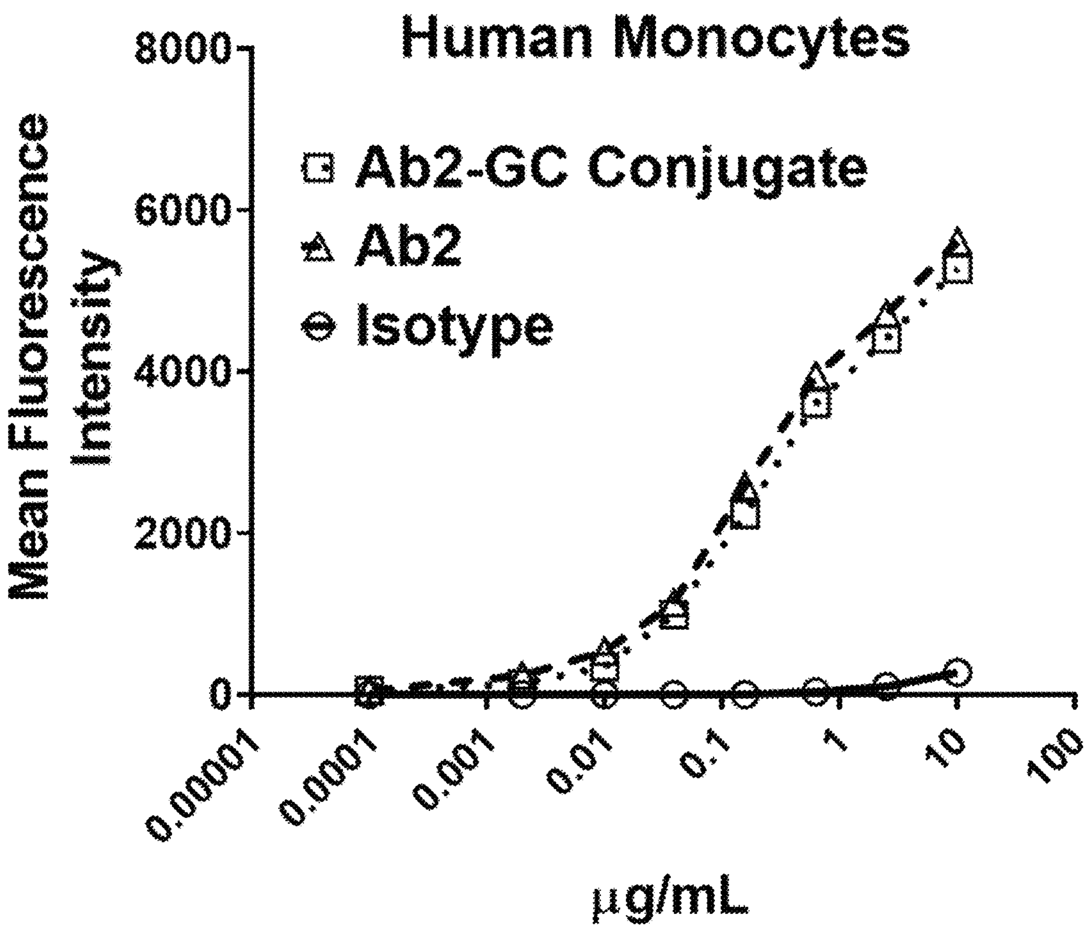
FIGS. 1A-1B show the anti-human CD33 Ab2 and Ab2 GC conjugate of Example 1b (1A) and Ab3 (1B) bound to cell surface CD33 on human monocytes in a fluorescence activated cell sorting (FACS) assay.

Two reactions were carried out in parallel. To a solution of 4-bromo-2-fluoro-1-methoxybenzene (250 g, 1.2 mol) in THF (1500 mL) was added LDA (2 M, 730 mL) slowly at −78° C., over 30 min. After an additional 30 min, DMF (140 mL, 1.8 mol) was added at −78° C. slowly over 30 min. After 1 h, the two reactions were combined, and the mixture was diluted with aq citric acid (2000 mL) and extracted with EtOAc (1500 mL×2). The combined organic layers were washed with satd aq NaCl (1000 mL) and concentrated under reduced pressure to give a residue. The residue was triturated with petroleum ether (1000 mL) at rt over 12 h to give the title compound (382 g, 67% yield). ES/MS m/z 233.9 (M+H).

Preparation 2

2-Fluoro-3-methoxy-6-methylbenzaldehyde

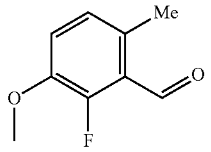

Three reactions were carried out in parallel. 6-Bromo-2-fluoro-3-methoxybenzaldehyde (120 g, 5.3 mol), methylboronic acid (47 g, 7.9 mol), $Pd(dppf)Cl_2$ (12 g, 0.02 mol), and $Cs_2CO_3$ (340 g, 1.1 mol) were added to a mixture of 1,4-dioxane (600 mL) and water (120 mL). The mixture was stirred at 120° C. After 12 h, the three reactions were combined, and the mixture was diluted with satd aq $NH_4Cl$ (1000 mL) and extracted with MTBE (1500 mL×2). The combined organic layers were washed with satd aq NaCl (1000 mL) and concentrated under reduced pressure to give a residue. The residue was purified by silica gel chromatography, eluting with 40:1 Pet ether: EtOAc to give the title compound (180 g, 59%). ES/MS m/z 169.3 (M+H).

Preparation 3

2-Fluoro-3-hydroxy-6-methylbenzaldehyde

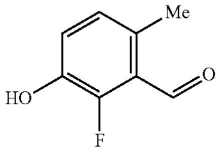 [SMILES: Cc1ccc(O)c(F)c1C=O]

2-Fluoro-3-methoxy-6-methylbenzaldehyde (175 g, 1.0 mol) was added into DCM (1050 mL). $BBr_3$ (200 mL, 2.1 mol) was added slowly into the solution at 0° C. The reaction was stirred at rt. After 1 h, the mixture was diluted with satd aq $NaHCO_3$ (1000 mL) until pH=7-8 and then extracted with MTBE (1500 mL×2). The combined organic layers were washed with satd aq NaCl (1000 mL) and concentrated under reduced pressure to give the title compound (110 g, 68%). ES/MS m/z 154.9 (M+H).

Preparation 4 tert-Butyl N-[3-[(2-fluoro-3-formyl-4-methyl-phenoxy)methyl]phenyl]carbamate

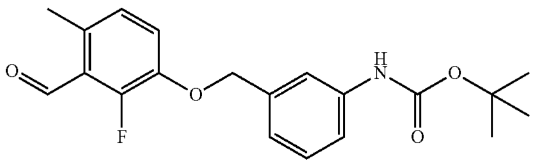 [SMILES: Cc1ccc(OCc2cccc(NC(=O)OC(C)(C)C)c2)c(F)c1C=O]

2-Fluoro-3-hydroxy-6-methylbenzaldehyde (130 g, 0.84 mol), tert-butyl (3-(bromomethyl)phenyl)carbamate (200 g, 0.70 mol), and potassium carbonate (350 g, 2.5 mol) were added in acetonitrile (780 mL) at rt and then heated to 50° C. After 5 h, the reaction was diluted with water (600 mL) and extracted with EtOAc (800 mL×2). The combined organic layers were washed with satd aq NaCl (800 mL) and concentrated under reduced pressure to give a residue. The residue was purified by silica gel chromatography, eluting with 50:1 Pet ether: EtOAc to give the crude product. The crude product was triturated with MTBE (500 mL) at rt for 30 min to give the title compound (103 g, 32%). ES/MS m/z 382.1 ($M+Na^+$).

Preparation 5

(6aR,6bS,7S,8aS,8bS,10R,11aR,12aS,12bS)-10-(3-((3-Aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

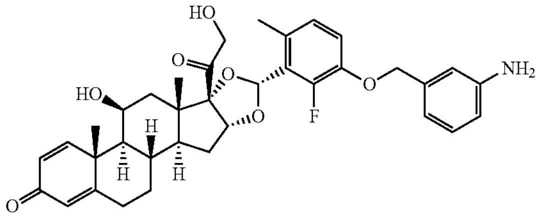

Perchloric acid (70% in water, 4.8 mL) was added to a suspension of (8S,9S,10R,11S,13S,14S,16R,17S)-11,16,17-trihydroxy-17-(2-hydroxyacetyl)-10,13-dimethyl-7,8,9,11,12,14,15,16-octahydro-6H-cyclopenta[a]phenanthren-3-one (4.4 g, 12 mmol, also referred to as "16alpha-hydroxyprednisolone") and tert-butyl N-[3-[(2-fluoro-3-formyl-4-methyl-phenoxy)methyl]phenyl]carbamate (4.0 g, 11 mmol, preparation 4) in acetonitrile (110 mL) at −10° C. and was warmed to rt. After 1 h, DMF (10 mL) was added to the suspension at rt. After 18 h, the reaction was quenched with satd aq $NaHCO_3$ and extracted with 9:1 DCM: isopropanol. The organic layers were combined, dried over $MgSO_4$, filtered, and concentrated under reduced pressure to give a residue. The residue was purified by reverse phase chromatography, eluting with 1:1 aq $NH_4HCO_3$ (10 mM+5% MeOH): ACN to give the title compound, peak 1 (1.72 g, 25%). ES/MS m/z 618.6 (M+H). $^1H$ NMR (400.13 MHz, DMSO-$d_6$) δ0.93-0.87 (m, 6H), 1.40 (s, 3H), 1.71-1.60 (m, 1H), 1.89-1.76 (m, 4H), 2.18-2.12 (m, 2H), 2.29 (s, 4H), 4.23-4.17 (m, 1H), 4.32-4.30 (m, 1H), 4.50-4.43 (m, 1H), 4.81 (d, J=3.2 Hz, 1H), 4.98-4.95 (m, 3H), 5.16-5.10 (m, 3H), 5.61 (s, 1H), 5.95 (s, 1H), 6.18-6.15 (m, 1H), 6.53-6.48 (m, 2H), 6.58 (s, 1H), 6.90-6.86 (m, 1H), 6.99 (t, J=7.7 Hz, 1H), 7.12 (t, J=8.5 Hz, 1H), 7.33-7.30 (m, 1H).

Preparation 6

(6aR,6bS,7S,8aS,8bS,10S,11aR,12aS,12bS)-10-(3-((3-Aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (herein also referred to as "GC1")

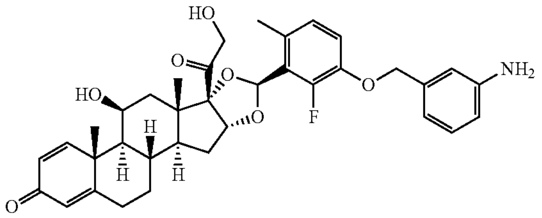

From Preparation 5, the residue was purified by reverse phase chromatography, eluting with 1:1 aq $NH_4HCO_3$ (10 mM+5% MeOH): ACN to give the title compound, peak 2 (1.24 g, 18%). ES/MS m/z 618.6 (M+H). $^1H$ NMR (400.13 MHz, $d_6$-DMSO) δ0.88 (s, 3H), 1.24-1.12 (m, 2H), 1.40 (s, 3H), 1.69-1.56 (m, 1H), 1.91-1.76 (m, 4H), 2.08-2.01 (m, 2H), 2.22 (s, 3H), 2.39-2.29 (m, 1H), 3.18 (d, J=5.2 Hz, 1H), 4.12-4.00 (m, 1H), 4.37-4.30 (m, 2H), 4.79 (d, J=3.1 Hz, 1H), 5.00-4.93 (m, 2H), 5.10-5.06 (m, 3H), 5.31 (d, J=6.7 Hz, 1H), 5.95 (s, 1H), 6.18 (dd, J=1.8, 10.1 Hz, 1H), 6.34 (s, 1H), 6.53-6.48 (m, 2H), 6.58 (s, 1H), 6.87 (d, J=8.5 Hz, 1H), 6.99 (t, J=7.7 Hz, 1H), 7.09 (t, J=8.5 Hz, 1H), 7.33 (d, J=10.1 Hz, 1H).

Preparation 7

(3-(2,5-Dioxo-2,5-dihydro-1H-pyrrol-1-yl)propanoyl)-L-alanyl-L-alanine

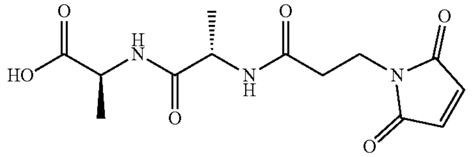 [SMILES: C[C@H](NC(=O)[C@H](C)NC(=O)CCN1C(=O)C=CC1=O)C(=O)O]

To a solution of N-succinimidyl 3-maleimidopropionate (5.0 g, 19 mmol) and L-alanyl-L-alanine (3.4 g, 21 mmol) in DMF (25 mL) was added DIPEA (3.1 mL, 18 mmol) and the mixture was stirred at rt overnight. The reaction mixture was concentrated under reduced pressure to give a residue, which was purified by silica gel chromatography eluting with 2% acetic acid in EtOAc to give the title compound (4.0 g, 69%). ES/MS m/z 312.3 (M+H).

Preparation 8

3-(2,5-Dioxo-2,5-dihydro-1H-pyrrol-1-yl)-N—((S)-1-(((S)-1-((3-((2-fluoro-3-((6aR,6bS,7S,8aS,8bS,10S,11aR,12a5,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)-4-methylphenoxy)methyl)phenyl)amino)-1-oxopropan-2-yl)amino)-1-oxopropan-2-yl)propanamide (herein also referred to as "GC-L")

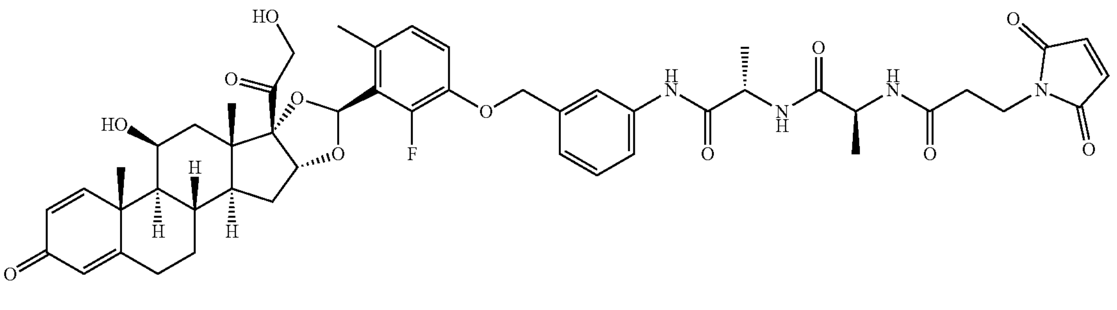

To a solution of (6aR,6bS,7S,8aS,8bS,10S,11aR,12aS,12bS)-10-(3-((3-aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',K4,5]indeno[1,2-d][1,3]dioxol-4-one (24 g, 39 mmol, see Preparation 6) and 3-(2,5-dioxo-2,5-dihydro-1H-pyrrol-1-yl)propanoyl)-L-alanyl-L-alanine (15 g, 47 mmol, see Preparation 7) in DMF (250 mL), cooled to 0-5° C., was added 2,6-lutidine (11 mL, 97 mmol) followed by HATU (17 g, 43 mmol). The mixture was stirred at 0-5° C. for 5 min, then the cooling bath was removed, and the mixture was stirred for 2 h. The mixture was diluted with EtOAc. The organic solution was washed with three portions water, one portion satd aq NaCl, dried over $Na_2SO_4$ (MeOH added to aid solubility), filtered and evaporated to give the crude product. The crude product was purified by silica gel chromatography using a gradient of 1-10% MeOH in DCM to give the title compound (24 g, 68%). ES/MS m/z 911.4 (M+H). $^1$H NMR (400.13 MHz, DMSO): δ 9.88 (s, 1H), 8.20 (d, J=7.1 Hz, 1H), 8.11 (d, J=7.2 Hz, 1H), 7.68 (s, 1H), 7.60-7.58 (m, 1H), 7.34-7.29 (m, 2H), 7.14-7.09 (m, 2H), 7.00 (s, 2H), 6.89 (d, J=8.4 Hz, 1H), 6.34 (s, 1H), 6.18 (dd, J=1.8, 10.0 Hz, 1H), 5.95 (s, 1H), 5.76 (s, 1H), 5.31 (d, J=6.8 Hz, 1H), 5.13-5.04 (m, 3H), 4.78 (d, J=3.1 Hz, 1H), 4.41-4.30 (m, 4H), 4.10-4.00 (m, 1H), 3.61 (t, J=7.3 Hz, 2H), 2.42-2.31 (m, 3H), 2.22 (s, 3H), 2.11-2.01 (m, 2H), 1.91-1.78 (m, 5H), 1.40 (s, 3H), 1.31 (d, J=7.2 Hz, 3H), 1.19-1.11 (m, 5H), 0.88 (s, 3H).

Preparation 9

3-(2,5-dioxo-2,5-dihydro-1H-pyrrol-1-yl)-N—((S)-1-(((S)-1-((3-((2-fluoro-3-((6aR,6bS,7S,8aS,8bS,10R,11aR,12a5,12b5)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)-4-methylphenoxy)methyl)phenyl)amino)-1-oxopropan-2-yl)amino)-1-oxopropan-2-yl)propanamide

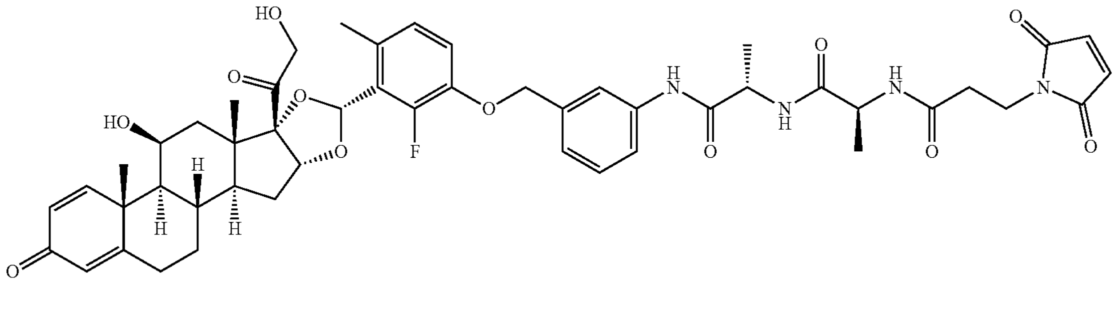

In a manner analogous to the procedure described in Preparation 8, the compound of Preparation 9 was prepared from (6aR,6bS,7S,8aS,8bS,10R,11aR,12aS,12bS)-10-(3-((3-aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (see Preparation 5) and 3-(2,5-dioxo-2,5-dihydro-1H-pyrrol-1-yl)propanoyl)-L-alanyl-L-alanine (see Preparation 7). ES/MS m/z 911.4 (M+H). $^1$HNMR (500.11 MHz, DMSO): δ9.88 (s, 1H), 8.23-8.20 (m, 1H), 8.11 (d, J=7.2 Hz, 1H), 7.69 (s, 1H), 7.59 (d, J=8.0 Hz, 1H), 7.33-7.28 (m, 2H), 7.15-7.08 (m, 2H), 7.00 (s, 2H), 6.91-6.89 (m, 1H), 6.17 (dd, J=1.7, 10.1 Hz, 1H), 5.94 (s,1H), 5.61 (s, 1H), 5.16-5.12 (m, 3H), 4.98-4.96 (m, 1H), 4.81 (d, J=3.1 Hz, 1H), 4.49-4.36 (m, 6H), 3.61 (t, J=7.3 Hz, 2H), 2.41 (t, J=7.3 Hz, 2H), 2.30-2.29 (m, 4H), 2.17-2.15 (m, 2H), 1.88-1.77 (m, 4H), 1.69-1.61 (m, 1H), 1.40 (s, 3H), 1.31 (d, J=7.2 Hz, 3H), 1.18 (d, J=7.2 Hz, 3H), 0.93-0.87 (m, 6H).

EXAMPLES

Example 1. Generation of the Exemplified Anti-human CD33 Antibody GC Conjugates

Example 1a: Generation and Engineering of Anti-human CD33 Antibodies

Antibody generation: The anti-human CD33 antibodies as described herein, were discovered from a phage display Fab library using solution panning against Fc-tagged extracellular domain of human CD33 (hCD33-Fc). Briefly, the library was first panned against human IgG Fc to remove Fc binders. Human CD33 specific binders were enriched after 3 rounds of panning and identified by single-point phage ELISA screen against his-tagged hCD33. Following conversion into IgG format and purification, antibodies binding to CD33-expressing myeloid cells was confirmed by Fluorescence Activated Cell Sorting (FACS) assay using human and cynomolgus monkey PBMC, respectively.

Antibodies generated from the above processes were screened for internalization activity on CD33-expressing myeloid cells. Antibodies were labelled with pHrodo™ Red, incubated with human PBMC and analyzed by FACS. pHrodo-labeled antibody produces red fluorescence signal in low pH environment after being internalized into the lysosome. Antibodies were selected for specific binding to both human and cynomolgus CD33 on myeloid cells and high efficiency of internalization.

Engineering of anti-human CD33 Antibodies: Significant engineering, including antibody sequence germlining, affinity maturation, amino acid modifications, and developability studies were conducted to generate the anti-human CD33 antibodies as described herein. The engineering overcame challenges to achieve and balance desirable affinity to human and cynomolgus monkey CD33, and improve functional characteristics of the antibodies (e.g., reduce receptor degradation and cell depletion properties), improve immunogenicity risk profile, viscosity, and developability for subcutaneous administration.

VH and Vic sequences of the anti-human CD33 antibodies as described herein are highly homologous to human germlines. Four framework residues were identified in the light chain framework region of the parental antibody (A12, S18, S22 and A40 (Kabat numbering) and were converted to germline residues without impacting specificity and affinity to human CD33, resulting in the Antibody (Ab1) having high percentage of human germline identity, which potentially reduces immunogenicity risk, thus providing an improved developability profile.

Ab1 was further engineered as a Fab using a phage expression platform technology (Anal Biochem. 1998 256 (2):169-77). Amino acid residue substitution at HCDR3 E95T (Kabat numbering) was found to be critical in improving affinity for human CD33, decreasing interaction to Ig-coupled chromatography column, and improving viscosity of the antibody at high concentrations. Additionally, the HCDR3 E95T and the LCDR1 D28P residue substitutions were identified and engineered to improve isoelectric point of the anti-human CD33 antibody GC conjugate.

Ab1 demonstrated significant difference in affinity to human CD33 (3.4E-09) and cynomolgus monkey CD33 (2.41E-05) (see Table 4). Over a 10-fold affinity difference can make preclinical toxicology studies and data interpretation challenging. Using Ab1 as a template, using antibody structure information, CDR mutation scanning, and computational modeling of cynomolgus monkey CD33 extracellular domain (ECD), a targeted mutagenesis library was designed to screen for mutations to improve affinity to cynomolgus monkey CD33. Four amino acid residues in the LCDR1 (D28, V29, F30 and R31 (Kabat numbering) were identified as critical for increasing cynomolgus monkey CD33 binding while maintaining desirable binding affinity to human CD33. The combination of the HCDR3 E95T amino acid residue substitution and the 4 LCDR1 amino acid residue substitutions as identified above significantly improved binding affinity to cynomolgus monkey CD33 (see Table 4) and significantly minimized the affinity difference between the human and cynomolgus monkey CD33 while maintaining desirable binding affinity to human CD33. Combination of these engineered residues resulted in generation of Ab2 and Ab3 (Table 2a, 2b, and 3).

Selection of the backbone: Antibody amino acid residue substitutions L234A, L235A and P329A (EU numbering) were incorporated in the IgG1 Fc region (IgG1AAA), which attenuated binding of the antibodies to Fcγ receptors and C1q and consequently the effector function activities such as ADCC and CDC. Furthermore, the IgG1AAA backbone significantly reduced the degradation of the CD33 receptor by the CD33 antibodies as shown below.

The antibody further comprises amino acid residue substitutions S124C and A378C (EU numbering) in the IgG1 HC constant region, for specific conjugation to a therapeutic agent (e.g., a glucocorticoid).

The amino acid sequence of human CD33 ECD is provided by SEQ ID NO: 28, the amino acid sequence of cynomolgus monkey CD33 ECD is provided by SEQ ID NO: 29.

TABLE 2a

CDR amino acid sequences of exemplified anti-human CD33 antibodies

| | CDR Sequence | | | | | |
|---|---|---|---|---|---|---|
| | HCDR1 | HCDR2 | HCDR3 | LCDR1 | LCDR2 | LCDR3 |
| Ab1 | SEQ ID NO: 1 | SEQ ID NO: 2 | SEQ ID NO: 17 | SEQ ID NO: 18 | SEQ ID NO: 5 | SEQ ID NO: 6 |
| Ab2 | SEQ ID NO: 1 | SEQ ID NO: 2 | SEQ ID NO: 3 | SEQ ID NO: 4 | SEQ ID NO: 5 | SEQ ID NO: 6 |
| Ab3 | SEQ ID NO: 1 | SEQ ID NO: 2 | SEQ ID NO: 3 | SEQ ID NO: 13 | SEQ ID NO: 5 | SEQ ID NO: 6 |

TABLE 2b

CDR amino acid consensus sequences of exemplified anti-human CD33 antibodies

| CDR | Consensus sequence |
|---|---|
| LCDR1 | SEQ ID NO: 26<br>QASQPTXaa$_7$Xaa$_8$IYLN<br>wherein Xaa$_7$ is Phenylalanine or Tyrosine, and Xaa$_8$ is Asparagine or Isoleucine |

TABLE 3

| Amino acid sequences of exemplified anti-human CD33 antibodies | | | | |
|---|---|---|---|---|
| | VH | VL | HC | LC |
| Ab1 | SEQ ID NO: 19 | SEQ ID NO: 20 | SEQ ID NO: 21 | SEQ ID NO: 22 |
| Ab2 | SEQ ID NO: 7 | SEQ ID NO: 8 | SEQ ID NO: 9 | SEQ ID NO: 10 |
| Ab3 | SEQ ID NO: 7 | SEQ ID NO: 14 | SEQ ID NO: 9 | SEQ ID NO: 15 |

Example 1b: Generation of Anti-human CD33 Ab2 GC Conjugate Wherein n is 4

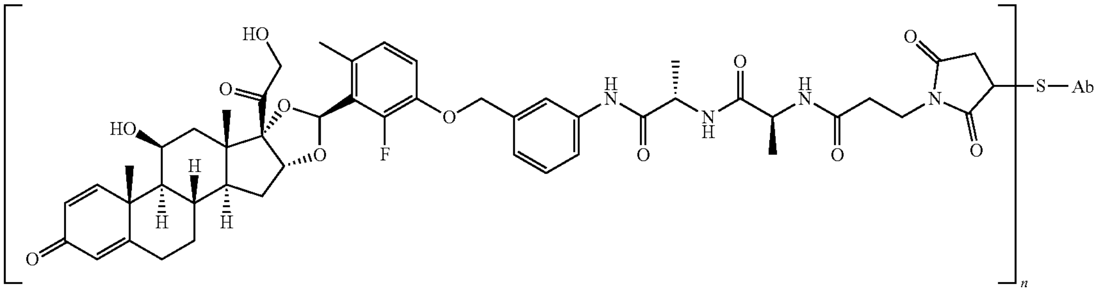

wherein n is 4; and

Ab is Ab2.

The exemplified anti-human CD33 antibody Ab2 (see Table 2 and Table 3) was first reduced in the presence of 40-fold molar excess of dithiothreitol (DTT) for 2 hours at 37° C. or >16 hours at ~21° C. This initial reduction step was used to remove the various capping groups, including cysteine and glutathione which are bound to the engineered cysteine at the 124 and 378 position of the heavy chain during expression. Following the reduction step, the sample was purified through a desalting column to remove the unbound caps as well as the reducing agent. A subsequent 2-hour oxidation step was carried out at room temperature (~21° C.) in the presence of 10-fold molar excess of dehydroascorbic acid (DHAA) to reform the native interchain disulfides between the light chain and heavy chain as well as the pair of hinge disulfides. After the 2-hour oxidation step, 4-8 molar equivalents of the glucocorticoid receptor agonist payload-linker ("GC-L"), 3-(2,5-dioxo-2,5-dihydro-1H-pyrrol-1-yl)-N—((S)-1-(((S)-1-((3-((2-fluoro-3-((6aR,6bS,7S,8aS,8bS,10S,11aR,12a5,12b5)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)-4-methylphenoxy)methyl)phenyl)amino)-1-oxopropan-2-yl)amino)-1-oxopropan-2-yl)propanamide prepared in Preparation 8, was added using a 10 mM stock solution solubilized in DMSO. The sample was then incubated at room temperature for 30-60 minutes to allow for efficient conjugation of the GC-L to the engineered cysteines. A subsequent polishing step, such as Size Exclusion Chromatography (SEC) or Tangential Flow Filtration (TFF) was then used to buffer exchange the samples into an appropriate formulation buffer and to remove DMSO and any excess linker-payload.

Drug to antibody ratio (DAR) assessment: To assess the average number of linker-payloads present on the final conjugates, two analytical methods were used: 1) Reverse phase (RP) HPLC and 2) Time of Flight (TOF) mass spectrometry. Both methods required an initial sample reduction step, which included the additional of dithiothreitol (DTT) to a final concentration of ~10 mM, followed by a 5-minute incubation at 42° C.

Reverse Phase HPLC Method: 10 to 30 μg of the reduced anti-human CD33 antibody Ab2 GC conjugate sample was injected onto a Phenyl SPW, 4.6 mm×7.5 cm, 10 μm column (Tosh Part#0008043). The A buffer was made up of 0.1% trifluoroacetic acid (TFA) in water while B buffer was comprised of 0.1% trifluoroacetic acid (TFA) in acetonitrile (ACN). The column was equilibrated in 20% B buffer prior to sample injection followed by a gradient from 28% B to 40% B over ~8.5 column volumes. The average DAR was determined by calculating the contribution from each individual DAR species from the fractional percentage multiplied by the DAR number for each contributing species. As this value is based on a partially reduced sample and only represents half of the molecule, the number was then multiplied by 2 to account for an intact antibody GC conjugate. DAR calculations for the exemplified anti-human CD33 Ab2 GC conjugate of Example 1b are provided in Table 4.

TABLE 4

| Quantification of the average DAR for exemplified anti-human CD33 Ab2 GC conjugate using fractional percentages for each DAR species from a partially reduced sample. | | |
|---|---|---|
| DAR | Peak % | DAR Contribution |
| 0 | 23.6 | 0.00 |
| 1 | 0.75 | 0.03 |
| Total LC % | 24.35 | 0.03 |
| | LC Avg DAR | 0.03 (DAR contribution from LC) |
| 0 | 0.33 | 0.00 |
| 1 | 19.5 | 0.26 |
| 2 | 41.07 | 1.09 |
| 3 | 14.76 | 0.59 |
| 4 | | |
| Total HC % | 75.66 | |
| | HC Avg DAR | 1.93 (DAR contribution from HC) |
| (HC + LC)2 | Final Avg DAR | 3.92 |

Time of Flight Mass Spectrometry Method: 8 μg of the partially reduced sample was injected onto a Poroshell 300sb-C3 2.1×12.5 mm, 5 μm column (Agilent Part#821075-924). Buffer A was made up of 0.1% trifluoroacetic acid (TFA) in water while buffer B comprised of 0.1% trifluoroacetic acid (TFA) in acetonitrile (ACN). The column was equilibrated in 0% B buffer prior to sample injection followed by a gradient from 10% B to 80% B over ~28 column volumes. The average DAR was determined by calculating the contribution from each individual DAR species from the fractional percentage multiplied by the DAR number for each contributing species. As this value is based on a partially reduced sample and only represents half of the molecule, the number was then multiplied by 2 to account for an intact antibody GC conjugate. DAR calculations for the anti-human CD33 Ab2 GC conjugate of Example 1b are provided in Table 5.

TABLE 5

Quantification of the average DAR for exemplified anti-human CD33 Ab2 GC conjugate using fractional percentages based on total ion counts from Time of Flight mass spectrometry analysis.

| DAR | Ion counts | DAR Contribution |
|---|---|---|
| 0 | 32926 | 0.00 |
| 1 | 0 | 0.00 |
| Total LC % | 32926 | |
| | LC Avg DAR | 0.00 (DAR contribution from LC) |

TABLE 5-continued

Quantification of the average DAR for exemplified anti-human CD33 Ab2 GC conjugate using fractional percentages based on total ion counts from Time of Flight mass spectrometry analysis.

| DAR | Ion counts | DAR Contribution |
|---|---|---|
| 0 | 0 | 0.00 |
| 1 | 17838 | 0.05 |
| 2 | 301109 | 1.82 |
| 3 | 12436 | 0.11 |
| 4 | 0 | 0.00 |
| Total HC % | 331383 | |
| | HC Avg DAR | 1.97 (DAR contribution from HC) |
| (HC + LC)2 | Final Avg DAR | 3.97 |

Example 1c. Generation of Anti-human CD33 Ab2 GC Conjugate Wherein n is 3

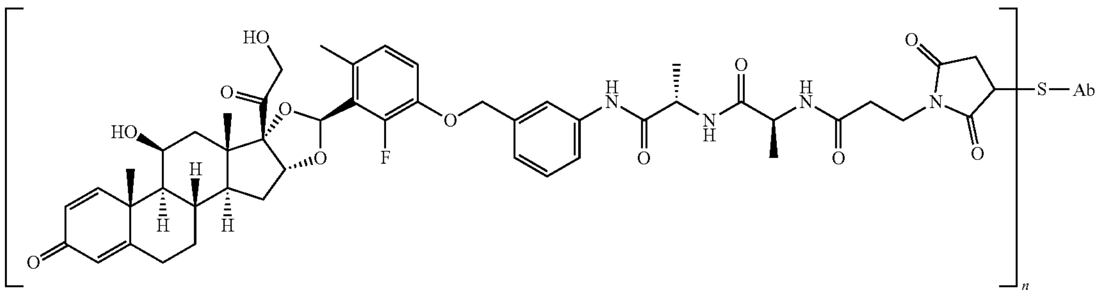

wherein n is 3; and

Ab is Ab2.

The conjugate of Example 1c was prepared in a manner analogous to the procedure described in Example 1b using a molar ratio of GC-L:Ab2 of 4:1, with 20-minute incubation at ~21° C. resulting in a final DAR of approximately 3. Example 1d Thiosuccinimide hydrolysis: The thiosuccinimide ring of the conjugate Formula Ia, can by hydrolyzed under conditions well known in the art as shown below (See, e.g., WO 2017/210471, paragraph 001226) to provide the ring-opened product of Formula Ib.

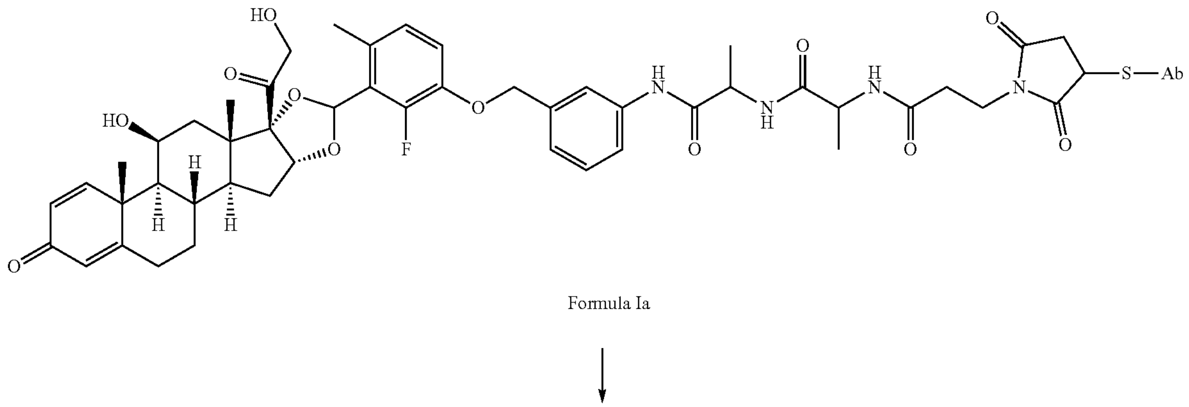

Formula Ia

-continued

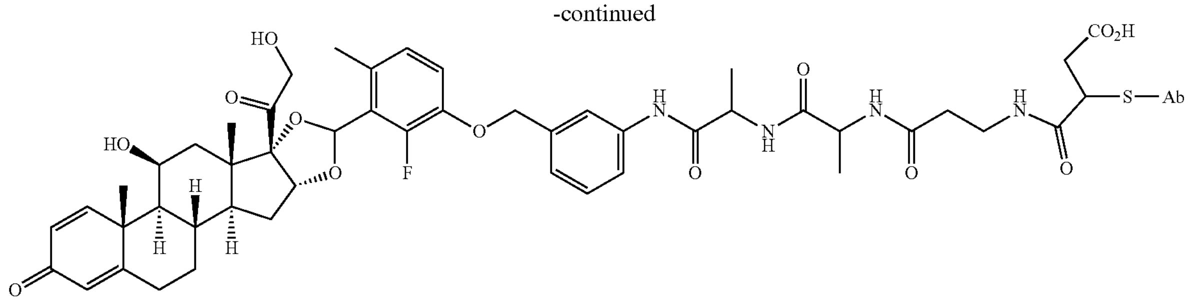

Formula Ib

In addition, the above thiosuccinimide ring of the conjugate Formula Ia may undergo at least partial hydrolysis in vivo and under standard or well-known formulation conditions to provide the ring-opened product of Formula Ib.

Example 2. Binding Activity

Example 2a. Binding Affinity

The affinity and binding kinetics of the exemplified anti-human CD33 antibodies to human and cynomolgus monkey CD33 ECD 18-232-His proteins was determined by surface plasmon resonance using Biacore 8K (GE Healthcare). Briefly, per the Instrument Handbook the antibody was captured on a Biacore Protein A chip followed by flowing CD33 ECD from 200 nM down to 0.782 nM in 2-fold serial dilution in PBS-P20-BSA (0.005% surfactant P20, 0.1 mg/mL BSA). All measurements were carried out at 37° C. Multi-cycle kinetics setting that ran each analyte concentration in a separate cycle regenerating the surface after each sample injection was used. The regeneration was optimized to maintain consistent surface properties from cycle to cycle. Each cycle started with a 3 minute injection of 0.1 μg/mL of the antibody at 10 μl/min flow rate, followed by 3 min injection of antigen at 50 μl/min flow rate and a 15 min dissociation phase in PBS-P20-BSA. The chip surface was then regenerated with 30 seconds injection of pH 1.5, 10 mM glycine buffer at 50 μl/min flow rate three times. The data was fit to a 1:1 binding model to derive $k_a$ and $k_d$, and to calculate $K_D$.

The results in Table 3, show exemplified anti-human CD33 Ab2 GC conjugate of Example 1b maintained similar binding affinity as the unconjugated anti-human CD33 Ab2 to human and cynomolgus monkey CD33. Furthermore, Ab1, Ab2 and Ab3 bound human CD33 with desirable affinities, whereas and Ab1 and Ab2 had improved binding to cynomolgus monkey.

TABLE 3

Binding affinity and kinetics of exemplified anti-human CD33 Antibody GC conjugate of Example 1b, Ab1, Ab2 and Ab3 to human and cynomolgus monkey CD33 ECD

| | Species | $k_a$ (1/Ms) | $k_d$ (1/s) | $K_D$ (M) |
|---|---|---|---|---|
| Ab1 | Human | 3.46E+05 | 1.18E+05 | 3.4E−09 |
| | Cynomolgus monkey | 2.55E+03 | 6.15E−02 | 2.41E−05 |
| Ab2 | Human | 4.54E+05 | 5.16E−04 | 1.14E−09 |
| | Cynomolgus monkey | 6.53E+05 | 2.79E−03 | 4.28E−09 |
| Ab3 | Human | 5.70E+05 | 4.86E−04 | 8.54E−10 |
| | Cynomolgus monkey | 1.34E+06 | 1.08E−03 | 8.12E−10 |

TABLE 3-continued

Binding affinity and kinetics of exemplified anti-human CD33 Antibody GC conjugate of Example 1b, Ab1, Ab2 and Ab3 to human and cynomolgus monkey CD33 ECD

| | Species | $k_a$ (1/Ms) | $k_d$ (1/s) | $K_D$ (M) |
|---|---|---|---|---|
| Ab2 GC | Human | 4.39E+05 | 6.45E−04 | 1.47E−09 |
| conjugate | Cynomolgus monkey | 1.03E+06 | 4.78E−03 | 4.65E−09 |

Example 2b. Cell Surface Binding Potency

Binding potency of the exemplified anti-human CD33 antibodies and anti-human CD33 Ab2 GC conjugate of Example 1b to human monocytes was tested in a Fluorescence Activated Cell Sorting (FACS) assay. Human PBMCs were isolated from human blood samples by standard Ficoll-Paque™ plus (GE HEALTHCARE) density gradient centrifugation methods. Freshly isolated cells PBMCs were resuspended at $2 \times 10^6$ cells/mL and allowed to rest for 15 minutes at room temperature, then plated at 100 μL/well into a round bottom 96-well plate (COSTAR®) and washed with FACS buffer (PBS containing 2% fetal bovine serum from Corning®). Exemplified anti-human CD33 antibodies and the respective control IgG antibodies conjugated to Alexa Fluor® 647 according to manufacturer's protocol (Thermo Fisher Scientific) were added to the wells and diluted 4-fold in duplicate. Equivalent volume of 2× antibody cocktail containing: PE-Cy5 anti-human CD14 Antibody (clone M5E2), Per-CP anti-human CD45 Antibody (clone H130), FITC anti-human CD11b (clone ICRF44), and Alexa Fluor-647 anti-human CD66b (G10F5) was then added to the wells. Cells were incubated at 4° C. for 30 mins, washed twice with FACS buffer and resuspended in a final volume of 100 μl FACS buffer. Viability dye, Live/Dead Yellow (Thermo Fisher Scientific, L34968), was added and the samples were analyzed via a flow cytometer (LSR-Fortessa™ X-20; BD BIOSCIENCES). Data analysis was performed using FlowJo software and statistical analysis was performed using GraphPad Prism 9. Data represents the mean fluorescence intensity (MFI) of CD33 expressing cells from monocytes or neutrophils.

Figure 1B:
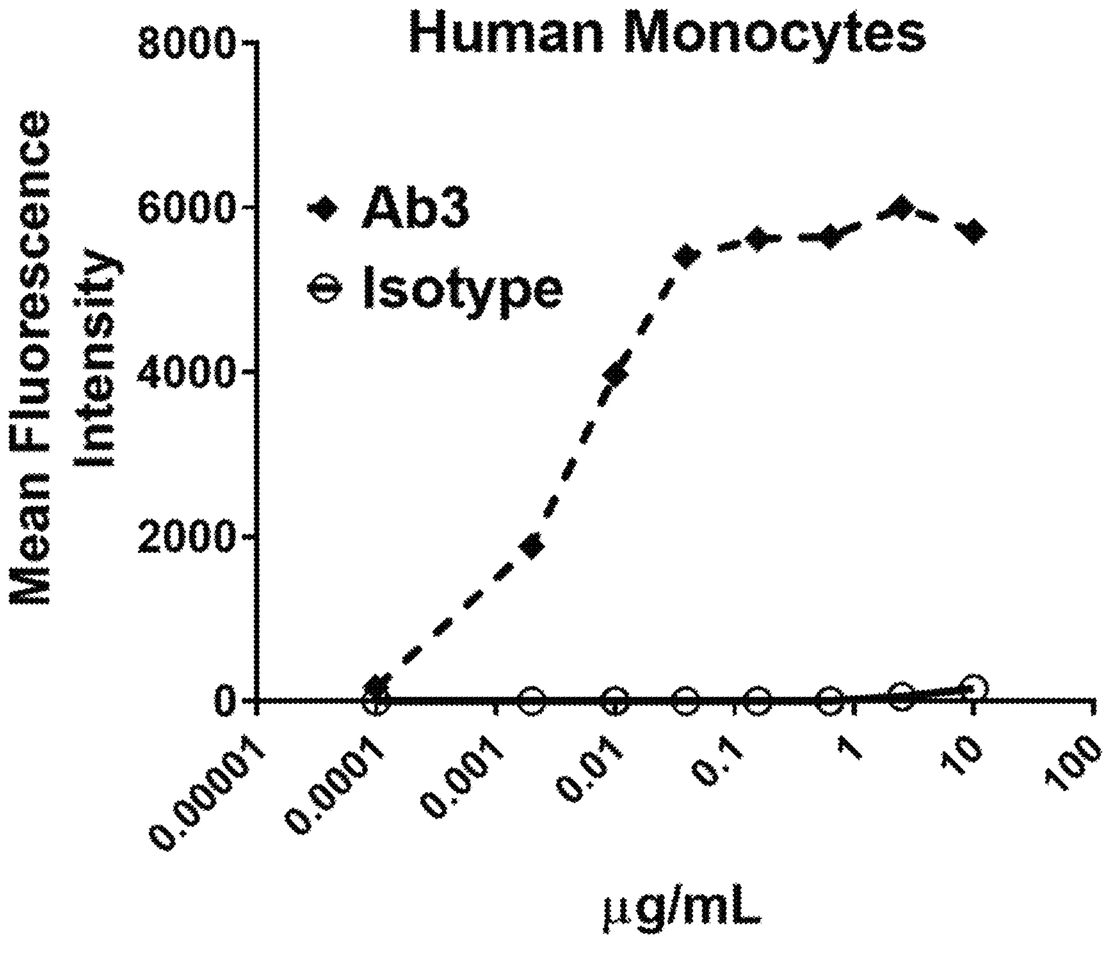

The results in FIGS. 1A-1B, show exemplified anti-human CD33 Ab2 GC conjugate of Example 1b, and Ab2 bound human CD33 expressed on the monocyte cell surface with desirable binding potency. FIG. 1B shows binding of Ab3 to the monocyte cell surface.

Example 3: Functional Activity

Example 3a. Antibody Internalization

Exemplified anti-human CD33 antibodies were labeled with pHrodo™ Red, amine-reactive dye (Thermo Fisher, P36014). The pH-sensitive dye was a non-fluorescent when outside the cells but fluoresces brightly in acidic low-pH lysosomes. This property allows visualization and qualification of the internalization of an antibody by flow cytometry. Human PBMCs (500 K/well) were incubated on ice in FACS buffer for 30 min, to quiesce baseline internalization. Cells were stained with pHrodo-labeled antibodies (10 μg/mL) in FACS buffer for 1 hour on ice then transferred to 37° C. for 2 hours. Cells were then stained with the remaining panel of surface detection marker: CD45 mAb (clone HI30); CD11b (clone ICRF44); CD14 (clone M5E2).

The results in Table 4 show that about >80% of the exemplified anti-human CD33 Ab2 GC conjugate of Example 1b and Ab2 was internalized into the primary human monocyte cells within about 2 hours of binding to cell surface CD33. In comparison, only about 50% of Gemtuzumab (hIgG4PAA) was internalized into the primary human monocyte cells within about 2 hours of binding to cell surface CD33. The faster and/or increased internalization rate of exemplified anti-human CD33 Ab2 GC conjugate of Example 1b and Ab2 into the monocyte cells suggests Ab2 can effectively deliver a therapeutic agent linked to it into CD33 expressing cells.

TABLE 4

Internalization of exemplified anti-human CD33 Ab2 GC conjugate of Example 1b, Ab2, and gemtuzumab

| | % Internalization |
|---|---|
| hIgG1AAA Isotype control | 2.26 ± 0.693 |
| hIgG4PAA Isotype control | 3.49 ± 1.626 |
| Ab2 | 86.545 ± 4.589 |
| Ab2 GC conjugate | 86.55 ± 6.859 |
| Gemtuzumab | 50.55 ± 2.899 |

Example 3b. CD33 Cell Surface Receptor Availability Post-Internalization

CD33 cell surface receptor availability on monocytes after internalization upon binding to the exemplified anti-human CD33 antibodies was evaluated. Briefly, human monocytes isolated from PBMC were seeded at $2\times10^4$ cells/well in a 96-well plate and incubated on ice for 60 minutes to impede internalization. Exemplified anti-human CD33 antibodies (30 μg/mL) were added to the cells and allowed to bind for 30 minutes on ice. 100 μL culture media was then added to the cells and plates were placed in the incubator for 3.5, 24, 48, 72, and 96-hour timepoints at 37° C. The baseline samples were stained immediately representing the exemplified anti-human CD33 antibody surface binding before internalization. Cells were Fc blocked for 20 minutes, then stained with Alexa Fluor-647 labeled anti-human CD33 exemplified antibodies, Alexa Fluor-700 anti-human CD45 (HI30) and Brilliant Violet-605 anti-human CD11b (ICRF44) for 30 minutes on ice. Cells were analyzed by flow cytometry.

The results in Table 5, show that cell surface CD33 availability on the monocyte cells increases from baseline over the course of about 3.5 hours to about 96 hours post internalization from about 1.1% to up to about 31.9% respectively. surface CD33 may be from de novo CD33 expression and/or internalized CD33 which was recycled to the cell surface. These results indicated that the regenerated CD33 on the human monocyte cells can potentially bind additional anti-human CD33 antibodies for repeated delivery of the CD33 antibody or therapeutic agent linked to the CD33 antibody into the CD33 expressing cells.

TABLE 5

CD33 cell surface availability post internalization after treatment with exemplified Ab1

| | % cell surface CD33 positive cells post internalization |
|---|---|
| Baseline | 1.1 ± 0.481 |
| 3.5 hours | 1.06 ± 0.339 |
| 24 hours | 1.935 ± 0.884 |
| 48 hours | 9.195 ± 1.260 |
| 72 hours | 14.185 ± 1.335 |
| 96 hours | 31.9 ± 2.183 |

Example 3c. CD33 Receptor Degradation

Impact of the exemplified anti-human CD33 Ab2 on intracellular CD33 degradation was evaluated by a protein immunoblot assay. Human PBMCs were isolated from human blood samples by standard Ficoll-Paque™ plus (GE HEALTHCARE) density gradient centrifugation methods. Freshly isolated PBMCs were seeded in 24-well cell culture plate at $1\times10^7$ cells/5 mL/well in culture media. The cells were treated with anti-human CD33 Ab2 and a hIgG1 (effector null) negative control antibody overnight in a 37° C. cell incubator. This step allowed for determining degradation of internalized CD33 receptor. Cells were collected the following day and lysed with RIPA lysis buffer with protease and phosphatase inhibitors. Cell lysate protein was quantified by bicinchoninic acid (BCA) assay, and normalized for loading for the protein immunoblot assay. A non-competing anti-CD33 antibody (AbCam clone EPR4423) was used to detect CD33 levels.

Figure 2A:
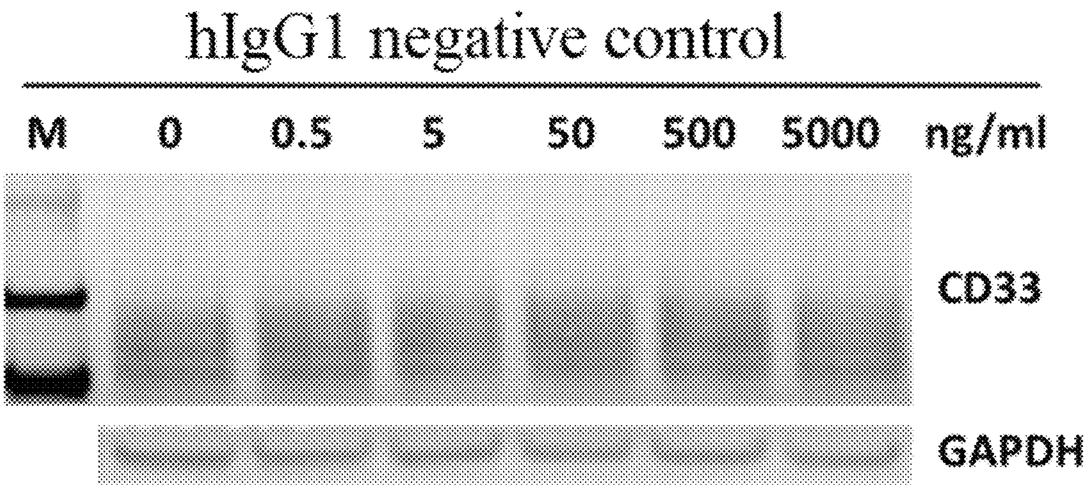
FIGS. 2A-2B show that Ab2 binding to CD33 expressing cells did not degrade cell surface or intracellular CD33 (2B) relative to hIgG1 negative control (2A).
Figure 2B:
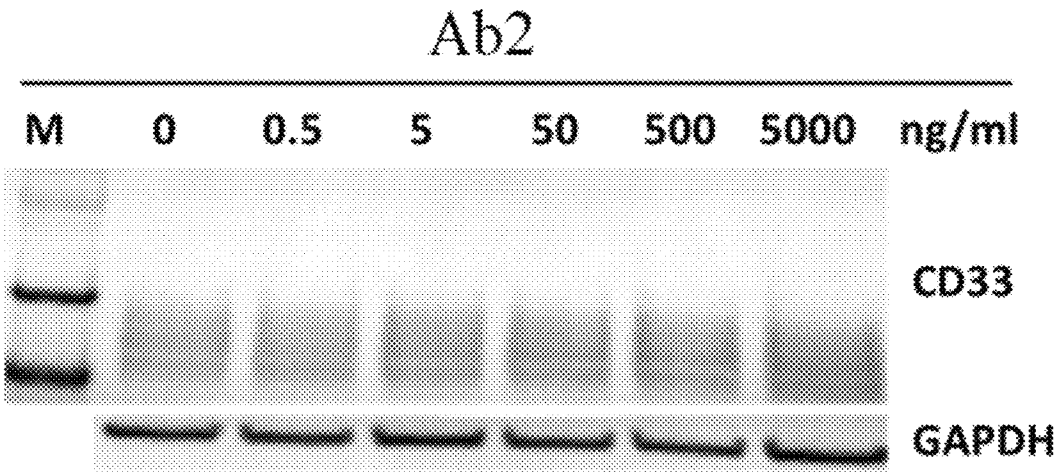
Figure 3A:
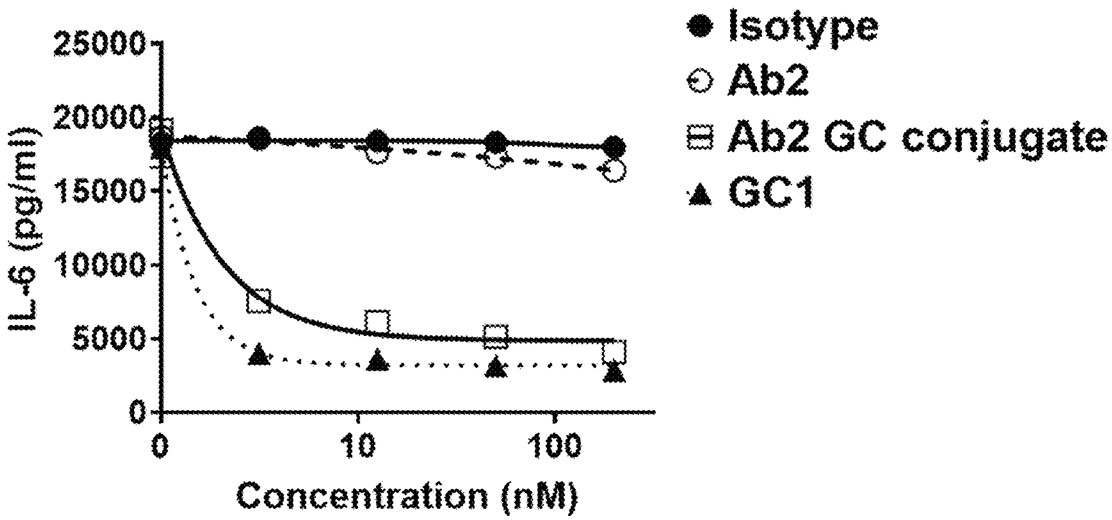
FIGS. 3A-3D show treatment with anti-human CD33 Ab2 GC conjugate of Example 1b modulated IL-6 (3A) and TNFα (3B) cytokine expression in human PBMCs and that the response is modulated by the GC and not by the Ab2 (3A-3B) or Ab3 (3C-3D).
Figure 3B:
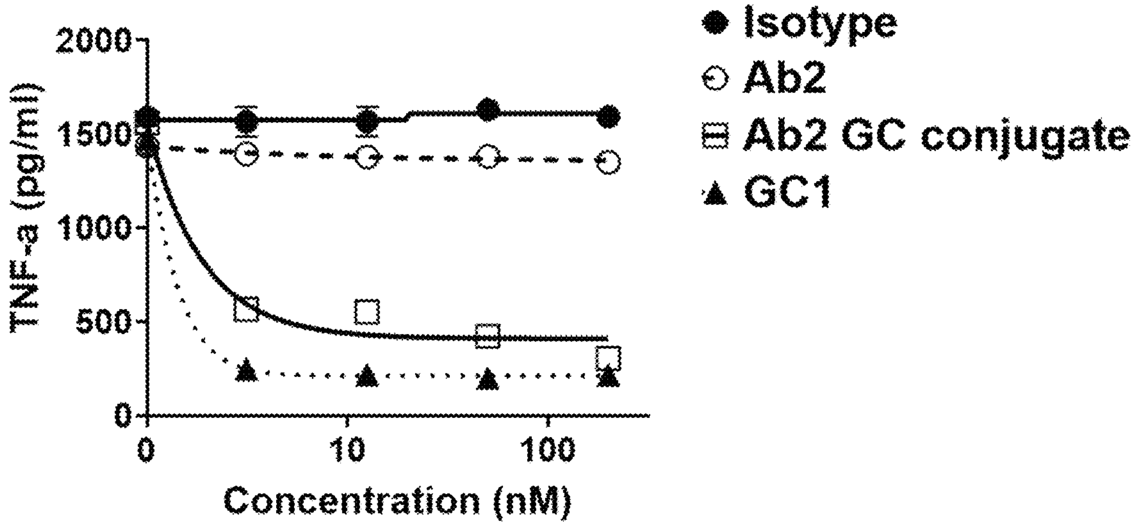
Figure 3C:
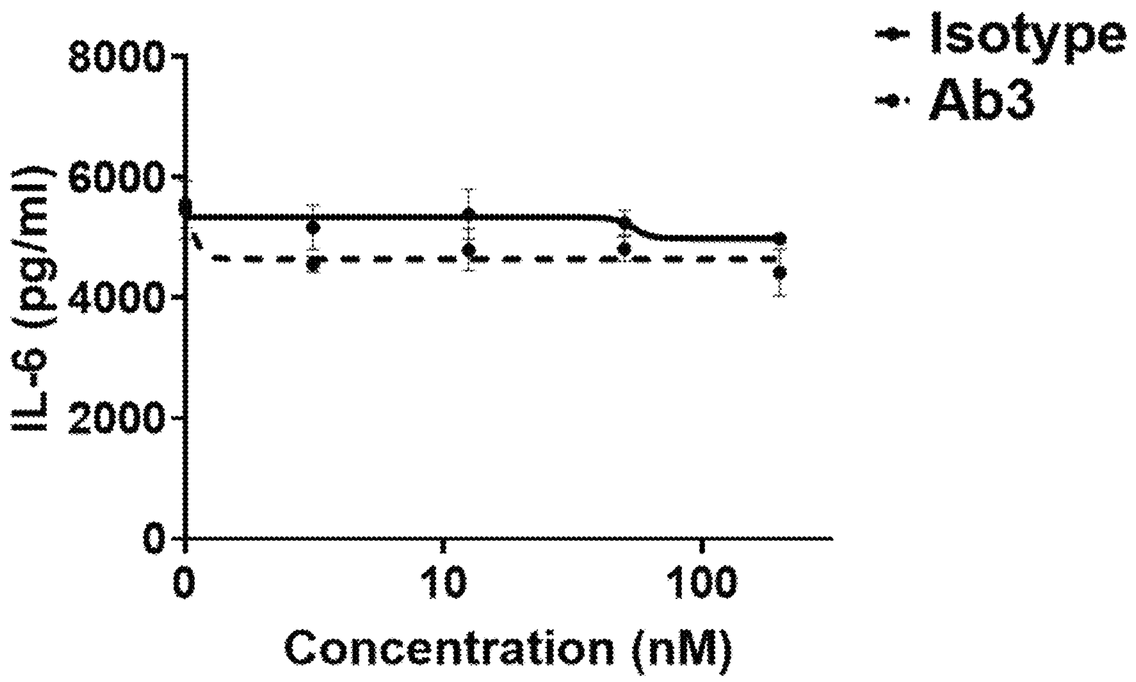
Figure 3D:
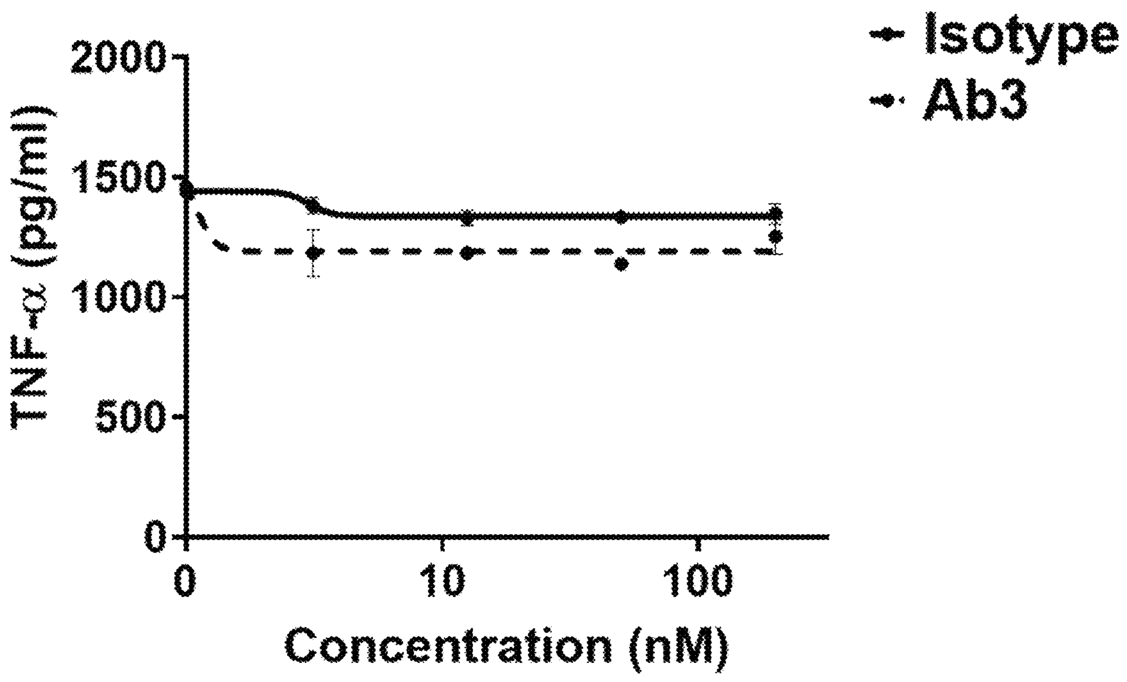

The results in FIGS. 2A-2B, show that exemplified anti-human CD33 Ab2 did not degrade the CD33 upon binding and internalization, as the CD33 levels were comparable to the isotype control.

Example 3d Proinflammatory Cytokine Modulation and Immune Cell Depletion

The exemplified anti-human CD33 Ab2 GC conjugate of Example 1b and anti-human CD33 Ab2 were evaluated for effect on proinflammatory cytokine modulation in human PBMCs. PBMCs were used to mimic in vivo conditions. Briefly, exemplified anti-human CD33 Ab2 or anti-human CD33 Ab2 GC conjugate of Example 1b were incubated with human PBMCs at $2\times10^6$ cells/well in a 96-well plate in a 37° C. incubator for 1 hour. The cells were then stimulated with LPS (Sigma cat. L2880) at 100 pg/mL in a 37° C. incubator for 24 hours. Culture supernatants were collected to measure the indicated cytokines (Proinflammatory Panel II (human) 4-Plex kits, MSD, K15053D-2).

The results in FIGS. 3A-3D and Table 6a shows that the anti-human CD33 Ab2 GC conjugate of Example 1b significantly modulated (inhibited) proinflammatory cytokine IL-6 and TNFα responses similar to that of the GC1 alone. The unconjugated anti-human CD33 Ab2 did not modulate CD33 mediated expression of proinflammatory cytokines IL-6 and TNFα indicating that the cytokine response observed with exemplified anti-human CD33 Ab2 GC conjugate is modulated by the glucocorticoid.

Table 6b shows that treatment with anti-human CD33 Ab2 GC conjugate of Example 1b and the anti-human CD33 Ab2, did not induce PBMC immune cell depletion as compared to the isotype control.

TABLE 6a

Proinflammatory cytokine modulation by the exemplified anti-human CD33 Ab2 GC conjugate of Example 1b

| | % Inhibition of human IL-6 secretion at 200 nM | % Inhibition of human TNFa secretion at 200 nM |
|---|---|---|
| Isotype | 1.638 ± 1.565 | 3.214 ± 0.264 |
| Ab2 | 12.045 ± 1.887 | 5.978 ± 0.548 |
| Ab2 GC conjugate | 78.604 ± 0.836 | 80.469 ± 2.579 |
| GC1 | 83.908 ± 2.815 | 85.126 ± 3.278 |

TABLE 6b

Exemplified anti-human CD33 Ab2 GC conjugate of Example 1b and anti-human CD33 Ab2 do not induce immune cell depletion

| | Total Viable Cell Count | | | |
|---|---|---|---|---|
| | No Treatment | Isotype | Ab2 | Ab2 GC conjugate |
| LPS Stimulation | 1.75 ± 0.3 | 1.54 ± 0.15 | 1.64 ± 0.12 | 1.57 ± 0.16 |
| No LPS | 1.79 ± 0.27 | 1.51 ± 0.23 | 1.43 ± 0.33 | 1.61 ± 0.07 |

viable cell counts (x$10^6$ cells/mL)

Example 3& Plasmacytoid Dendritic Cell Assay

The ability of exemplified anti-human CD33 Ab2 GC conjugate to modulate human plasmacytoid dendritic cells (pDCs) was assessed in a pDC differentiation assay. pDCs known to express CD33, are the primary cells that produce type 1 interferon which is associated with lupus pathogenesis. Briefly, human PBMCs were cultured in IL-3 supplemented culture media with stimulation of CpG (immunostimulatory DNA containing unmethylated cytosine-phosphate-guanosine) in the presence of anti-human CD33 Ab2 or anti-human CD33 Ab2 GC conjugate of Example 1b or the GC1 alone. The differentiation of pDC was measured by flow cytometry. The functional effects of the pDC were measured by type I IFN (IFNα) production.

The results in Tables 6c shows that the anti-human CD33 Ab2 GC conjugate of Example 1b significantly modulated (inhibited) differentiation of the pDC's and inhibited cytokine IFNα secretion similarly to that of the GC1 alone. The unconjugated anti-human CD33 Ab2 did not impact pDC differentiation and IFNα secretion indicating that the inhibition of the cytokine response observed with exemplified anti-human CD33 Ab2 GC conjugate is modulated by the glucocorticoid. The results thus demonstrate that the anti-human CD33 Ab2 GC conjugate of Example 1b specifically targets functional activity of the pDCs.

TABLE 6c

Inhibition of pDC and IFNα by the exemplified anti-human CD33 Ab2 GC conjugate of Example 1b

| | % Inhibition of pDC cell differentiation | % Inhibition of human IFNα secretion |
|---|---|---|
| Isotype | 0.92 ± 0.06 | 0.83 ± 0.21 |
| Ab2 | 0.97 ± 0.39 | 1.25 ± 0.19 |

TABLE 6c-continued

Inhibition of pDC and IFNα by the exemplified anti-human CD33 Ab2 GC conjugate of Example 1b

| | % Inhibition of pDC cell differentiation | % Inhibition of human IFNα secretion |
|---|---|---|
| Ab2 GC conjugate | 91.89 ± 6.37 | 95.62 ± 1.57 |
| GC1 | 95.50 ± 8.32 | 97.18 ± 2.95 |

Example 4. Effector Function Activity

Antibody dependent cellular cytotoxicity (ADCC): In vitro ADCC assays of the exemplified antibodies was evaluated with a reporter gene based ADCC assay. CHO cells expressing human CD33 and human CD20 as the target cell line and Jurkat cells expressing functional FcγRIIIa (V158)-NFAT-Luc (Eli Lilly and Company) as the effector cell line were used. All test antibodies and cells were diluted in assay medium containing RPMI-1640 (no phenol red) with 0.1 mM non-essential amino acids (NEAA), 1 mM sodium pyruvate, 2 mM L-glutamine, 500 U/mL of penicillin-streptomycin, and 0.1% w/v BSA. Test antibodies were first diluted to a 3× concentration of 3.3 μg/mL and then serially diluted 7 times in a 1:4 ratio. 50 μL/well of each antibody was aliquoted in duplicate in white opaque bottom 96-well plate (Costar, #3917). CD20 antibody was used as a positive control. CHO target cells were then added to the plates at 5×$10^4$ cells/well in 50 μL, aliquots, and incubated for 1 hour at 37° C. Next, Jurkat V158 cells were added to the wells at 150,000 cells/well in 50 μL aliquots and incubated for 4 hours at 37° C., followed by addition of 100 μL/well of One-Glo Luciferase substrate (Promega, #E8130). The contents of the plates were mixed using a plate shaker at low speed, incubated at room temperature for 5 minutes, and the luminescence signal was read on a BioTek microplate reader (BioTek Instruments) using 0.2 cps integration. Data was analyzed using GraphPad Prism 9 and the relative luminescence units (RLU) for each antibody concentration was plotted in a scatter format of antibody concentration versus RLU.

The exemplified anti-human CD33 antibodies having the effector null IgG1AAA backbone did not induce ADCC activity (results not shown), suggesting that the exemplified antibodies have a low probability of depleting CD33 expressing cells via ADCC mediated killing.

Example 5. Biophysical Properties

Biophysical properties of the exemplified anti-human CD33 antibodies were evaluated for developability.

Aggregation from cell culture: The exemplified anti-human CD33 antibodies were transiently expressed in CHO cells. The antibody titers and percentage of high molecular weight (% HMW) species after Protein A affinity chromatography purification are shown in Table 7 and indicate that Ab1, Ab2, and Ab3 have low aggregation, providing for good developability profiles.

Viscosity: Exemplified anti-human CD33 antibodies Ab1, Ab2, Ab3 and the anti-human CD33 Ab2 GC conjugate of Example 1b were concentrated to about 125 mg/mL in a 5 mM histidine matrix at pH 6. The viscosity for each was measured using VROC® initium (RheoSense) at 15° C. using the average of 9 replicate measurements. The results in Table 7, show that the exemplified anti-human CD33 antibodies Ab1, Ab2, Ab3 and anti-human CD33 Ab2 GC conjugate of Example 1b have good viscosity profiles for developability.

Thermal stability: Differential Scanning Calorimetry (DSC) was used to evaluate the stability of the exemplified anti-human CD33 antibodies Ab1, Ab2, Ab3 and the anti-human CD33 Ab2 GC conjugate of Example 1b against thermal denaturation. The results in Table 7 show that the exemplified anti-human CD33 antibodies Ab1, Ab2, Ab3 and the anti-human CD33 Ab2 GC conjugate of Example 1b have acceptable thermal melting temperatures in PBS, pH 7.2 for developability.

Aggregation upon temperature stress: The solution stability of the exemplified anti-human CD33 antibodies Ab2, Ab3 and the anti-human CD33 Ab2 GC conjugate of Example 1b over time was assessed at about 100 mg/mL in a common 5 mM histidine pH 6.0 buffer. Concentrated samples were incubated for a period of 4 weeks at 5° C. and 35° C., respectively. Following incubation, samples were analyzed for the percentage of high molecular weight (% HMW) species with size exclusion chromatography (SEC). The results in Table 7, show that the exemplified anti-human CD33 antibodies Ab2, Ab3 and the anti-human CD33 Ab2 GC conjugate of Example 1b had good stability under heat stress.

TABLE 7

Biophysical properties of the exemplified anti-human CD33 antibodies and the Ab2 GC conjugate of Example 1b

| | Ab1 | Ab2 | Ab3 | Ab2 GC conjugate |
|---|---|---|---|---|
| % HMW species after Protein A chromatography | 2.67 | 1.10 | 1.39 | NA |
| sCHO titer (g/L) | 1.7 | 4.7 | 4.6 | NA |
| Viscosity (cP) | 5.5 | 6.5 | 7.7 | 7.3 |
| $T_{onset}$ (° C.) | | 64.4 | 64.6 | 57.8 |
| Tm1 (° C.) | | 71.8 | 70.93 | 64.0 |
| Tm2 (° C.) | 79 | 77.5 | 79.68 | 77.0 |
| % HMW after 4-week incubation at 5° C. | ND* | <0.1 | <0.1 | 0.95 |
| % HMW after 4-week incubation at 35° C. | ND* | 0.86 | 1.58 | 3.08 |

*ND = Not determined

Example 6. Immunogenicity Assessment

MS serum protein binding: Off-target binding of the exemplified anti-human CD33 antibodies to serum proteins was assessed. Exemplified anti-human CD33 antibodies Ab1, Ab2, and Ab3, as well as the anti-human CD33 Ab2 GC conjugate of Example 1b were coated onto an Maxisorp microplate. Plates were blocked and human serum was added to the wells, and plates were incubated overnight. Bound proteins was eluted, reduced, alkylated, and digested. Peptides were analyzed by a mass spectrometer. Peptide and protein identifications were generated by an internal proteomics pipeline using search algorithms with tryptic enzyme and a human database with test antibody sequences appended. Ions were quantified by internal proteomics tools (Chrom-Alignment, Metaconsense and Quant) and analyzed in JMP using Oneway analysis/Compare Means/All pairs, Tukey HSD. Proteins with >30% of ions with P-value<0.05 and FC>2 (compared to isotype control) considered enriched in the study.

The results in Table 8, show that the exemplified anti-human CD33 antibodies Ab2 and Ab3 and the anti-human CD33 Ab2 GC conjugate of Example 1b had significantly reduced association with serum proteins when compared to Ab1, and thus potentially have lower immunogenicity risk than Ab1.

TABLE 8

MS serum protein analysis of exemplified anti-human CD33 antibodies and anti-human CD33 Ab2 GC conjugate of Example 1b

| mAb | Serum proteins identified w/antibody (>5-fold enrichment) |
|---|---|
| Ab1 | Some serum proteins identified |
| Ab2 | No serum proteins identified |
| Ab2 GC conjugate | No additional off-target binding observed compared with Ab2 |
| Ab3 | Pregnancy zone protein enriched |

Example 7: In vivo Characterization

Preclinical contact hypersensitivity model: Exemplified anti-human CD33 Ab2 GC conjugate of Example 1b and anti-human CD33 antibody Ab2 was assessed in vivo using a humanized mouse model (HuNOG-EXL) of contact hypersensitivity. Ab1 was similarly assessed in a separate study. Administration of oxazolone (an allergic contact dermatitis inducer) to the HuNOG-EXL induces local proinflammatory cytokine responses and skin inflammation. This allows for the interrogation of anti-inflammatory and immuno-modulating effects of the exemplified molecules in vivo.

Briefly, huNOG-EXL mice were engrafted at 6 weeks of age with human CD34+ hematopoietic stem cells isolated from human cord blood. 20-24 weeks after stem cell administration the mice were assessed for human CD45 engraftment (>25% in blood) and subjected to an oxazolone-induced contact hypersensitivity protocol. On day 0, mice were grouped by body weight (N=7-8/group) and dosed at 10, 1, and 0.1 mg/kg subcutaneously with the anti-human CD33 Ab2 GC conjugate of Example 1b, or 10 mg/kg of the anti-human CD33 Ab1 or Ab2, or a non-binding isotype control. 24 hours (Day 1) post administration, the mice were anesthetized with 5% isoflurane, their abdomens shaved, and sensitized with 100 μL of 3% oxazolone in ethanol (applied to the shaved area). Mice were dosed again on Day 4, 11, and 16 as above, and challenged with 2% oxazolone in ethanol on both ears (10 μL/side/ear) 48 hours post each dose (Day 6—Challenge 1, Day 13—Challenge 2, and Day 18—Challenge 3). For the GC1 alone group, mice were dosed with 3 mg/kg SC 1 hour prior to sensitization and prior to each challenge. Upon final challenge, mice were euthanized, and ear tissue and the gastrocnemius was collected for analysis of target selective and non-target selective tissue expression of GC regulated genes.

Figure 4A:
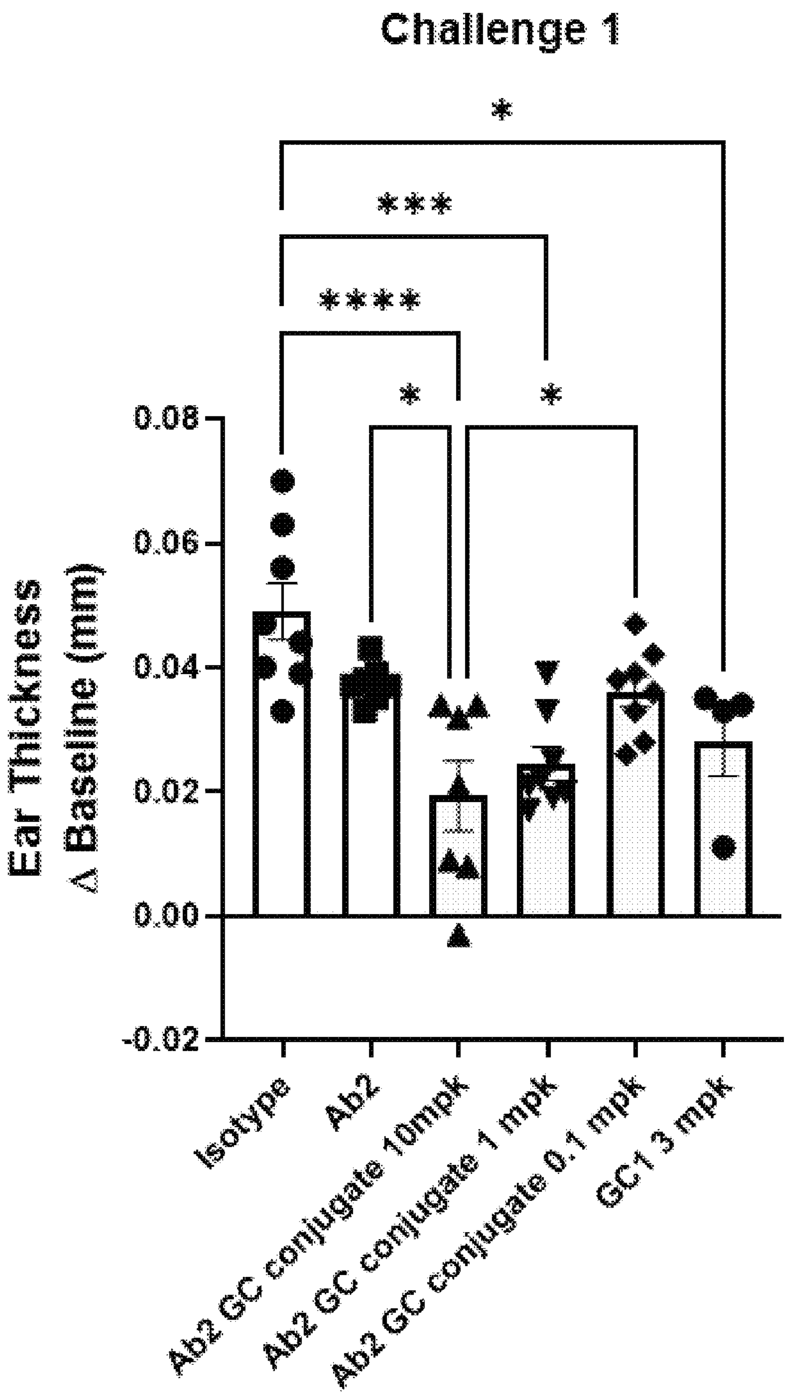
FIGS. 4A-4C show treatment with anti-human CD33 Ab2 GC conjugate of Example 1b significantly modulated (inhibited) oxazolone-induced skin inflammation in a dose-dependent manner in subsequent oxazolone challenges (Challenge 1-4A, Challenge 2-4B, and Challenge 3-4C) and that the inhibition is driven by the GC, and not by the Ab2.
Figure 4B:
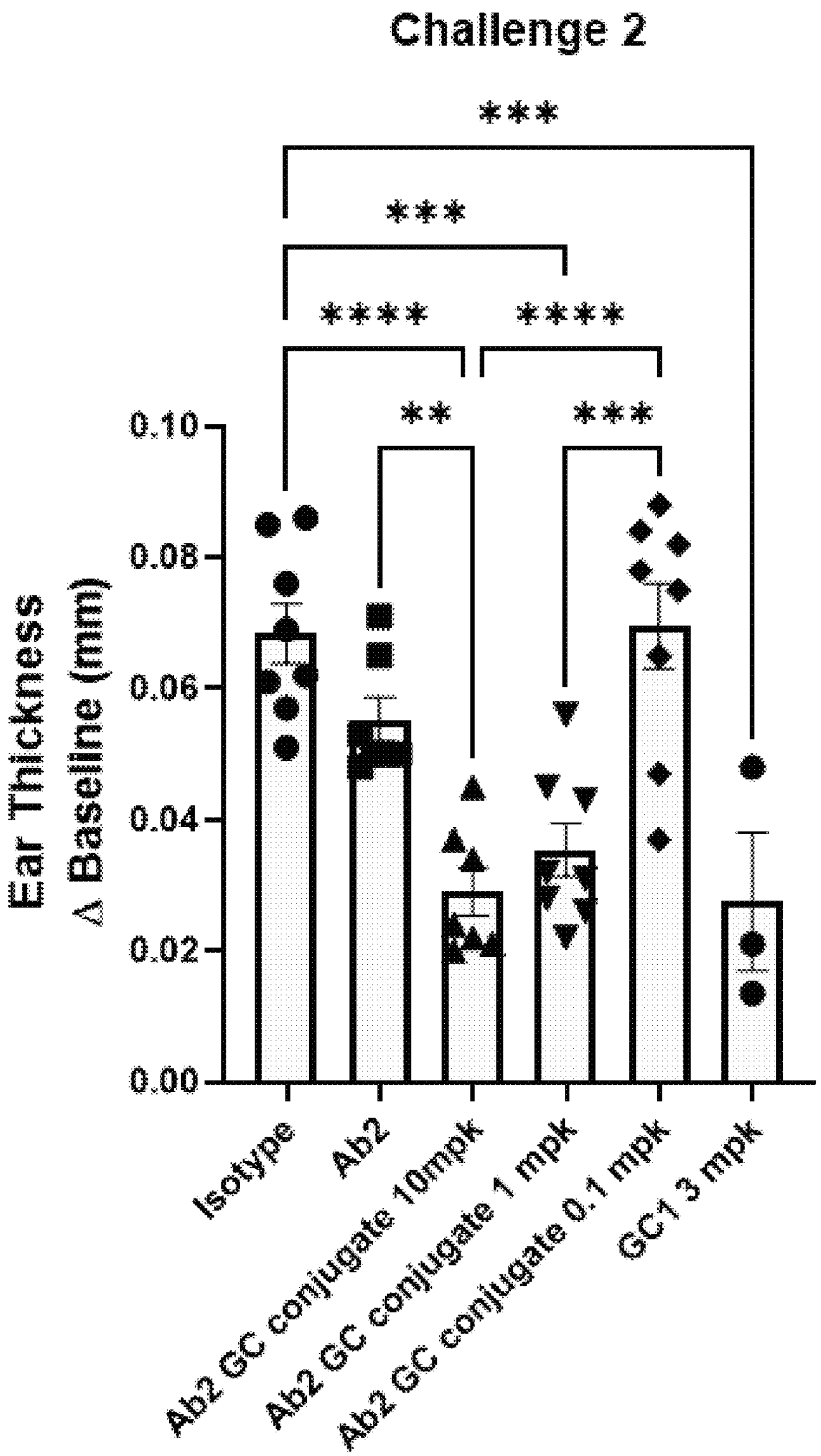
Figure 4C:
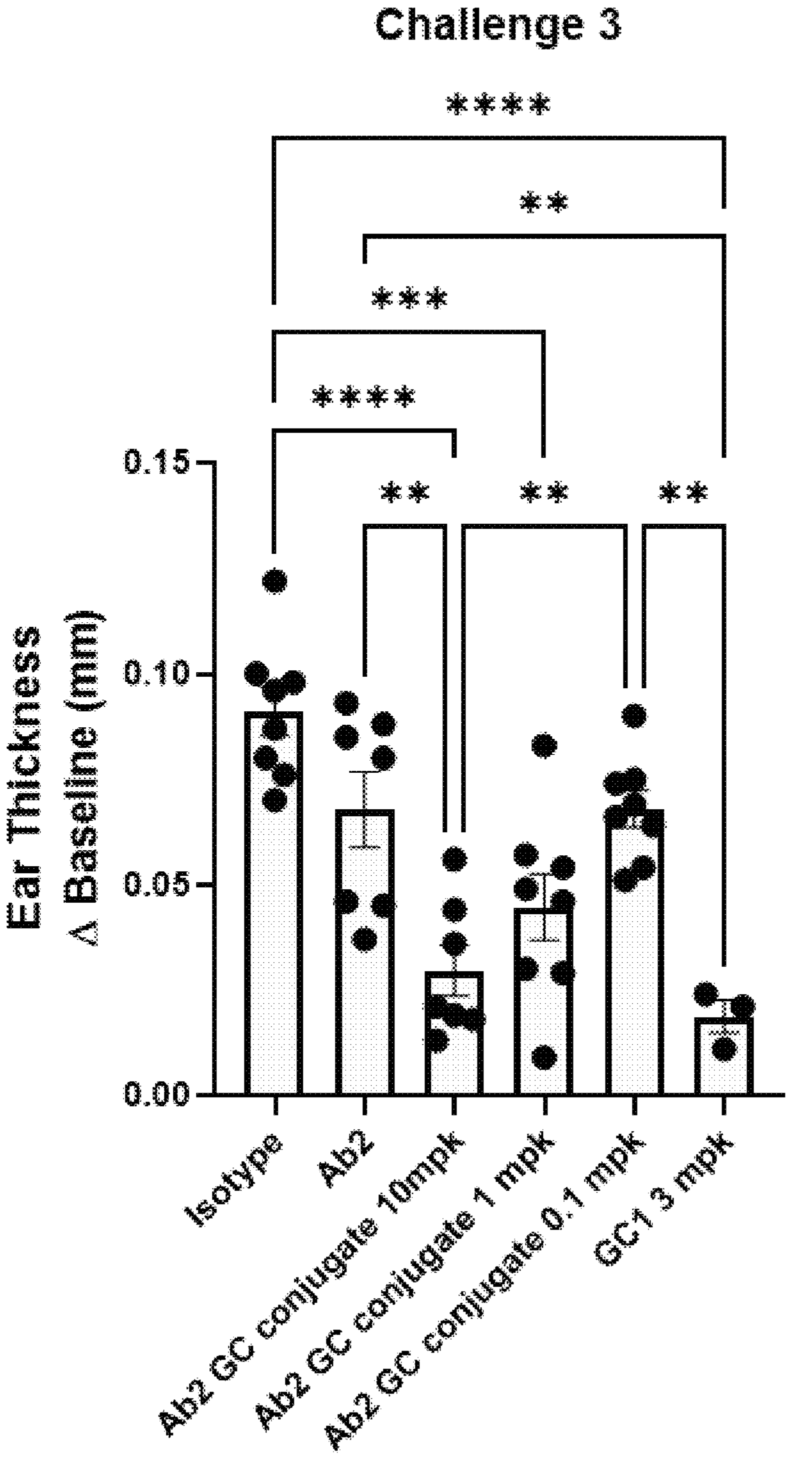

The results in Tables 9a and FIGS. 4A-4C, show that the anti-human CD33 Ab2 GC conjugate of Example 1b significantly suppressed in vivo oxazolone-induced skin inflammation at all 3 challenges. The results in Tables 9a further show that the anti-human CD33 Ab2 GC conjugate of Example 1b suppressed oxazolone-induced skin inflammation at Challenge 3 by 57% at 10 mg/kg and by 34% at 1 mg/kg when compared to the unconjugated Ab2 at 10 mg/kg. In a separate study, effect of Ab1 also showed no statistically significant difference from the isotype control (data not shown).

The results in Table 9b, show that the anti-human CD33 Ab2 GC conjugate of Example 1b modulated target tissue specific (ear) glucocorticoid receptor agonist mediated FKBP5 gene expression and not non-target tissue (gastrocnemius) FKBP5 gene expression. In contrast, systemic high dose glucocorticoid (GC1) treated mice showed glucocorticoid agonist receptor mediated gene induction in both target and non-target tissues.

Cumulatively, these data show the exemplified anti-human CD33 Ab2 GC conjugate of Example 1b specifically delivered the glucocorticoid to the target cells which subsequently modulated tissue specific GC agonist receptor mediated responses.

TABLE 9a

In vivo activity of exemplified anti-human CD33 Ab2 and anti-human CD33 Ab GC conjugate of Example 1b in a type IV hypersensitivity humanized mouse model; data from challenge 3.

| | Challenge 3 Δ Ear thickness (mm) | |
|---|---|---|
| | Mean | SEM |
| Isotype 10 mg/kg | 0.091 | 0.006 |
| Ab2 10 mg/kg | 0.067 | 0.009 |
| Ab2 GC conjugate 10 mg/kg | 0.029*^ | 0.006 |
| Ab2 GC conjugate 1 mg/kg | 0.044* | 0.008 |
| Ab2 GC conjugate 0.1 mg/kg | 0.068 | 0.004 |
| GC1 3 mg/kg | 0.018*^ | 0.004 |

*p < 0.0002 vs Isotype; ANOVA Tukey;
^p < 0.005 vs Ab2; ANOVA Tukey

TABLE 9b

Human glucocorticoid responsive gene induction by CD33 Ab2 GC conjugate of Example 1b and Ab2 in targeted tissue (Ear) and non-targeted tissue (Gastrocnemius) in a type IV hypersensitivity humanized mouse model

| | Fold increase in FKBP5 gene expression compared to Isotype | | | |
|---|---|---|---|---|
| | Ear | | Gastrocnemius | |
| | Mean | SEM | Mean | SEM |
| Ab2 | 1.549 | 0.020 | 1.076 | 0.096 |
| Ab2 GC conjugate 10 mg/kg | 9.011 | 2.351 | 0.789 | 0.445 |
| Ab2 GC conjugate 1 mg/kg | 5.278 | 1.767 | 1.176 | 0.491 |
| Ab2 GC conjugate 0.1 mg/kg | 1.930 | 0.934 | 1.149 | 0.390 |
| GC1 3 mg/kg | 4.505 | 0.928 | 3.958 | 1.445 |

SEQUENCE LISTING

Ab1
SEQ ID NO: 1 HCDR1 (North) for Ab1, Ab2, and Ab3
AASGFTFSSYAMS

SEQ ID NO: 2 HCDR2 (North) for Ab1, Ab2, and Ab3
AISGSGGSTY

SEQ ID NO: 17 HDCR3 (North) for Ab1
AREYSNYDY

SEQ ID NO: 18 LCDR1 (North) for Ab1
QASQDVFRYLN

SEQ ID NO: 5 LCDR2 (North) for Ab1, Ab2, and Ab3
YDASNLQT

SEQ ID NO: 6 LCDR3 (North) for Ab1, Ab2, and Ab3
QQYEDLPT

SEQ ID NO: 19 VH for Ab1
EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCAREYSNYDYWG
QGTLVTVSS SEQ ID NO: 20 VL for Ab1
DIQMTQSPSSLSASVGDRVTITCQASQDVFRYLNWYQQKPGKAPKLLIYDASNLQ
TGVPSRFSGSGSGTDFTFTISSLQPEDIATYYCQQYEDLPTFGPGTKVDIK SEQ ID NO: 21 HC for Ab1
EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCAREYSNYDYWG
QGTLVTVSSASTKGPCVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKS
CDKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LAAPIEKTISKAKGQPREPQVYTLPPSREEMTKNQVSLTCLVKGFYPSDICVEWES
NGQPENNYKTTPPVLDSDGSFFLYSKLTVDKSRWQQGNVFSCSVMHEALHNHY
TQKSLSLSPGK SEQ ID NO: 22 LC for Ab1
DIQMTQSPSSLSASVGDRVTITCQASQDVFRYLNWYQQKPGKAPKLLIYDASNLQ
TGVPSRFSGSGSGTDFTFTISSLQPEDIATYYCQQYEDLPTFGPGTKVDIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC -continued

SEQUENCE LISTING

SEQ ID NO: 23 HC DNA for Ab1
GAGGTGCAGCTGTTGGAGTCTGGGGGAGGCTTGGTACAGCCTGGGGGGTCCC
TGAGACTCTCCTGTGCAGCCTCTGGATTCACCTTTAGCAGCTATGCCATGAGC
TGGGTCCGCCAGGCTCCAGGGAAGGGGCTGGAGTGGGTCTCAGCTATTAGTG
GTAGTGGTGGTAGCACATACTACGCAGACTCCGTGAAGGGCCGGTTCACCAT
CTCCAGAGACAATTCCAAGAACACGCTGTATCTGCAAATGAACAGCCTGAGA
GCCGAGGACACGGCCGTATATTACTGTGCGAGGGAATATAGTAATTATGACT
ACTGGGGTCAGGGAACCCTGGTCACCGTCTCCTCAGCTAGCACCAAGGGCCC
ATGCGTCTTCCCCCTGGCACCCTCCTCCAAGAGCACCTCTGGGGGCACAGCGG
CCCTGGGCTGCCTGGTCAAGGACTACTTCCCCGAACCGGTGACGGTGTCGTGG
AACTCAGGCGCACTGACCAGCGGCGTGCACACCTTCCCGGCTGTCCTACAGTC
CTCAGGACTCTACTCCCTCAGCAGCGTGGTGACCGTGCCCTCCAGCAGCTTGG
GCACCCAGACCTACATCTGCAACGTGAATCACAAGCCCAGCAACACCAAGGT
GGACAAGAGAGTTGAGCCCAAATCTTGTGACAAAACTCACACATGCCCACCG
TGCCCAGCACCTGAAGCCGCCGGGGGACCGTCAGTCTTCCTCTTCCCCCCAAA
ACCCAAGGACACCCTCATGATCTCCCGGACCCCTGAGGTCACATGCGTGGTG
GTGGACGTGAGCCACGAAGACCCTGAGGTCAAGTTCAACTGGTATGTGGACG
GCGTGGAGGTGCATAATGCCAAGACAAAGCCGCGGGAGGAGCAGTACAACA
GCACGTACCGTGTGGTCAGCGTCCTCACCGTCCTGCACCAAGACTGGCTGAAT
GGCAAGGAGTACAAGTGCAAGGTCTCCAACAAAGCCCTCGCCGCCCCCATCG
AGAAAACCATCTCCAAAGCCAAAGGGCAGCCCCGAGAACCACAGGTGTACA
CCCTGCCCCCATCCCGGGAGGAGATGACCAAGAACCAAGTCAGCCTGACCTG
CCTGGTCAAAGGCTTCTATCCCAGCGACATCTGCGTGGAGTGGGAGAGCAAT
GGGCAGCCGGAGAACAACTACAAGACCACGCCTCCCGTGCTGGACTCCGACG
GCTCCTTCTTCCTCTATTCCAAGCTCACCGTGGACAAGAGCAGGTGGCAGCAG
GGGAACGTCTTCTCATGCTCCGTGATGCATGAGGCTCTGCACAACCACTACAC
GCAGAAGAGCCTCTCCCTGTCTCCGGGCAAA SEQ ID NO: 24 LC DNA for Ab1
GACATCCAGATGACCCAGTCTCCATCCTCCCTGTCTGCATCTGTAGGAGACAG
AGTCACCATCACTTGCCAGGCGAGTCAGGACGTTTTCAGGTATTTAAATTGGT
ATCAGCAGAAACCAGGGAAAGCCCCTAAGCTCCTGATCTACGATGCATCCAA
TTTGCAAACAGGGGTCCCATCAAGGTTCAGTGGAAGTGGATCTGGGACAGAT
TTTACTTTCACCATCAGCAGCCTGCAGCCTGAAGATATTGCAACATATTACTG
TCAACAGTATGAGGATCTCCCTACTTTCGGCCCTGGGACCAAAGTGGATATCA
AACGAACCGTGGCTGCACCATCTGTCTTCATCTTCCCGCCATCTGATGAGCAG
TTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAG
GGGAGAGTGC Ab2
SEQ ID NO: 1 HCDR1 (North) for Ab1, Ab2, and Ab3
AASGFTFSSYAMS SEQ ID NO: 2 HCDR2 (North) for Ab1, Ab2, and Ab3
AISGSGGSTY SEQ ID NO: 3 HDCR3 (North) for Ab2 and Ab3
ARTYSNYDY SEQ ID NO: 4 LCDR1 (North) for Ab2
QASQPTFNYLN SEQ ID NO: 5 LCDR2 (North) for Ab1, Ab2, and Ab3
YDASNLQT SEQ ID NO: 6 LCDR3 (North) for Ab1, Ab2, and Ab3
QQYEDLPT SEQ ID NO: 7 VH for Ab2 and Ab3
EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCARTYSNYDYWG
QGTLVTVSS SEQ ID NO: 8 VL for Ab2
DIQMTQSPSSLSASVGDRVTITCQASQPTFNYLNWYQQKPGKAPKLLIYDASNLQ
TGVPSRFSGSGSGTDFTFTISSLQPEDIATYYCQQYEDLPTFGPGTKVDIK SEQ ID NO: 9 HC for Ab2 and Ab3
EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCARTYSNYDYWG
QGTLVTVSSASTKGPCVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKS
CDKTHTCPPCPAPEAAGGPSVFLFPPKPKDTLMISRTPEVTCVVVDVSHEDPEVKF -continued

| SEQUENCE LISTING |
| --- |

NWYVDGVEVHNAKTKPREEQYNSTYRVVSVLTVLHQDWLNGKEYKCKVSNKA
LAAPIEKTISKAKGQPREPQVYTLPPSREEMTKNQVSLTCLVKGFYPSDICVEWES
NGQPENNYKTTPPVLDSDGSFFLYSKLTVDKSRWQQGNVFSCSVMHEALHNHY
TQKSLSLSPGK

SEQ ID NO: 10 LC for Ab2
DIQMTQSPSSLSASVGDRVTITCQASQPTFNYLNWYQQKPGKAPKLLIYDASNLQ
TGVPSRFSGSGSGTDFTFTISSLQPEDIATYYCQQYEDLPTFGPGTKVDIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 11 HC DNA for Ab2 and Ab3
GAGGTGCAGCTGTTGGAGTCTGGGGGAGGCTTGGTACAGCCTGGGGGGTCCC
TGAGACTCTCCTGTGCAGCCTCTGGATTCACCTTTAGCAGCTATGCCATGAGC
TGGGTCCGCCAGGCTCCAGGGAAGGGGCTGGAGTGGGTCTCAGCTATTAGTG
GTAGTGGTGGTAGCACATACTACGCAGACTCCGTGAAGGGCCGGTTCACCAT
CTCCAGAGACAATTCCAAGAACACGCTGTATCTGCAAATGAACAGCCTGAGA
GCCGAGGACACGGCCGTATATTACTGTGCGAGGACTTATAGTAATTATGACT
ACTGGGGTCAGGGAACCCTGGTCACCGTCTCCTCAGCTAGCACCAAGGGCCC
ATGCGTCTTCCCCCTGGCACCCTCCTCCAAGAGCACCTCTGGGGGCACAGCGG
CCCTGGGCTGCCTGGTCAAGGACTACTTCCCCGAACCGGTGACGGTGTCGTGG
AACTCAGGCGCACTGACCAGCGGCGTGCACACCTTCCCGGCTGTCCTACAGTC
CTCAGGACTCTACTCCCTCAGCAGCGTGGTGACCGTGCCCTCCAGCAGCTTGG
GCACCCAGACCTACATCTGCAACGTGAATCACAAGCCCAGCAACACCAAGGT
GGACAAGAGAGTTGAGCCCAAATCTTGTGACAAAACTCACACATGCCCACCG
TGCCCAGCACCTGAAGCCGCCGGGGGACCGTCAGTCTTCCTCTTCCCCCCAAA
ACCCAAGGACACCCTCATGATCTCCCGGACCCCTGAGGTCACATGCGTGGTG
GTGGACGTGAGCCACGAAGACCCTGAGGTCAAGTTCAACTGGTATGTGGACG
GCGTGGAGGTGCATAATGCCAAGACAAAGCCGCGGGAGGAGCAGTACAACA
GCACGTACCGTGTGGTCAGCGTCCTCACCGTCCTGCACCAAGACTGGCTGAAT
GGCAAGGAGTACAAGTGCAAGGTCTCCAACAAAGCCCTCGCCGCCCCCATCG
AGAAAACCATCTCCAAAGCCAAAGGGCAGCCCCGAGAACCACAGGTGTACA
CCCTGCCCCCATCCCGGGAGGAGATGACCAAGAACCAAGTCAGCCTGACCTG
CCTGGTCAAAGGCTTCTATCCCAGCGACATCTGCGTGGAGTGGGAGAGCAAT
GGGCAGCCGGAGAACAACTACAAGACCACGCCTCCCGTGCTGGACTCCGACG
GCTCCTTCTTCCTCTATTCCAAGCTCACCGTGGACAAGAGCAGGTGGCAGCAG
GGGAACGTCTTCTCATGCTCCGTGATGCATGAGGCTCTGCACAACCACTACAC
GCAGAAGAGCCTCTCCCTGTCTCCGGGCAAA SEQ ID NO: 12 LC DNA for Ab2
GACATCCAGATGACCCAGTCTCCATCCTCCCTGTCTGCATCTGTAGGAGACAG
AGTCACCATCACTTGCCAGGCGAGTCAGCCGACGTTCAATTATTTAAATTGGT
ATCAGCAGAAACCAGGGAAAGCCCCTAAGCTCCTGATCTACGATGCATCCAA
TTTGCAAACAGGGGTCCCATCAAGGTTCAGTGGAAGTGGATCTGGGACAGAT
TTTACTTTCACCATCAGCAGCCTGCAGCCTGAAGATATTGCAACATATTACTG
TCAACAGTATGAGGATCTCCCTACTTTCGGCCCTGGGACCAAAGTGGATATCA
AACGAACCGTGGCTGCACCATCTGTCTTCATCTTCCCGCCATCTGATGAGCAG
TTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAG
GGGAGAGTGC Ab3
SEQ ID NO: 1 HCDR1 (North) for Ab1, Ab2, and Ab3
AASGFTFSSYAMS SEQ ID NO: 2 HCDR2 (North) for Ab1, Ab2, and Ab3
AISGSGGSTY SEQ ID NO: 3 HDCR3 (North) for Ab2 and Ab3
ARTYSNYDY SEQ ID NO: 13 LCDR1 (North) for Ab3
QASQPTYIYLN SEQ ID NO: 5 LCDR2 (North) for Ab1, Ab2, and Ab3
YDASNLQT SEQ ID NO: 6 LCDR3 (North) for Ab1, Ab2, and Ab3
QQYEDLPT SEQ ID NO: 7 VH for Ab2 and Ab3
EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCARTYSNYDYWG
QGTLVTVSS -continued

SEQUENCE LISTING

SEQ ID NO: 14 VL for Ab3
DIQMTQSPSSLSASVGDRVTITCQASQPTYIYLNWYQQKPGKAPKLLIYDASNLQ
TGVPSRFSGSGSGTDFTFTISSLQPEDIATYYCQQYEDLPTFGPGTKVDIK SEQ ID NO: 9 HC for Ab2 and Ab3
EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCARTYSNYDYWG
QGTLVTVSSASTKGPCVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKS
CDKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LAAPIEKTISKAKGQPREPQVYTLPPSREEMTKNQVSLTCLVKGFYPSDICVEWES
NGQPENNYKTTPPVLDSDGSFFLYSKLTVDKSRWQQGNVFSCSVMHEALHNHY
TQKSLSLSPGK SEQ ID NO: 15 LC for Ab3
DIQMTQSPSSLSASVGDRVTITCQASQPTYIYLNWYQQKPGKAPKLLIYDASNLQ
TGVPSRFSGSGSGTDFTFTISSLQPEDIATYYCQQYEDLPTFGPGTKVDIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 11 HC DNA for Ab2 and Ab3
GAGGTGCAGCTGTTGGAGTCTGGGGGAGGCTTGGTACAGCCTGGGGGGTCCC
TGAGACTCTCCTGTGCAGCCTCTGGATTCACCTTTAGCAGCTATGCCATGAGC
TGGGTCCGCCAGGCTCCAGGGAAGGGGCTGGAGTGGGTCTCAGCTATTAGTG
GTAGTGGTGGTAGCACATACTACGCAGACTCCGTGAAGGGCCGGTTCACCAT
CTCCAGAGACAATTCCAAGAACACGCTGTATCTGCAAATGAACAGCCTGAGA
GCCGAGGACACGGCCGTATATTACTGTGCGAGGACTTATAGTAATTATGACT
ACTGGGGTCAGGGAACCCTGGTCACCGTCTCCTCAGCTAGCACCAAGGGCCC
ATGCGTCTTCCCCCTGGCACCCTCCTCCAAGAGCACCTCTGGGGGCACAGCGG
CCCTGGGCTGCCTGGTCAAGGACTACTTCCCCGAACCGGTGACGGTGTCGTGG
AACTCAGGCGCACTGACCAGCGGCGTGCACACCTTCCCGGCTGTCCTACAGTC
CTCAGGACTCTACTCCCTCAGCAGCGTGGTGACCGTGCCCTCCAGCAGCTTGG
GCACCCAGACCTACATCTGCAACGTGAATCACAAGCCCAGCAACACCAAGGT
GGACAAGAGAGTTGAGCCCAAATCTTGTGACAAAACTCACACATGCCCACCG
TGCCCAGCACCTGAAGCCGCCGGGGGACCGTCAGTCTTCCTCTTCCCCCCAAA
ACCCAAGGACACCCTCATGATCTCCCGGACCCCTGAGGTCACATGCGTGGTG
GTGGACGTGAGCCACGAAGACCCTGAGGTCAAGTTCAACTGGTATGTGGACG
GCGTGGAGGTGCATAATGCCAAGACAAAGCCGCGGGAGGAGCAGTACAACA
GCACGTACCGTGTGGTCAGCGTCCTCACCGTCCTGCACCAAGACTGGCTGAAT
GGCAAGGAGTACAAGTGCAAGGTCTCCAACAAAGCCCTCGCCGCCCCCATCG
AGAAAACCATCTCCAAAGCCAAAGGGCAGCCCCGAGAACCACAGGTGTACA
CCCTGCCCCCATCCCGGGAGGAGATGACCAAGAACCAAGTCAGCCTGACCTG
CCTGGTCAAAGGCTTCTATCCCAGCGACATCTGCGTGGAGTGGGAGAGCAAT
GGGCAGCCGGAGAACAACTACAAGACCACGCCTCCCGTGCTGGACTCCGACG
GCTCCTTCTTCCTCTATTCCAAGCTCACCGTGGACAAGAGCAGGTGGCAGCAG
GGGAACGTCTTCTCATGCTCCGTGATGCATGAGGCTCTGCACAACCACTACAC
GCAGAAGAGCCTCTCCCTGTCTCCGGGCAAA SEQ ID NO: 16 LC DNA for Ab3
GACATCCAGATGACCCAGTCTCCATCCTCCCTGTCTGCATCTGTAGGAGACAG
AGTCACCATCACTTGCCAGGCGAGTCAGCCTACGTATATCTATTTAAATTGGT
ATCAGCAGAAACCAGGGAAAGCCCCTAAGCTCCTGATCTACGATGCATCCAA
TTTGCAAACAGGGGTCCCATCAAGGTTCAGTGGAAGTGGATCTGGGACAGAT
TTTACTTTCACCATCAGCAGCCTGCAGCCTGAAGATATTGCAACATATTACTG
TCAACAGTATGAGGATCTCCCTACTTTCGGCCCTGGGACCAAAGTGGATATCA
AACGAACCGTGGCTGCACCATCTGTCTTCATCTTCCCGCCATCTGATGAGCAG
TTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAG
GGGAGAGTGC SEQ ID NO: 25 Human CD33
MPLLLLLPLLWAGALAMDPNFWLQVQESVTVQEGLCVLVPCTFFHPIPYYDKNS
PVHGYWFREGAIISRDSPVATNKLDQEVQEETQGRFRLLGDPSRNNCSLSIVDAR
RRDNGSYFFRMERGSTKYSYKSPQLSVHVTDLTHRPKILIPGTLEPGHSKNLTCSV
SWACEQGTPPIFSWLSAAPTSLGPRTTHSSVLIITPRPQDHGTNLTCQVKFAGAGV
TTERTIQLNVTYVPQNPTTGIFPGDGSGKQETRAGVVHGAIGGAGVTALLALCLC
LIFFIVKTHRRKAARTAVGRNDTHPTTGSASPKHQKKSKLHGPTETSSCSGAAPT
VEMDEELHY ASLNFHGMNPSKDTSTEYSEVRTQ -continued

SEQUENCE LISTING

SEQ ID NO: 26 LCDR1 Consensus Sequence
QASQPTXaa$_7$Xaa$_8$IYLN
Wherein Xaa$_7$ is Phenylalanine or Tyrosine, and Xaa$_8$ is Asparagine or Isoleucine SEQ ID NO: 27 Cynomolgus monkey CD33
MPLLLLPLLWAGALAMDPRVRLEVQESVTVQEGLCVLVPCTFFHPVPYHTRNSP
VHGYWFREGAIVSLDSPVATNKLDQEVQEETQGRFRLLGDPSRNNCSLSIVDARR
RDNGSYFFRMEKGSTKYSYKSTQLSVHVTDLTHRPQILIPGALDPDHSKNLTCSV
PWACEQGTPPIFSWMSAAPTSLGLRTTHSSVLIITPRPQDHGTNLTCQVKFPGAGV
TTERTIQLNVSYASQNPRTDIFLGEGSGRKARKQGVVQGAIGGAGVTVLLALCLC
LIFFTVKTHRRKAARTAVGRIDTHPATGPTSSKHQKKSKLHGATETSGCSGTTLT
VEMDEELHYASLNFHGMNPSEDTSTEYSEVRTQ SEQ ID NO: 28 Human CD33 extra-cellular domain
DPNFWLQVQESVTVQEGLCVLVPCTFFHPIPYYDKNSPVHGYWFREGAIISRDSP
VATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSA
APTSLGPRTTHSSVLIITPRPQDHGTNLTCQVKFAGAGVTTERTIQLNVT SEQ ID NO: 29 Cynomolgus monkey CD33 extra-cellular domain
DPRVRLEVQESVTVQEGLCVLVPCTFFHPVPYHTRNSPVHGYWFREGAIVSLDSP
VATNKLDQEVQEETQGRFRLLGDPSRNNCSLSIVDARRRDNGSYFFRMEKGSTK
YSYKSTQLSVHVTDLTHRPQILIPGALDPDHSKNLTCSVPWACEQGTPPIFSWMS
AAPTSLGLRTTHSSVLIITPRPQDHGTNLTCQVKFPGAGVTTERTIQLNVS

What is claimed is:

1. An antibody that binds human CD33, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein:
- i. the HCDR1 comprises SEQ ID NO: 1,
  the HCDR2 comprises SEQ ID NO: 2,
  the HCDR3 comprises SEQ ID NO: 3,
  the LCDR1 comprises SEQ ID NO: 4,
  the LCDR2 comprises SEQ ID NO: 5, and
  the LCDR3 comprises SEQ ID NO: 6;
- ii. the HCDR1 comprises SEQ ID NO: 1,
  the HCDR2 comprises SEQ ID NO: 2,
  the HCDR3 comprises SEQ ID NO: 3,
  the LCDR1 comprises SEQ ID NO: 13,
  the LCDR2 comprises SEQ ID NO: 5, and
  the LCDR3 comprises SEQ ID NO: 6; or
- iii. the HCDR1 comprises SEQ ID NO: 1,
  the HCDR2 comprises SEQ ID NO: 2,
  the HCDR3 comprises SEQ ID NO: 17,
  the LCDR1 comprises SEQ ID NO: 18,
  the LCDR2 comprises SEQ ID NO: 5, and
  the LCDR3 comprises SEQ ID NO: 6.

2. The antibody of claim 1, wherein,
- i. the VH comprises SEQ ID NO: 7 and the VL comprises SEQ ID NO: 8;
- ii. the VH comprises SEQ ID NO: 7 and the VL comprises SEQ ID NO: 14; or
- iii. the VH comprises SEQ ID NO: 19 and the VL comprises SEQ ID NO: 20.

3. The antibody of claim 1, wherein the antibody comprises a heavy chain (HC) and a light chain (LC), wherein
- i. the HC comprises SEQ ID NO: 9 and the LC comprises SEQ ID NO: 10;
- ii. the HC comprises SEQ ID NO: 9 and the LC comprises SEQ ID NO: 15; or
- iii. the HC comprises SEQ ID NO: 21 and the LC comprises SEQ ID NO: 22.

4. The antibody of claim 1, wherein the antibody comprises a heavy chain (HC) and a light chain (LC), wherein the HC is human IgG1 isotype.

5. The antibody of claim 1, wherein the antibody is an internalizing antibody.

6. The antibody of claim 1, wherein the antibody is a non-depleting antibody.

7. The antibody of claim 1, wherein the antibody is a non-degrading antibody.

8. A nucleic acid comprising a sequence encoding SEQ ID NO: 9, 10, 15, 21, or 22.

9. A vector comprising the nucleic acid of claim 8.

10. The vector of claim 9, wherein,
- i. the vector comprises a first nucleic acid sequence encoding SEQ ID NO: 9 and a second nucleic acid sequence encoding SEQ ID NO: 10;
- ii. the vector comprises a first nucleic acid sequence encoding SEQ ID NO: 9 and a second nucleic acid sequence encoding SEQ ID NO: 15; or
- iii. the vector comprises a first nucleic acid sequence encoding SEQ ID NO: and a second nucleic acid sequence encoding SEQ ID NO: 22.

11. A composition comprising:
- i. a first vector comprising a nucleic acid sequence encoding SEQ ID NO: 21 and a second vector comprising a nucleic acid sequence encoding SEQ ID NO: 22;
- ii. first vector comprising a nucleic acid sequence encoding SEQ ID NO: 9 and a second vector comprising a nucleic acid sequence encoding SEQ ID NO: 10; or
- iii. a first vector comprising a nucleic acid sequence encoding SEQ ID NO: 9 and a second vector comprising a nucleic acid sequence encoding SEQ ID NO: 15.

12. A cell comprising the vector of claim 9.

13. A cell comprising the vector of claim 10.

14. The cell of claim 12, wherein the cell is a mammalian cell.

15. The cell of claim 13, wherein the cell is a mammalian cell.

16. A process of producing an antibody comprising culturing the cell of claim 15, under conditions such that the antibody is expressed and recovering the expressed antibody from the culture medium.

17. An antibody produced by the process of claim 16.

18. A conjugate comprising an antibody of claim 1, wherein the antibody is conjugated to a therapeutic agent.

19. The conjugate of claim 18, wherein the therapeutic agent comprises a cytotoxic agent, siRNA, saRNA, peptide, oligonucleotide, small molecule, nanoparticle, lipid nanoparticle, exosome, antibody or antigen binding fragment thereof, or a combination thereof.

* * * * *